(12) United States Patent
Desmet et al.

(10) Patent No.: US 8,229,721 B1
(45) Date of Patent: Jul. 24, 2012

(54) APPARATUS AND METHOD FOR STRUCTURE-BASED PREDICTION OF AMINO ACID SEQUENCES

(75) Inventors: Johan Desmet, Kortrijk (BE); Ignace Lasters, Antwerp (BE); Dominique Vlieghe, Kortrijk (BE); Carlo Boutton, Zwevegem (BE); Philippe Stas, Welle (BE)

(73) Assignee: Lonza Biologics plc, Slough (GB)

( * ) Notice: Subject to any disclaimer, the term of this patent is extended or adjusted under 35 U.S.C. 154(b) by 149 days.

(21) Appl. No.: 10/129,513

(22) PCT Filed: Nov. 3, 2000

(86) PCT No.: PCT/EP00/10923
§ 371 (c)(1),
(2), (4) Date: Sep. 30, 2002

(87) PCT Pub. No.: WO01/37147
PCT Pub. Date: May 25, 2001

Related U.S. Application Data

(60) Provisional application No. 60/163,409, filed on Nov. 3, 1999.

(51) Int. Cl.
*G06G 7/48* (2006.01)
*G01N 33/48* (2006.01)
*G06F 19/00* (2011.01)

(52) U.S. Cl. ............................... 703/11; 702/19; 702/27

(58) Field of Classification Search .................... 702/19, 702/20, 27
See application file for complete search history.

(56) References Cited

U.S. PATENT DOCUMENTS

| | | | | |
|---|---|---|---|---|
| 4,939,666 | A * | 7/1990 | Hardman | 700/293 |
| 6,188,965 | B1 * | 2/2001 | Mayo et al. | 702/27 |
| 6,230,102 | B1 * | 5/2001 | Tidor et al. | 702/19 |
| 6,269,312 | B1 | 7/2001 | Mayo et al. | |
| 6,490,532 | B1 * | 12/2002 | Hogue et al. | 702/27 |
| 2001/0032052 | A1 | 10/2001 | Mayo et al. | |
| 2001/0039480 | A1 | 11/2001 | Mayo et al. | |
| 2002/0004706 | A1 | 1/2002 | Mayo et al. | |

FOREIGN PATENT DOCUMENTS

| | | |
|---|---|---|
| WO | WO 98/47089 | 10/1998 |
| WO | PCT/EP00/09460 | 9/2000 |
| WO | WO 01/33438 | 5/2001 |

OTHER PUBLICATIONS

U.S. Appl. No. 10/129,516, filed Nov. 3, 2000, Desmet et al.
Allen and Mayo, "Dramatic Performance Enhancements for the FASTER Optimization Algorithm," *Journal of Computational Chemistry*, 27:1071-1075, 2006.
Dahiyat and Mayo, "De Novo Protein Design: Fully Automated Sequence Selection," *Science*, 278:82-87, 1997.
Dahiyat and Mayo, "Protein Design Automation," *Protein Science*, 5:895-903, 1996.
Desmet et al., "Theoretical and Algorithmical Optimization of the Dead-End Elimination Theorem," 122-133, 1997.
Desmet et al., "Fast and Accurate Side-Chain Topology and Energy Refinement (FASTER) as a New Method for Protein Structure Optimization," *Proteins*, 48:31-43, 2002.
Gordon and Mayo, "Branch-and-Terminate: A Combinatorial Optimization Algorithm for Protein Design," *Structure*, 7:1089-1097, 1999.
Wako and Ishii, "Secondary Structure Prediction of β-subunits of the Gonadotrophin-Thyrotropin Family From its Aligned Sequences Using Environment-Dependent Amino-Acid Substitution Tables and Conformational Propensities," *Biochemica et Biophysica Acta*, 1247:104-112, 1995.
Wernisch et al., "Automatic Protein Design with All Atom Force-Fields by Exact and Heuristic Optimization," *Journal of Molecular Biology*, 301:713-736, 2000.
International Preliminary Report on Patentability (PCT/EP00/10921), completed Apr. 16, 2002.
International Preliminary Report on Patentability (PCT/EP00/10923), completed Oct. 17, 2002.
International Search Report (PCT/EP00/10921), mailed Dec. 17, 2001.
International Search Report (PCT/EP00/10923), mailed Mar. 12, 2002.
Office Action (U.S. Appl. No. 10/129,516), mailed Apr. 18, 2008.
U.S. Appl. No. 12/959,224, filed Dec. 2, 2010, Desmet et al.
U.S. Appl. No. 13/020,452, filed Feb. 3, 2011, Desmet et al.
Desmet et al., "The Dead-end Elimination Theorem and Its Use in Protein Side-Chain Positioning," *Nature* 356:539-542, 1992.
Milchev and Rouault, "A Monte Carlo Study of Thermodynamic Relaxation in Living Polymers," *J. Phys. II France*. 5:343-347, 1995.
Restriction Requirement (U.S. Appl. No. 10/129,516), mailed Dec. 14, 2007.
Reply to Restriction Requirement (U.S. Appl. No. 10/129,516), filed Jan. 14, 2008.

(Continued)

*Primary Examiner* — Eric S DeJong
(74) *Attorney, Agent, or Firm* — Clark & Elbing LLP

(57) ABSTRACT

The invention provides methods and apparatus for analyzing a protein structure by
A) receiving a reference structure (A) forming a three dimensional representation of a protein;
B) substituting into the structure of (A) a pattern with amino-acids different from the one of the protein;
C) optimizing the conformation of (A) substituted by pattern of (B);
D) assessing the energetic compatibility (EC) of the pattern of (B) within the context of the structure of (A) being structurally optimized in (C) with respect to the pattern, by comparing the global energy of the substituted and optimized protein structure with the global energy of the non-substituted reference structure; and
E) storing a value reflecting the EC of the pattern together with information related to the structure of the pattern in the form of an energetic compatibility object (ECO).

13 Claims, 5 Drawing Sheets

OTHER PUBLICATIONS

Reply to Office Action (U.S. Appl. No. 10/129,516), filed Aug. 21, 2008.
Office Action (U.S. Appl. No. 10/129,516), mailed Jan. 8, 2009.
Reply to Office Action (U.S. Appl. No. 10/129,516), filed May 7, 2009.
Office Action (U.S. Appl. No. 10/129,516), mailed Aug. 14, 2009.
Reply to Office Action (U.S. Appl. No. 10/129,516), filed Jan. 14, 2010.
Final Office Action (U.S. Appl. No. 10/129,516), mailed Mar. 25, 2010.
Reply to Final Office Action (U.S. Appl. No. 10/129,516), filed Jul. 26, 2010.
Extended European Search Report for European Patent Application No. 10179441.0, dated Mar. 4, 2011.
Official Communication for European Patent Application No. 00 984 970.4, dated Oct. 8, 2010.
Non-final Office Action (U.S. Appl. No. 12/959,224), mailed Mar. 1, 2012.
Official Communication for European Patent Application No. 10179441.0, dated Apr. 10, 2012 (5 pages).

* cited by examiner

```
Frag    From      To      length  score   score/res  P_random
 1   (   1,   1) (  13,  13)  13    17.48   1.344     0.6330E-06
 2   (  17,  19) (  46,  48)  30    36.44   1.215     0.1516E-10
 3   (  50,  53) (  95,  98)  46    52.00   1.130     0.8939E-14
 4   (  69,  36) (  72,  39)   4     8.23   2.056     0.2021E-04
 5   (  92,  42) ( 103,  53)  12    13.95   1.162     0.2849E-04
 6   (  92,  69) ( 102,  79)  11    13.19   1.199     0.3519E-04
 7   (  95,  55) ( 110,  70)  16    22.68   1.417     0.7350E-08
 8   ( 102,106) ( 115,119)   14    15.42   1.101     0.1936E-04
 9   ( 105,  56) ( 109,  60)   5     9.59   1.917     0.9136E-05
10   ( 114,104) ( 118,108)   5     9.02   1.804     0.2849E-04
```

```
         1|        11|        21|        31|        41|        51|        61|        71|        81|        91|       101|       111|       121|
     KVFGRCELAAAMKRHGLDNYRGYSLGNWVCAAKFESNFNTQATNRNTDGSTDYGIILQINSRWWCNDGRTPGSRNLCNIPCSALLSSDITASVNCAKKIVSDGNGMNAWVAWRNRCKGTDVQAWIRGCRL
     +-+-+-++++-+
 1   KQFTKCELSQLLK

++-++-+++-+++-+++++-+-+++
17                   GYGIALPELICTMFHTSGYDTQAIVENDE

++++-+++-+++-+++++-+-+++-+-+++++-+-+++++++
50                                                     YGLFQISNKLWCKSSQVPQSRNICDISCDKFLDDITDDIMCAKKI

++++
69                                              SRNI

++++++++++-+++
92                                                                  AKKILDIKGIDY

+++-+++++-+++
92                                                                     AKKILDIKGID

++++++++++-+-+++
95                                                              ILDIKGIDYWLAHKAL

+++++
102                                        LAHKA

+-+++++++-+++-+++
105                                                                                                        DYWLAHKALCTEKL

+++++
114                                                                                                             KLEQW

Profile: KVFGRCELAAAMKrhgldNYRGYSLGNWVCAAKFESNFNTQATNRNTDgstdYGIILQINSRWWCNDGRTPGSRNLCNIPCSALLSSDITASVNCAKKIvsdgngmNWVAWRNRCKGTDvqawirgcrl
Match  : +-++-+++++--+++OOO+++-+-+++-+++-+++++-+-+++-+-+++++-+-+++++++OOOOOO-+-+++-+++-+++++-+-+++-+-+++++++OOOOOOOOO
Target : KQFTKCELSQLLKdid..GYGIALPELICTMFHTSGYDTQAIVENDEste.YGLFQISNKLWCKSSQVPQSRNICDISCDKFLDDITDDIMCAKKIldikgi.DYWLAHKALCTEKLeqwlcekl..
```

FIG. 4

APPARATUS AND METHOD FOR STRUCTURE-BASED PREDICTION OF AMINO ACID SEQUENCES

CROSS-REFERENCE TO RELATED APPLICATIONS

This application is the U.S. National Stage of International Application No. PCT/EP00/10923, filed Nov. 3, 2000, which claims the benefit of U.S. Provisional Application No. 60/163,409, filed Nov. 3, 1999.

FIELD OF THE INVENTION

The present invention relates to the field of genomics as well as to the field of protein engineering, in particular, an apparatus and method to determine the amino acid sequence space accessible to a given protein structure and to use this information (i) to align an amino acid sequence with a protein structure in order to identify a potential structural relationship between said sequence and structure, which is known in the art as fold recognition and (ii) to generate new amino acid sequences which are compatible with a protein structure, which is known in the art as protein design.

BACKGROUND OF THE INVENTION

Within the field of bioinformatics there is an emerging need for so-called data mining tools. These tools aim at unraveling relationships that connect more elementary data components such as oligo-nucleotide and amino acid sequences, single-nucleotide polymorphisms (hereinafter referred as SNP), expression profiles, biochemical properties, structural and functional characterization, and so on. These relationships represent knowledge that can be used to build so-called knowledge databases that offer a structured description (e.g. via annotation mechanisms) of the more elementary data components such as above defined. Knowledge databases will increasingly play a key role in the biotechnology industry since they form an inference basis from which the behavior of biological systems can be understood, predicted and possibly controlled via proper biotechnological engineering.

The need for data mining tools is further increased by the availability of rich, well annotated sequence databases which offer an in silico basis for new gene hunting approaches. Here the determination of sequence-to-structure relationships is playing a crucial role, also for those who are essentially not interested in structural information. Indeed, via sequence-to-structure relationships, often distant similarities with other proteins can be found. Such similarities are unlikely to be found by direct sequence comparisons if the sequence identity drops below the 25% level, according to R. F. Doolittle in *Urfs and Orfs. A primer on how to analyze derived amino acid sequences* (1986) at University Science Books, Mill Valey (Calif.) and Sander et al. in *Proteins* (1991) 9:56-68.

Conversely, structure-to-sequence relationships are also rapidly gaining attention for several reasons. Firstly, the available experimental basis has recently evolved towards a mature stage, since the number of known protein structures has now reached over 12,000. Depending on the classification method, these structures represent about 600 to 700 unique folds, i.e. about 60 to 70% of the estimated total number of about 1000 possible folds adopted by naturally-occurring proteins, according to C. Chothia in *Nature* (1992) 357:543-544. Secondly, the available technological basis has also made a giant leap since new methods for side-chain positioning (according to M. Vásquez in Curr. Opin. Struct. Biol. (1996) 6:217-221), loop modeling (according to Sudarsanam et al. in Protein Sci. (1995) 4:1412-1420), inverse folding (according to Bowie et al. in *Science* (1991) 253:164-170), protein design (according to Dahiyat et al. in *Science* (1997) 278:82-87) and so on continuously appear in the literature, which methods also benefit from computer devices becoming more and more powerful. Third, the scientific community has started recognizing the potential of structure-based protein engineering as can be inferred from the growing number of companies in this field and the success of initiatives like the Critical Assessment of Techniques for Protein Structure Prediction (CASP) contests (PredictionCenter.llnl.gov/) and the structural genomics initiative (www.nigms.nih.gov/funding/psi.html).

Tools which are able to link a given amino acid sequence to the correct three-dimensional (hereinafter referred as 3D) fold or compute the amino acid sequences that are compatible with a given protein structure are very valuable. Given the myriad of world-wide known sequences and structures, distributed over different databases, some crucial parameters for determining the success of any such method are prediction accuracy and computational speed.

The present invention relates to a novel approach to link one or more amino acid sequences with one or more protein 3D structures and vice versa. More particularly, the invention concerns a new method preserving the accuracy of the most accurate atom-based modeling techniques currently known while avoiding the bottleneck-problem known as the "combinatorial substitution problem", thereby gaining several orders of magnitude in computational speed.

The fundamental problem to be addressed by the present invention relates to multiple combined substitutions in a protein and can be illustrated by the following example. We shall consider a protein X for which the 3D structure has been experimentally determined. This structure is called the wild-type (WT) structure and the amino acid sequence of protein X is called the WT sequence. We shall further assume that X is an enzyme used in an industrial process and that there is interest in constructing a modified protein X' showing a considerably higher thermal stability than the wild type X, while preserving the latter's functionality. While such problems have often been addressed by introducing point mutations (i.e. the substitution of single amino acid residues at selected positions), it has been shown that the simultaneous mutation of multiple amino acid residues is usually more efficient, according to International Application Publication No. WO 98/47089. On the other hand the latter approach, known as protein design, is extremely complicated in view of the extremely high number of a priori possible combinations of single residue mutations. For example if the aforementioned task of thermally stabilizing protein X was limited to substitutions in the core of a protein (i.e. the internal part of a protein where strictly buried residues are located) containing e.g. 15 residues, and if only 10 (preferably apolar) residue types were considered, there would still be $10^{15}$ a priori possible solutions. Each such solution represents an amino acid sequence which is different from that of protein X and is, in principle, a candidate sequence for protein X'. In order to predict which sequences are more stable than the WT sequence, one could apply a fast molecular modeling program, predict the 3D-structure of each sequence, compute the potential or free energy of each modeled structure and store the best results. However, clearly no modeling program is at present fast enough to complete this task in an reasonable period of time.

The former example illustrates the main bottleneck problem in protein design, which is known in the art as the "combinatorial substitution problem" and which arises from the fact that different individual substitutions in a protein are, in principle, not independent as shown in FIG. 1a. The energy of a protein comprising a double substitution may not be simply calculated from the structures of two single mutants, because both mutated amino acid residues are "unaware" from each other in the single mutants, i.e. the single mutant structures lack any information about the interaction between both substituted amino acid residues in the double mutant. Consequently the simultaneous introduction of two or more substitutions into the protein to be modeled may lead to either favorable or unfavorable interactions which cannot be derived from the structure of single mutants. When performing such multiple substitutions, some information about the pair-wise interactions between the removed WT residues and the introduced mutant residues should therefore be taken into account.

On the other hand, there are also cases where combinatorial effects do not play a significant role, i.e. where single substitutions are independent from each other and where individual substitution energies are additive as shown in FIG. 1b. Moreover, there is also experimental evidence, at least in some cases, that the energetic contributions of different individual mutations are additive according to A. Ferhst in *Enzyme Structure and Mechanism* (1985), ISBN 0-7167-1614-3. This is so for example when two individual substitutions are separated in space in a manner such that the pair-wise interaction between both residues is negligibly small for both the WT residues and the substituted residues. However this no-interaction condition is not sufficient to conclude that two substitutions may be considered independently. Indeed, although two residues do not directly interact with each other, they may still be coupled through conformational adaptation of residues in their vicinity according to FIG. 1c. In general, this type of coupling depends on the "plasticity" of the protein (plasticity: the ability to cushion conformational changes). Non-direct, conformational coupling may for instance occur when two simultaneously substituted residues leave an intermediate residue in a situation where no conformational solution exists which leads to favorable energetic interactions with both mutated residues. Such an intermediate residue could be considered as "non-plastic" with respect to the concerned pair of substituted residues.

Going back to the previous example of the enzyme X needing to be stabilized, this means that the modeling task cannot be performed by simply proposing a molecule X' comprising a set of substitutions which have each been modeled independently in the WT structure. On the other hand, a mere combinatorial enumeration of all possible global structures is extremely inefficient from a computational perspective and can be considered as undue work with respect to the primary goal of predicting an enzyme X' having an optimal thermal stability.

However, several authors tackled the side-chain positioning problem in proteins by means of a combinatorial approach or equivalent method. For instance, the Dead-End Elimination (DEE) method takes into account both side-chain/template and side-chain/side-chain interactions and uses a mathematically rigorous criterion to eliminate side-chain rotamers which do not belong to the Global Minimum Energy Conformation (GMEC). Since the DEE routines usually do not converge towards a unique structure, a combinatorial end stage routine is needed to determine the GMEC. It was thus demonstrated, namely by Gordon et al. in Fold. Des. (1999) 7:1089-1098, and Wernisch et al. In J. Mol. Biol. (2000) 301:713-736 that the combinatorial problem for multiple substitutions can be alleviated, by means of DEE, by eliminating a number of potential substitutions which cannot be part of the globally best solution, i.e. the most stable protein molecule. Since eliminations occur at the single or pair residue level, they result in a huge reduction of the search space since all combinations therewith are eliminated as well. Nevertheless, the DEE method is a valuable method to reduce the complexity of a system. The main disadvantages of the DEE method are (1) non-convergence towards a unique structure, as above-mentioned, (2) the inability to predict "second best" solutions and (3) a relatively weak performance for large systems (i.e. having more than about 30 residues), due to a mathematically stringent process which complicates the use of approximations.

One problem to be addressed by the present invention is to develop a method rapidly and accurately predicting the compatibility of one or more amino acid sequences with one or more protein 3D-structures. The requirement of accuracy strongly pleads for the use of a detailed, atom-based force field (energy function) to compute the local and other interactions of a set of amino acid residues placed onto a 3D-structure. Furthermore, the above example showed that a correct positioning, using said interaction energies, is severely hampered by the combinatorial problem. On the other hand, all current methods which fully account for combinatorial effects are in conflict with the second requirement of a high computational speed. This constitutes the major dilemma in protein modeling, more specifically in fold recognition and protein design.

In order to determine sequences that are reachable by a given protein structure and/or to identify the best-matching protein 3D-structure, given a particular sequence, one may use (1) prediction algorithms relying on statistically derived substitution matrices, (2) prediction algorithms based on statistical descriptors, and (3) computation of explicit conformational energies, corrected for solvation effects.

In the approach using descriptors, a set of reference proteins (often referred to as the learning set) is used to derive properties that can statistically be used to judge the propensity for any given amino acid type to be present in some given structural environment. For example, in the original derivation of the 3D-profiles of Bowie et al. in *Science* (1991) 253:164-9, the environment of each residue is featured by (a) a buried side chain area, (b) a local secondary structure and (c) the polarity of the environment. Using these features, the authors recognized 18 environmental classes. As a result, any given protein structure can be transformed into a linear string composed of the class identifiers for each position along the protein's sequence. From a database of proteins of known structure, a so-called 3D-to-1D scoring table is built to assign a score for finding each of the 20 naturally-occurring amino acid types associated with each of the environmental classes. Using this scoring table, the best sequence alignment can then be computed against the string of environment classes for a number of proteins.

This procedure initiated the so-called threading approach in inverse folding where the compatibility of candidate sequences with a given scaffold is examined. As can be anticipated from the discretization procedure, wherein the complexity of a 3D environment is mapped onto a limited number of classes, the success of the threading approach is significantly limited according to M. J. Sippl in *J. Comp.-Aided Mol. Design* (1993) 7:473-501 and Chiu et al. in *Protein Eng.* (1998) 11: 749-752.

Global sequence signatures involving many residues may be detected but, in view of its statistical nature, the threading method will not be applicable to accurately assess the sequence-structure compatibility implying e.g. perturbation effects wherein a given WT sequence is varied at a number of positions. In addition, even if a sequence is correctly predicted to be compatible with a given structure, the threading method itself is incapable of deriving an accurate 3D-structure of the sequence laid over a given protein backbone structure.

In order to achieve accurate predictions, it is desirable to take into account the full complexity of the 3D environment of each amino acid residue. In the third approach wherein predictions are based on computational methods assessing the energetic of a system of protein residues, it is possible to compute the conformation of lowest energy and even the sequence of lowest energy for a system consisting of a protein backbone and a set of amino acid residues which are allowed to vary in conformation and/or amino acid type. Most often, such computations are based on advanced search techniques combined with a detailed model for atomic interactions. In addition to the bonded and non-bonded interaction terms as used in molecular mechanics force fields (e.g. the CHARMM force field of Brooks et al. in *J. Comput. Chem.* (1983) 4:187-217), these energy computations may also assess the hydrophobic effect through a suitable solvation potential such as e.g. the pair-wise solvation potential disclosed by Street et al. in *Fold. Des.* (1998) 3:253-258, thereby correcting for the modeling in absence of explicit water molecules.

In order to determine whether a sequence is compatible with a given protein 3D-structure or scaffold, one could in principle explore different alignments of the query sequence relative to the given protein backbone and search for alignments yielding low conformational energy, if any. However such a process suffers from several inconveniences. First, this process is very time consuming, especially if the given query sequence has to be scanned against a large database of protein structures, thereby searching for the best scaffold that is likely to match with the given query sequence. Indeed, for each protein a series of detailed computations need to be carried out at the atomic level: several alignments need to be explored and each time the conformation or sequence of lowest energy must be identified, which involves the solution of the so-called combinatorial problem whereby the best solution must be found out of all possible combinations of single-residue states. Consequently it is unlikely that such computations can be carried out in a high-throughput mode. Second, the alignments must allow for gaps which are often located in the loop regions. However for evolutionary distant proteins the precise gap locations and lengths are a priori unclear, which in turn necessitates multiple trial runs to match one sequence with one structure.

In addition, some important problems simply cannot be answered by this third approach, such as for instance the task of computing all possible amino acid sequences that are compatible with a given protein scaffold (below a pre-set threshold, using a suitable scoring function), because it is at present impossible to generate all possible amino acid sequences and assess their compatibility within a reasonable computation time.

As a summary, there is a stringent need for a fundamentally new method in order to explore the sequence space that is compatible with a given scaffold and to rapidly scan for structural compatibility a given query sequence against a database of know protein structures.

GLOSSARY

Throughout the foregoing and following description of the invention, the abbreviations, acronyms and technical terms used shall have the following meanings and definitions:

ALA, ARG, ASN, ASP, CYS, GLN, GLU, GLY, HIS, ILE, LEU, LYS, MET, PHE, PRO, SER, THR, TRP, TYR, VAL: standard 3-letter code for the naturally occurring amino acids (or residues) named, respectively: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine.

| ASA: | Accessible Surface Area |
|---|---|
| DEE: | Dead-End Elimination |
| GMEC: | Global Minimum Energy Conformation |
| PDB: | Protein Data Bank |
| RMSD: | Root-Mean-Square Deviation |

Accessible Surface Area (ASA)

The surface area of (part of) a molecular structure, traced out by the mid-point of a probe sphere of radius ~1.4 Å rolling over the surface.

Amino Acid, Amino Acid Residue

Group of covalently bonded atoms for which the chemical formula can be written as $^+H_3N-CHR-COO^-$, where R is the side group of atoms characterizing the amino acid type. The central carbon atom in the main-chain portion of an amino acid is called the alpha-carbon ($C_\alpha$). The first carbon atom of a side chain, covalently attached to the alpha-carbon, if any, is called the beta-carbon ($C_\beta$). An amino acid residue is an amino acid comprised in a chain composed of multiple residues and which can be written as $-HN-CHR-CO-$.

Backbone

See: Main chain

Conformational Space

The multidimensional space formed by considering (the combination of) all possible conformational degrees of freedom of a protein, where one degree of freedom usually refers to the torsional rotation around a single covalent bond. In a broader sense, it also includes possible sequence variation by extending the definition of a rotamer to a particular amino acid type in a discrete conformation.

Dead-End Elimination (DEE)

A method to reduce the conformational space of a side-chain modeling task by eliminating individual side-chain rotamers which are incompatible with the system on the basis of one or more rigorous mathematical criteria. By a variant of this method, pairs of rotamers belonging to different residues can also be eliminated.

Energy Function, Force Field

The function, depending on the atomic positions and chemical bonds of a molecule, which allows to obtain a quantitative estimate of the latter's potential or free energy.

Flexible Side Chain, Rotatable Side Chain, Modeled Side Chain

A side chain modeled during performance of the method.

Global Energy

The total energy of a global structure (e.g. the GMEC) which may be calculated in accordance with the applied energy function.

Global Minimum

The globally optimal solution of a protein consisting of a number of elements (e.g. residue positions) which are a priori susceptible to variation (e.g. using the concept of rotamers).

Global Minimum Energy Conformation, GMEC

The global conformation of a protein which has the lowest possible global energy according to the applied energy function, rotamer library and template structure.

Global Structure, Global Conformation

The molecular structure of a uniquely defined protein, e.g. represented as a set of cartesian co-ordinates for all atoms of the protein.

Homology Modeling

The prediction of the molecular structure of a protein on the basis of a template structure.

Main Chain, Backbone

The part of a protein consisting of one or more near-linear chains of covalently bonded atoms, which can be written as $(-NH-CH(-)-CO-)_n$. Herein, the $C_\beta$-atom is considered as a pseudo-backbone atom and is included in the template because its atomic position is unambiguously defined by the positions of the true backbone atoms.

Protein Data Bank (PDB)

The single international repository for the processing and distribution of 3-D macromolecular structure data primarily determined experimentally by X-ray crystallography and nuclear magnetic resonance.

Protein Design

That part of molecular modelling which aims at creating protein molecules with altered/improved properties like stability, immunogenicity, solubility and so on.

Root-Mean-Square Deviation, RMSD

The average quadratic deviation between the atomic positions, stored in two sets of co-ordinates, for a collection of atoms.

Rotamer, Rotameric State

An unambiguous discrete structural description of an amino acid side chain, whether preferred or not. According to this definition, which is extended over the usual definitions by considering less preferred states, it is not required that rotamers be interchangeable via rotation only.

Rotamer Library

A table or file comprising the necessary and sufficient data to define a collection of rotamers for different amino acid types.

Rotamer/Template (Interaction) Energy

The sum of all atomic interactions, as calculated using the applied energy function, both within a given side-chain rotamer at a specific position in a protein structure and between the rotamer and the template.

Sequence Space

The multidimensional space formed by considering the combination of all (or a set of) possible amino acid substitutions at all (or a set of) residue positions in a protein.

Side Chain, Side Group

Group of covalently bonded atoms, attached to the main chain portion of an amino acid (residue).

Side-Chain/Side-Chain Pair(Wise) (Interaction) Energy

The sum of all atomic interactions, as calculated using the applied energy function, between two side-chain rotamers at two specific positions in a protein structure.

Steepest Descent Energy Minimization

Simple energy minimization method, belonging to the class of gradient methods, only requiring the evaluation, performed in accordance with a particular energy function, of the potential energy and the forces (gradient) of a molecular structure.

Template

All atoms in a modelled protein structure, except those of the rotatable side chains.

SUMMARY OF THE INVENTION

The present invention provides a totally new approach to handle sequence-to-structure and structure-to-sequence relationships:

(i) in a first aspect, the present invention comprises the systematical analysis of known protein structures in terms of individual contributions of single, pairs and occasionally also multiplets of amino acid residues to the global energy of a protein comprising any of these residues, and (ii) in a second aspect, the present invention comprises a method of combining the single, pair and multiplet contributions in order to estimate the global energy of a protein structure comprising a larger number of substitutions.

A main feature of the present invention is that energetic values for single, pairs and multiplets of residues in different conformations can be pre-computed once and stored on an appropriate data storage device for all, or a subset of all, known protein 3D-structures. These data can afterwards be retrieved from the storage device when needed for the calculation of global energies. The same data elements can be used over and again in various experiments wherein the compatibility of different sequences with the same 3D-structure is investigated. The present invention allows to (i) produce data in a fast and consistent way and (ii) use the produced data to calculate accurate global energies of proteins, which have undergone a relatively large number of mutations compared to the original structure.

A central idea of the present invention is to analyze known protein structures by computing a quantitative measure reflecting the energetic compatibility of all naturally-occurring and synthetic amino acids of interest at each residue position of interest in the structure. In a similar way, the energetic compatibility of selected residue pairs and multiplets may be computed as well. Upon generating such compatibility data, it is possible to take into account conformational adaptation effects for residues surrounding the considered substituted residue(s), as if the same substitutions were introduced in vitro by protein engineering techniques.

The said energetic compatibility data may be generated systematically for different protein structures and stored concisely using appropriate data storage devices. Ideally, it should be sufficient to use only pre-computed data for single residues and/or residue pairs in order to derive the compatibility of any sequence with a given protein structure with sufficient accuracy. In such case, it would become possible to derive extended lists of structure-compatible sequences as well as sequence-compatible structures arithmetically instead of by means of sophisticated protein modeling.

The present invention thus first provides a method for analyzing a protein structure, the method being executable in a computer under the control of a program stored in the computer, and comprising the following steps:

A. receiving a reference structure for a protein, whereby
the said reference structure forms a representation of a 3D structure of the said protein, and
the protein consists of a plurality of residue positions, each carrying a particular reference amino acid type in a specific reference conformation, and
the protein residues are classified into a set of modeled residue positions and a set of fixed residues, the latter being included into a fixed template;

B. substituting into the reference structure of step (A) a pattern, whereby
the said pattern consists of one or more of the modeled residue positions defined in step (A), each carrying a particular amino acid residue type in a fixed conformation, and the one or more amino acid residue types of the said pattern are replacing the corresponding amino acid residue types present in the reference structure;

C. optimizing the global conformation of the reference structure of step (A) being substituted by the pattern of step (B), whereby a suitable protein structure optimization method based on a function allowing to assess the quality of a global protein structure, or any part thereof, is used in combination with a suitable conformational search method, and the said structure optimization method is applied to all modeled residue positions defined in step (A) not being located at any of the pattern residue positions defined in step (B), and the pattern and template residues are kept fixed;

D. assessing the energetic compatibility of the pattern defined in step (B) within the context of the reference structure defined in step (A) being structurally optimized in step (C) with respect to the said pattern, by way of comparing the global energy of the substituted and optimized protein structure with the global energy of the non-substituted reference structure; and E. storing a value reflecting the said energetic compatibility of the pattern together with information related to the structure of the pattern in the form of an energetic compatibility object.

By "fixed" in step (A), it is meant that the template structure may be varied by at most about 1 Ångström in RMSD compared to the original structure.

For the purpose of the rotameric embodiment of the method, such as explained hereinafter, the selected rotamer library may be either backbone-dependent or backbone-independent. A backbone-dependent rotamer library allows different rotamers depending on the position of the residue in the backbone, e.g. certain leucine rotamers are allowed if the position is within an α helix whereas other leucine rotamers are allowed if the position is not in a α helix. A backbone-independent rotamer library uses all rotamers of an amino acid at every position, which is usually preferred when considering core residues, since flexibility in the core is important. However, backbone-independent libraries are computationally more expensive and thus less preferred for surface and boundary positions. The rotamer library may originate from an analysis of known protein structures or it may be generated by computational means, either on the basis of model peptides or specifically for the amino acids considered at each of said residue positions of said protein backbone.

For the purpose of step (C), the best possible global conformation of the protein system includes any conformation that can be appreciated by a person skilled in the art as being closely related to the optimum. For the purpose of step (E), storage of the data may be either explicit or implicit, the latter being accomplished e.g. by advanced data ordering or by conventional compression methods.

Other aspects of the present invention include:

a data structure comprising at least an ECO obtainable by the above-defined method, for instance in the form of a protein sequence which is different from any known protein sequence.

a nucleic acid sequence encoding a protein sequence analyzed by the method as above-defined.

an expression vector or a host cell comprising the nucleic acid sequence as above-defined.

a pharmaceutical composition comprising a therapeutically effective amount of a protein sequence generated by the method (as above-defined) and a pharmaceutically acceptable carrier.

a method of treating a disease in a mammal, comprising administering to said mammal a pharmaceutical composition such as above-defined a database comprising a set of ECO's in the form of a data structure, e.g. stored on a computer readable medium;

a computing device adapted to carry out any of the methods of the present invention;

a computer readable data carrier having stored thereon a computer program capable of carrying out any of the methods of the present invention.

The present invention, its characteristics and embodiments, will now be described with reference to the following detailed description.

BRIEF DESCRIPTION OF THE DRAWINGS

FIG. 4 shows the result of the alignment procedure of human alpha-lactalbumin [SEQ ID NO:12] against a single residue GECO profile for hen lysozyme [SEQ ID NO:1], according to the present invention; ten aligned fragments with a P-value below $10^4$ [SEQ ID NO:2] to [SEQ ID NO:1] were retained.

DETAILED DESCRIPTION OF THE INVENTION

As previously indicated, the present invention consists of two main aspects: first a new method including the ECO concept, secondly the use of such a method to assess the energy of global multiply substituted protein systems.

The first aspect of the present invention will be explained namely with reference to FIGS. 1 to 3 which are now described in detail.

Figure 1:
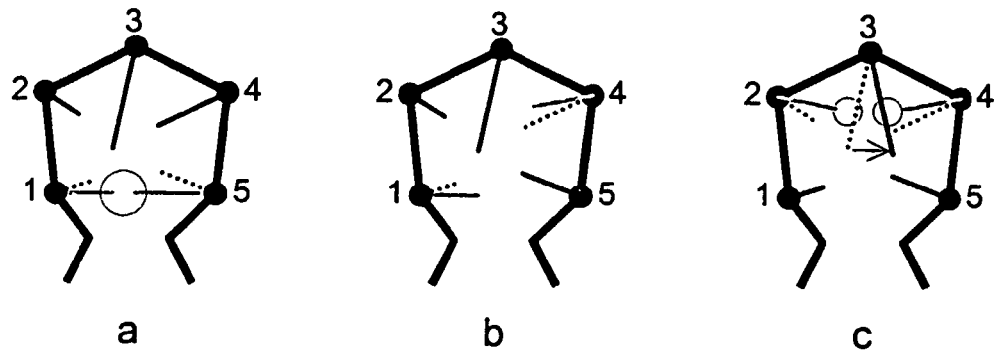
FIG. 1 shows three schematic representations of part of protein structures in their conformations of lowest energy.

In FIG. 1, the bold line symbolizes the backbone, whereas thin lines show residue side chains in their energetically optimal conformation. Residue positions are numbered from 1 to 5. Different residue types are represented by lines of different length. Black lines are used for the WT structure and grey lines show substituted residues. Dotted lines show residues before substitution or conformational adaptation. In FIG. 1a, residues 1 and 5 have been substituted by larger residue types. While each single substitution would be compatible with the remainder of the structure, the double mutation leads to an incompatibility situation (symbolized by the dotted circle), thus both mutations cannot be modeled independently. Conversely, FIG. 1b shows a situation wherein two mutations are assumed to be independent: the single substitutions at residues 1 and 4, as well as the double mutation do not change their environment and both residues do not significantly interact with each other. FIG. 1c shows that two residues which do not directly interact may still be coupled through conformational adaptation: the larger residue type at residue position 2 necessitates (dotted circle at left) a conformational change (indicated by an arrow) of residue 3 which is in conflict with residue 4 (dotted circle at right).

Figure 2:
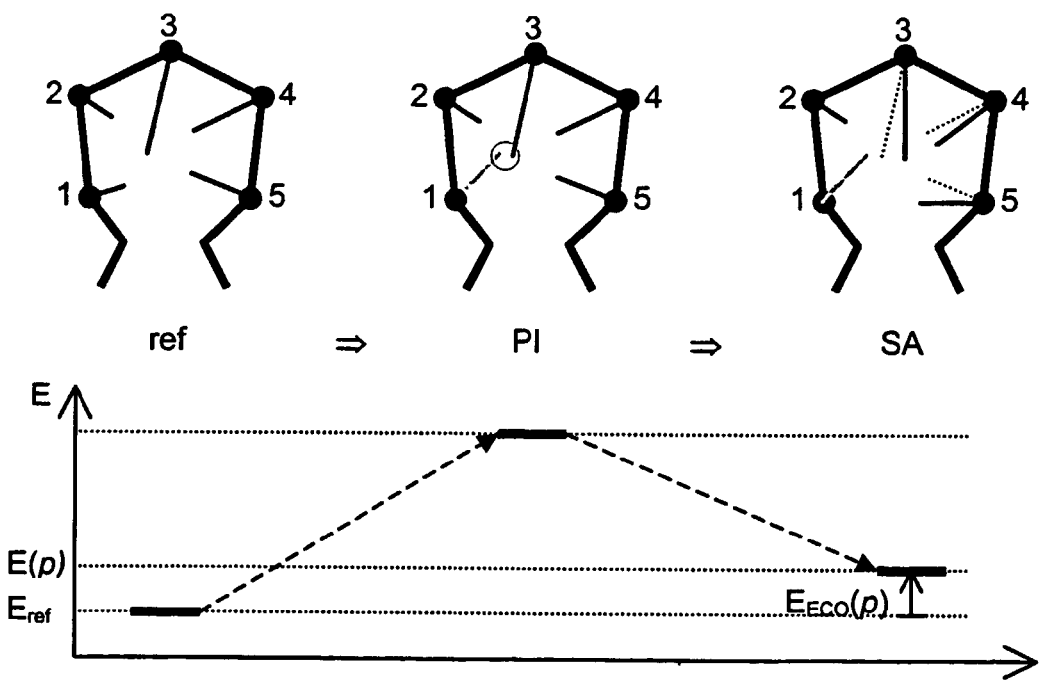
FIG. 2 shows a schematic representation of the mechanism of pattern introduction (PI) and structure adaptation (SA) according to the present invention.

In FIG. 2, the same notations are used as in FIG. 1. The left-most drawing represents the protein of interest in its reference structure (ref). The middle drawing shows the reference structure wherein a single residue pattern p is introduced at residue position 1. The dotted circle illustrates a sterical conflict with residue 3. After the SA step (right-most drawing), residues 3, 4 and 5 have rearranged from their reference state (dotted lines) to a new, adapted conformation (full lines) which overcomes the said sterical conflict. The energy of each of these structures is represented underneath each drawing, showing that the introduction of p into the reference structure first leads to a high-energy "intermediate" structure which can be relaxed towards a structure of lower energy. The difference between the energy of the reference structure, $E_{ref}$, and that of the substituted and adapted structure, $E(p)$, is the ECO energy, $E_{ECO}(p)$, which can be considered as a substitution energy.

Figure 3:
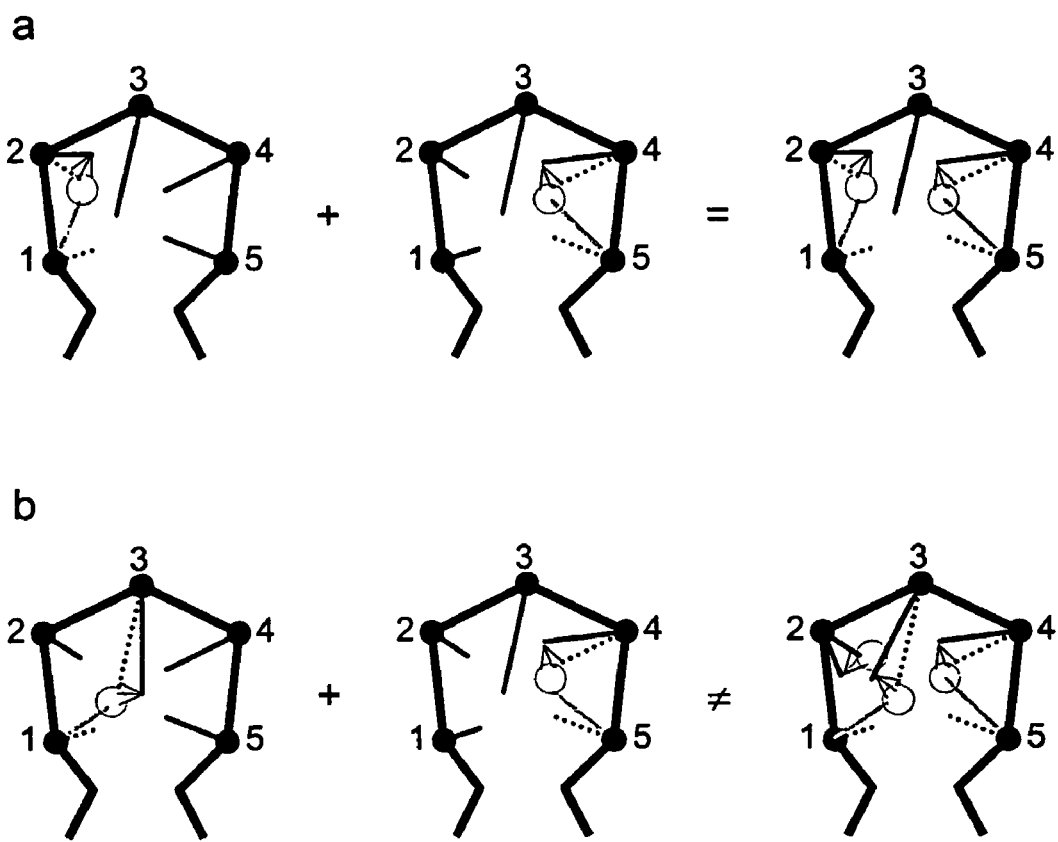
FIG. 3 illustrates the principle of additivity of adaptation (AA) according to the present invention.

In FIG. 3, the same notations are used as in FIG. 1. FIG. 3a shows an example wherein the AA principle is met, i.e. the same conformational adaptations (symbolized by the arrows) are observed for the double substitution (at right) as are occurring for both single substitutions (at left). FIG. 3b shows an example wherein the AA principle is not met.

Before describing the ECO concept and its possible applications, the following prerequisites should be explained:
1. a definition of applicable protein structures (see STRUCTURE DEFINITION);
2. a definition of conformational freedom (see CONFORMATIONAL FREEDOM);
3. a description of applicable energy models (see ENERGY FUNCTION);
4. a description of preferred modeling techniques which are able to generate an ECO (see STRUCTURE OPTIMIZATION); and
5. a definition of a reference structure, its relevance and some preferred options (see REFERENCE STRUCTURE).

Next, the ECO concept is discussed in detail, both descriptively (see DESCRIPTION OF THE ECO CONCEPT) and mathematically (see FORMAL DESCRIPTION OF ECO). Then, a preferred approach to systematically derive ECO's is discussed (see SYSTEMATICAL PATTERN ANALYSIS (SPA) MODE). Next, some preferred operations on basic ECO's are elaborated (see GROUPED ECO'S). Finally, a preferred method to estimate the energy of multiply substituted protein structures from single and double ECO and/or GECO energies is described (see ASSESSING GLOBAL ENERGIES FROM SINGLE AND DOUBLE (G)ECO's).

Structure Definition

The present method to generate ECO's is applicable to protein molecules for which a 3D representation (or model or structure) is available. More specifically, the atomic coordinates of at least part of a protein main chain, or backbone, must be accessible. Preferably a full main chain structure and, more preferably, a full protein structure is available. In the event that the available protein structure is defective, some conventional modeling tools (e.g. the so-called spare parts approach disclosed by Claessens et al. in *Prot. Eng.* (1989) 2:335-345 and implemented e.g. by Delhaise et al. in *J.Mol. Graph.* (1984) 2:103-106, or other modeling techniques such as reviewed by Summers et al. in *Methods in Enzymology* (1991) 202:156-204?) may be applied to build missing atoms or loops. Depending on the force field used (see ENERGY MODEL), the coordinates of at least the heavy atoms (any atom other than hydrogen), or heavy atoms together with polar hydrogen atoms, or all atoms, of at least a region around the amino acid residues of interest must be known, where the said region should be sufficiently large to enable accurate energetic computations. Optionally ligands, such as co-factors, ions, water molecules and so on, or parts thereof may be included in the definition of the protein structure as well. A known structure for the side chains of a protein of interest is not an absolute requirement since the method of the present invention includes a side-chain placement step. However, knowing starting coordinates for the said side chains may be useful when the user should decide to energy-minimize the starting structure or to keep some side chains in a fixed conformation.

The origin of the 3D protein structure is relatively unimportant within the context of the present invention since the ECO concept remains applicable to any 3D-structure conforming to aforementioned criteria. Yet, the meaningfulness of generated ECO's (and, therefore, the usefulness of applications derived therefrom) is directly proportional to the quality (accuracy) of the starting structure. Therefore, a number of possible sources of atomic coordinates, in decreasing order of preference, are provided hereinafter: X-ray determined structures, NMR-determined structures, homology modeled structures, structures resulting from de novo structure prediction.

In the preferred embodiment of the present invention, some atoms—generally referred to as "template atoms"—may be kept fixed throughout the process of generating ECO's. Preferably, a template consists of all main-chain atoms, $C_\beta$-atoms and ligand atoms. A useful but more delicate option is to include particular side chains into the template, preferably side chains lying far enough (as determined by a skilled user) from the residue(s) involved in the ECO generation.

The starting 3D-structure of a protein of interest forms a first source of input data for the performance of the present method.

In the definition of a protein of interest, there are no limits to the length of the chain (provided that at least two amino acids are linked together) or to the number of chains. The definition of a protein as used herein also includes domains (e.g. functional, enzymatic or binding domains) as well as smaller fragments such as turns or loops. By extension, the method may also be applied to molecules such as peptides, peptidomimetic structures and peptoids.

With respect to the second aspect of the present invention, i.e. a method to assess the energetic fitness of multiply substituted proteins on the basis of values for single residues and pairs, a starting structure is of lesser importance. Indeed, the latter method preferably uses pre-computed values from a database, rather than generating them when needed, although the latter possibility is not excluded by the present invention.

Conformational Freedom

The present method involves two different types of structure changes, i.e. amino acid substitutions and conformational changes, the latter being discussed in this section. The present method to generate ECO's can be executed by allowing conformational changes either (i) in a discrete rotameric space or (ii) in a continuous space. The rotameric approach being preferred will be described first.

The concept of rotamers states that protein side chains (and even residue main chains) can adopt only a limited number of energetically favorable conformational states, called rotamers, according to Ponder et al. in *J. Mol. Biol.* (1987) 193:775-791. The attractive aspect of rotamers is that the theoretically continuous conformational space of amino acid residues can be transformed into a discrete number of representative states on the basis of a rotamer library (for instance the rotamer library described by De Maeyer et al. in *Fold. & Des.* (1997) 2:53-66, comprising 859 elements for the 17 amino acids having rotatable side chains), thus considerably facilitating a thorough, systematical analysis of a protein structure. Furthermore, some energetic properties of individual rotamers within the context of a given protein structure can be pre-calculated before any modeling action takes place. The same can be done for pairwise interaction energies between rotamers of different residues. On the basis of individual (or "self") and mutual (or "pair") energies, a large number of rotamers and rotamer combinations can be identified as being incompatible with the scaffold of the protein of interest. Another major advantage of the rotamer concept is that search methods are known in the art to find the energetically best possible global structure for the side chains of a protein, given a fixed main chain, a rotamer library and an energy function. Examples of such methods known in the art are the various embodiments of the DEE method such as disclosed by Desmet et al. in *Nature* (1992) 356:539-542, Lasters et al. in *Protein Eng.* (1993) 6:717-722, De Smet et al. in *The Protein Folding problem and tertiary structure prediction* (1994) 307-337, Goldstein in *Biophys. Jour.* (1994) 66:1335-1340 and De Maeyer et al. (cited supra). Irrespective of the search method, the use of rotamers allows to overcome local energetic barriers by simply switching between different rotameric states.

Furthermore, it should be noted that ECO's refer to the structural compatibility of "patterns" that are grafted into a given protein structure. As used herein, a pattern consists, at the choice of the user, of one or more residue positions, each carrying an amino acid type in a certain conformation. Pattern residues need not be covalently linked to each other, but they must be intact (at least the whole side chain must be considered) and their 3D-structure must be unambiguous. In the preferred embodiment of the present invention, different ECO's may be generated, where each ECO is an energetic compatibility object defined on one or more residue positions, each having assigned a specific amino acid type and adopting a well-defined rotameric state.

The selection of rotamers occurs on the basis of a rotamer library, for instance according to one of the three following possibilities: (i) the retrieval of side-chain rotamers from a backbone independent library, (ii) the retrieval of side-chain rotamers from a backbone dependent library and (iii) the retrieval of combined main-chain/side-chain rotamers from a backbone dependent library. The two former possibilities necessarily imply that the main-chain structure of a pattern residue is taken from the protein starting structure. The latter possibility requires an additional comparison between the local backbone conformation in the protein structure and all backbone conformations in the library and the retrieval of a side-chain rotamer associated with the closest matching backbone conformation and is therefore more complicated since it involves the insertion of the main-chain portion of the rotamer selected from the library with the backbone of the protein structure. This can be performed in many ways. For instance for isolated pattern residues, it is possible to apply a least-squares fitting of the peptide plains determined by the main-chain dihedral angles of the selected library rotamer onto those of the protein structure where the rotamer is to be inserted. For consecutive pattern residues (e.g. loops), the method described in Brugel (Delhaise et al. in J. Mol. Graph.

(1984) 2:103-106) can be used. In both cases, the method may be followed by an energy refinement step using a gradient method, e.g. a steepest descent energy minimization. A common feature of the three possible selection methods is that they result in a unique definition of the 3D structure of each pattern residue, their side-chain conformations are selected from a rotamer library whereas their main-chain conformations are taken either from a library or from the protein starting structure.

Another aspect of the present invention concerns the conformational freedom of that part of the protein not belonging to the pattern of interest, i.e. the "pattern environment". In this respect, the present method includes a step wherein the pattern environment is conformationally adapted to the pattern itself and which essentially aims at an energetical optimization of intramolecular interactions within the pattern environment and between the latter and the pattern atoms. Thus, we shall make a distinction between a rotameric and a non-rotameric embodiments, both subject of the present invention, since they have quite different characteristics. In the preferred rotameric embodiment, the accessible conformational freedom of the pattern environment is determined by a rotamer library. Similarly to pattern residues, the rotamer library used for the non-pattern residues may be either a side-chain or a combined main-chain/side-chain rotamer library. However, restricting the conformational space of the non-pattern residues to only side-chain rotamers (thus keeping fixed the main chain) is highly preferred because of its mathematical simplicity.

In contrast to the assignment of one unique rotameric conformation to each of the pattern residues, the residues of the pattern environment have in principle access to all rotameric states known in the library for the associated residue types. The total conformational space is then defined as all possible combinations of rotamers for the non-pattern residues. The search method described in the section STRUCTURE OPTIMIZATION below then needs to find the energetically most favorable combination.

As will be appreciated by those skilled in the art, several techniques can be applied to restrict the number of rotamers for individual residues in a protein structure, based on criteria related to local secondary structure, local energy, solvent accessibility and so on. In addition, some residues of the pattern environment may be completely refrained from adaptation (this is equivalent to include such residues into the template, see STRUCTURE DEFINITION) in order to speed up computations. This however may lead to underestimate the structural compatibility of the pattern of interest. The user therefore has to decide whether the induced level of error remains acceptable in the application concerned. For example in a fold recognition application, where the compatibility of a long amino acid sequence with different protein folds is to be assessed, many single residues may be erroneously predicted as incompatible if the global score for a correct or "true" sequence-structure correlation remains distinguishable from the incorrect or "false" matches. It may even be preferred to generate ECO's while limiting adaptation to only those residues in immediate contact with the pattern residue(s). To the contrary, should a user be interested to test whether a given pattern (e.g. the binding site of a receptor, or any part thereof) can be designed into a scaffold of interest, then it is advisable to eliminate as many sources of error as possible and therefore to retain a high number of adaptive residues around the said pattern. As a general rule, it is suggested to apply one of many possible threshold-based methods directly or indirectly related to the distance between pattern and environment residues. For example a convenient criterion may be to include in the set of adaptive residues all residues j for which $$\min_i D(i,j) < S + n(i^a) + n(j^b) \quad (eq.1)$$

where i is a pattern residue, j is an environment residue, $D(i,j)$ is preferably equal to the distance between the $C_\beta$-atoms of i and j in the protein structure, $\min_i D(i,j)$ is the closest such distance for all pattern residues i, S is a predefined threshold value (preferably about 6 Å but possibly lower or higher values for less or more critical applications,. respectively), $i^a$ and $j^b$ are the residue types at positions i and j, respectively, and $n(i^a)$ and $n(j^b)$ are measures of the size of the side-chains at the respective positions i and j, where n is preferably equal to the number of heavy atoms (i.e all non-hydrogen atoms) counted from the $C_\beta$-atom (included) along the longest branch in the side chain. For example, if $i^a$=Ile, $j^b$=Phe and S=6 Å, j would be included in the set of adaptive residues if $D(i,j)<6+3+5=14$ Å.

Although less preferred, the present method to generate ECO's can also be performed without using the rotamer concept. Again a distinction needs to be made between the pattern residues and the pattern environment. With respect to the conformation of the one or more pattern residues, a first approach is to "copy" a sub-structure from a known 3D-structure and to graft it into the structure of the protein of interest using a suitable structure fitting method. This can be of interest, for example, in loop grafting or when attempting to substitute binding site patterns. This fully matches the ECO concept since the definition of a pattern requires establishing a well-defined set of residue positions (e.g. a loop fragment), carrying a well defined amino acid sequence (one residue type at each position) in a well-defined conformation (e.g. a known conformation). An alternative to assign a conformation to pattern residues is to randomly sample it from a continuous torsion space around main-chain and/or side-chain dihedral angles using a random number generator. This approach does form a feasible alternative to investigate the compatibility of different patterns occupying the same residue positions and types while adopting different non-rotameric conformations.

The non-pattern residues form the subject of the second step of the present method, i.e. the adaptation step. Here also, a less preferred but feasible non-rotameric approach is possible. The structural adaptation of the pattern environment in a continuous conformational space will be driven by the selected optimization method, typically a gradient method, in combination with the selected energy function, typically a potential or free energy function. Here, the accessible space is in principle nearly infinite since it includes all possible combinations of continuous torsion variations with bond angle bending, bond stretching, and so on. However, in practice, most continuous optimization methods (such as e.g. steepest descent energy minimization) do cause only local changes in the structure and are prone to get trapped into local optima instead of the global optimum. On the other hand, gradual non-rotameric optimization methods advantageously provide a simple solution to the problem of main-chain flexibility because during structural optimization of a pattern environment, the protein main-chain can be optimized together with the side chains.

In conclusion, both a rotameric and non-rotameric method are suitable for both pattern definition and adaptation of the pattern environment. Although all combinations are possible and useful in particular circumstances, particularly preferred are the combination of rotameric patterns with non-rotameric adaptation as well as combinations of rotameric adaptation with rotameric or non-rotameric patterns of interest.

Energy Function

The most important element of an ECO is its energy value, which should be interpretable as a quantitative measure of the structural compatibility of the ECO pattern within the context of the adapted protein structure. For this reason, the notion of "structural compatibility" may be considered equivalent to "energetic compatibility".

In principle, the method of the present invention may be performed with all energy functions commonly used in the field of protein structure prediction, provided that the applied energy model allows to assign an energetic value that is a pure function of the atomic coordinates, atom types and chemical bonds in a protein structure, or any part thereof. When considering rotamers it is preferred, although not required, that the energy function be pair-wise decomposable, i.e. the total energy of a protein structure can be written as a sum of single and pair-residue contributions (see equation 4 below), in order to facilitate the adaptation step in the generation of ECO's.

Preferably, the applied energy model should approximate as close as possible the true thermodynamic free energy of a molecular structure. Therefore, the applied energy function should include as many relevant energetic contributions as possible, depending on the accuracy requirements of the user. Highly preferred energy functions include terms which account for at least Van der Waals interactions (including a Lennard-Jones potential such as disclosed by Mayo et al. in *J. Prot. Chem.* (1990)), hydrogen bond formation (such as referred by Stickle et al. in *J. Mol. Biol.* (1992) 226:1143), electrostatic interactions and contributions related to chemical bonds (bond stretching, angle bending, torsions, planarity deviations), i.e. the conventional potential energy terms. Useful energy models including such contributions are, for example, the CHARMM force field of Brooks et al. (cited supra) or the AMBER force field disclosed by Weiner et al. in *J. Am. Chem. Soc.* (1984) 106:765.

In addition to these potential energy terms, some other energetic contributions may be important, given the fact that different ECO's may involve different residue types of varying size and chemical nature, placed at topologically different positions in a protein structure. Four types of energetic contributions and corrections may account for type- and topology-dependent effects: corrections for (1) main-chain flexibility, (2) solvation effects, (3) intra side-chain contributions and (4) the behavior of particular residue types in the unfolded state.

Main-chain flexibility, or adaptability of the backbone to an inserted pattern, can be corrected by reducing the sensitivity of the terms related to packing effects, e.g. using methods including united-atom parameters such as disclosed by Lazar et al. In *Protein Sci.* (1997) 6:1167-1178 or re-scaling of atomic radii such as proposed by Dahiyat et al. *Proc. Natl. Acad. Sci. USA* (1997) 94: 10172-10177. When generating ECO's using a gradient method in the adaptation step, main-chain variability is automatically taken into account by including the corresponding atoms in the optimization process.

Because of the hydrophobic effect, solvation effects may be a crucial factor determining the reliability of modeled protein structures. According to the present invention, computing explicit protein-solvent interactions is not preferred since this is prohibitively slow. Instead, a compromise between computational performance and prediction accuracy is a method wherein the burial and exposure of polar and non-polar atoms is translated into energetic correction terms for solvation on the basis of their buried and exposed surface areas and of a set of atom type-specific solvation parameters, such as reviewed by Gordon et al. in *Curr. Opin. Struct. Biol.* (1999) 9:509-513. In the embodiment of the present invention wherein the adaptation step in the ECO generation occurs in a rotameric way, it is beneficial to have a pair-wise decomposable solvent function, such as proposed by Street et al. (cited supra). Also preferred for its computational efficiency is a method for the assignment of a set of energetic solvation terms to each of the considered residue types (usually the 20 naturally-occurring amino acids) depending on the degree of solvent exposure of their respective rotamers at the considered residue positions in the protein structure of interest. This method is hereafter referred to as the type-dependent, topology-specific solvation (TTS) method. In this method, a set of N_TYPES energetic parameters is established for each of N_CLASSES different classes of solvent exposure, where N_TYPES is the number of residue types considered (usually 20) and N_CLASSES is the number of discrete classes of solvent exposure. For example, three such classes may be established, corresponding with buried, semi-buried and solvent-exposed rotamers, respectively. It is noteworthy that different rotamers for the same residue type at the same position may be assigned different classes. Both the number of classes and their boundaries may be subject to variation, but the following embodiment should be preferred:

first, each pattern element (a given residue type at a given residue position in a specific rotameric state) is substituted into the protein structure and its accessible surface area (ASA) is calculated, for instance according to Chothia in *Nature* (1974) 248:338-339, next, a class assignment occurs on the basis of the percentage ASA of the residue side chain in the protein structure compared to the maximal ASA (over all rotamers) of the same side chain being shielded from the solvent only by its own main-chain atoms, for instance the class of buried rotamers may be defined by ASA %<5%, the class of semi-buried rotamers by 5%≦ASA %<25% and the class of solvent-exposed rotamers by 25%≦ASA %, and finally an appropriate type- and topology-specific energy, $E_{TTS}(T,C)$, for the considered pattern element is retrieved from a table of TTS values, using the pattern type (T) and class (C) indices.

The TTS energy thus obtained should be added as an extra term to the energy of the pattern element in the protein structure (see FORMAL DESCRIPTION OF ECO'S).

A table of TTS values may be established by tuning the different TTS parameters $E_{TTS}(T,C)$ versus a heuristic scoring function S as follows. The tuning method includes:

first considering a set of a number of, preferably at least 50, well-resolved protein structures and assigning to each residue position of this set a unique index i (1≦i≦all residues), then considering, at each residue position i, all residue types a in all rotameric states r, thereby forming the set of all possible position-type-rotamer combinations $i_r^a$, defining by $i_r^w$ the WT residue type at position i in a rotameric state r as observed in the protein comprising position i, assigning to each $i_r^a$ a solvent exposure class $C(i_r^a)$ as described above, calculating for each $i_r^a$ the value $E_{pot}(i_r^a)$ as the total potential energy the rotamer $i_r^a$ experiences within the fixed context of the protein structure comprising i, preferably using conventional potential energy terms such as disclosed above, defining a function ΔE(i) as $$\Delta E(i) = \min_r(E_{pot}(i_r^w) + E_{TTS}(w, C(i_r^w))) - \min_a \min_r(E_{pot}(i_r^a) + E_{TTS}(a, C(i_r^a))) \quad (eq.2)$$

ΔE(i) being interpretable as the difference in energy of the WT residue type in its best possible rotamer (as obtained by the $\min_r$ operator) and the energetically most favorable residue type at residue position i also in its best possible rotamer (as obtained by both the $\min_a$ operator and the $\min_r$ operator), given a (as yet undefined) set of TTS parameters, and applying a suitable parameter optimization method to maximize S by varying $E_{TTS}(T,C)$ parameters.

If the TTS parameters are zero, then equation (2) provides the difference in potential energy between the optimal WT rotamer and the energetically most favorable residue type at position i in its optimal rotameric state, within the context of the protein structure involved. The effect of assigning non-zero values to the TTS parameters is that the energy of a residue will be modified by its associated type- and topology-dependent correction term. In the ideal case, the TTS-parameters may be such that, at each position i, the observed WT residue becomes or approximates the energetically optimal residue type. In order to reach this objective, the objective scoring function S defined by the following equation (3)

$$S = \Sigma_i (1 + \Delta E(i))^{-1} \quad (eq.3)$$

may be used, which means that if at position i the WT residue type is best (i.e. ΔE(i)=0), then S is increased by one unit. For instance, if the WT would be 1 kcal. mol$^{-1}$ higher in energy than the best possible type, this would result in an increase of S by 0.5 unit.

Finally, It has been observed that the function S as defined by equation (3) on 60 TTS parameters (20 types×3 classes) is easy to optimize by simply taking steps above and below the current value of each parameter and accepting only up-hill changes (i.e. better values) in S. Initial parameters may be set to zero and initial steps are preferably about 10 kcal mol$^{-1}$, gradually reducing in size by about 75% per optimization round until a step size of about 0.05 kcal mol$^{-1}$ is reached, which terminates the parameter optimization process.

The same strategy of parameter tuning may lead to even more relevant results if the potential energy calculations, $E_{pot}(i_r^a)$, are performed within the context of an adaptive protein structure rather than a fixed structure. This can be accomplished e.g. by using one of the structure optimization methods described in the next section. Moreover, such approach is fully consistent with the ECO concept itself, wherein the compatibility of patterns is evaluated in an adaptive environment. A set of TTS contributions derived in this way is shown in table 3.

A most attractive feature of the TTS method is that terms used therein will automatically account for two other effects which may be critical in the field of protein design. The first effect is the mutual bias of different residue types when comparing their intraside-chain energies. For example, an arginine residue may have an energetic advantage over a chemically similar lysine residue by more than 5 kcal mol$^{-1}$ (using the CHARMM force field) which is solely due to intraside-chain contributions. In order to correct for this phenomenon in the prior art, such contributions may be simply switched off or corrected for by subtracting a reference energy calculated as the potential energy of an isolated amino acid residue, according to Wodak (cited supra). However, the present invention prefers not to impose any a priori intraside-chain correction, but to incorporate this into the TTS contributions. The second effect relates to energetic aspects of the unfolded state, which is ignored when computing energies exclusively from the folded state of the protein. This involves complicated elements like changes in entropy, residual secondary and tertiary structure in the unfolded state, the existence of transient local and global states, and so on. Consequently, in a modeling environment where native, folded structures are examined, it is extremely difficult to predict the impact of such effects on the predictions. However, in as far as such effects would be type- and topology-dependent, it may be assumed that the TTS method implicitly takes them into account. For example, buried leucine residues may experience a greater loss in torsional entropy compared to isoleucine upon folding of the protein in view of the fact that the latter is beta-branched.

In conclusion, the present method for generating ECO's requires a suitable energy function including as many relevant contributions as possible, preferably functions based on interatomic distances and bond properties. There is no specific preference with respect to explicit treatment of hydrogen atoms or not. The implementation of the aforementioned TTS method will be useful when ECO's are prepared for fold recognition or protein design, as well as for other applications.

Structure Optimization

When generating ECO's, a practical and reliable method for structure optimization is needed, i.e. a search method producing an optimal or nearly optimal 3D structure for a protein molecule, given the starting structure of the protein as previously described in STRUCTURE DEFINITION, the introduction of one or more substitutions according to the pattern of interest (except for the reference structure described in the section REFERENCE STRUCTURE below), the allowed conformational variation of the protein system as previously described in CONFORMATIONAL FREEDOM and the applied energetic model as described in ENERGY FUNCTION.

ECO's are intended to measure the change in total energy when non-native patterns are introduced in the context of a protein structure, i.e. an ECO energy is actually a differential value between the total energy of a substituted protein structure and that of a native or "reference" protein structure. Both the substituted and the reference structures should be modeled in a similar and reliable way in order to allow for interpretation of an ECO energy as a measure of the true substitution energy associated with the pattern of interest. Therefore the method should guarantee that both the substituted and the non-substituted protein structures approximate as close as possible the structures as may be determined experimentally.

Assuming a nearly constant backbone conformation may be a source of error for the most constrained substitutions: proteins comprising complicated substitutions may reorganize their backbone conformation or may even completely unfold. In such cases, ECO substitution energies predicted according to the present invention may be in error, but should not change the conclusion that such substitutions are probably incompatible with the protein backbone.

The present invention has no preference with respect to the structure optimization (or search) method used as long as it provides a beneficial ratio of prediction accuracy versus computational speed. Suitable known search methods include, for example, Monte Carlo simulation such as disclosed by Holm et al. in *Proteins* (1992) 14:213-223, genetic algorithms such as disclosed by Tufféry et al. in *J. Comput. Chem.* (1993) 14:790-798, mean-field approaches such as disclosed by Koehi et al. in *J. Mol. Biol.* (1994) 239:249-275, restricted combinatorial analysis such as disclosed by Dunbrack et al in *J. Mol. Biol.* (1993) 230:543-574, basic molecular mechanics gradient methods such as described in Stoer et al. in *Introduction to Numerical Analysis* (1980), Springer Verlag, New York and DEE methods such as previously disclosed. In the preferred embodiment of the present invention wherein the conformational freedom of individual residues is represented by rotamers, a yet unknown structure optimization method is however preferred over the previously known methods because it combines a high accuracy together with a high intrinsic computational efficiency. This combined characteristics is important especially in the systematical pattern analysis (SPA) embodiment of this invention wherein typically hundreds of thousands of patterns per protein need to be analyzed. This method, hereinafter referred as the FASTER method, is a method for generating information related to the molecular structure of a biomolecule (e.g. a protein), the method being executable by a computer under the control of a program stored in the computer, and comprising the steps of (a) receiving a 3D representation of the molecular structure of said biomolecule, the said representation comprising a first set of residue portions and a template;

(b) modifying the representation of step (a) by at least one optimization cycle; characterized in that each optimization cycle comprises the steps of:

(b1) perturbing a first representation of the molecular structure by modifying the structure of one or more of the first set of residue portions;

(b2) relaxing the perturbed representation by optimizing the structure of one or more of the non-perturbed residue portions of the first set with respect to the one or more perturbed residue portions;

(b3) evaluating the perturbed and relaxed representation of the molecular structure by using an energetic cost function and replacing the first representation by the perturbed and relaxed representation if the latter's global energy is more optimal than that of the first representation; and (c) terminating the optimization process according to step (b) when a predetermined termination criterion is reached; and (d) outputting to a storage medium or to a consecutive method a data structure comprising information extracted from step (b).

In short, this method works by repeated, gradual optimization of rotameric sets of residues. When the protein system is near its globally optimal structure, which is the case if small patterns (e.g. one or two residues) are substituted into a reference structure, only a small number of optimization rounds are needed to obtain the optimally relaxed structure. This process typically takes in the order of about 10 to 100 milliseconds CPU time per pattern analysis (using a 300 MHz R12000 processor as a reference). The computation of the reference structure itself typically requires about 100 to 1000 CPU-seconds per protein structure.

Reference Structure

The reference structure is defined as the structure of lowest energy for the protein of interest, given an experimentally determined or computationally generated starting structure, a particular rotamer library (only in the rotameric embodiment of the present invention) and a selected energy function and may be obtained by a suitable search method (see STRUCTURE OPTIMIZATION).

The role of the reference structure is to make an ECO energy (the value computed in step F) interpretable as a substitution energy. ECO's are generated by substituting a non-native pattern into an optimally relaxed reference structure, reconsidering (in the structure adaptation step) the optimal packing arrangement and computing the difference in global energy between the modified and the original reference structure.

An important feature of the reference structure is its amino acid sequence. For instance, the protein of interest may be modified prior to computing its structure of lowest energy by supplying the backbone with new side chains. Thus, the user of the method may define a reference sequence which is different from the sequence observed in the starting structure of the protein. Either a few amino acid side chains or the complete amino acid sequence may be altered. The reference structure is then the conformation of lowest energy for the protein of interest having a user-selected reference amino acid sequence. The most ready reference sequence is the native amino acid sequence of the protein starting structure, but valuable alternatives thereto will be explained hereafter.

The reference sequence should preferably approximate as close as possible the sequences that will be generated in an ECO-based application. For example, when interest is in thermally stabilizing mutants of a given enzyme of known sequence but unknown structure, and assuming that only a distantly related homologous 3D-structure would be available from a database of protein structures, then it is advisable to compute the structure of lowest energy for the sequence of said enzyme (e.g. using the homologous backbone structure) rather than for the sequence of the homologous protein (using its own backbone structure). If the mutants of the said enzyme were built from ECO's generated for the homologous structure, this would involve many more individual changes (and potential sources of error) as compared to when the enzyme mutants are built with ECO's generated with the modeled enzyme sequence as a reference structure.

However protein design and fold recognition applications may also rely on some general purpose databases of ECO's derived from representative protein structures or scaffolds. Furthermore, it is not an absolute requirement to use any known or existing reference amino acid sequence when generating ECO's. A most interesting type of reference sequence may be the sequence leading to the lowest possible energy for the protein of interest, in other words the global minimum energy sequence which may be computed by any suitable search method such as previously described (see STRUCTURE OPTIMIZATION), e.g. a DEE method or the FASTER method. Some other reference sequences, such as a polyglycine or a polyalanine sequence, may provide practically useful reference structures. They provide the advantage that the adaptation step in the ECO computation is easier, but the disadvantage that the ECO patterns are modeled onto an almost naked backbone. Finally, we observed experimentally that assessing multiply substituted proteins from single and double ECO's is surprisingly insensitive to the nature of the reference sequence, especially in applications which tolerate some level of approximation (like fold recognition). Therefore any possible reference sequence, including randomly generated and dummy sequences, may be practically useful in particular cases. Selecting a reference sequence forms an essential part of generating an ECO since it directly relates to the interpretation of the associated energy value as being a substitution energy.

Description of the ECO Concept

An "energetic compatibility object" (ECO) is an object which basically provides a fully structured description of the results of a modeling experiment wherein a given pattern p of interest has been introduced and modeled into a protein reference structure. Usually the pattern p consists of a small number of amino acid residue types, each being placed at a specific residue position in the reference structure and adopting a well-defined fixed conformation. In a preferred embodiment of the present invention, hereinafter referred as the "systematical pattern analysis" (SPA) mode, a large number of predefined patterns may be generated and analyzed whithin the context of the reference structure. The SPA mode is particularly suited to obtain large-scale results concerning the mutability of single and pairs of residues. It also provides the necessary input data for the analysis of multiply substituted proteins on the basis of elementary data components.

The number of residues of p is usually 1 or 2 but larger patterns of interest, comprising e.g. a set of clustered core residues, may be considered as well. In general, the present invention does not impose restrictions to the number of residues included in p since by definition p is a pattern of interest to the user. However, in the preferred SPA mode, where ECO's are systematically generated for many different patterns, the number of residues of any such pattern may preferably be limited to 1 or 2.

Besides the number of residues, an unambiguous description of p also requires establishing the exact locations of the one or more residues of p within the framework of the reference structure. In the present invention the allowed locations correspond with amino acid residue positions, which means that the said locations are defined by selecting, for each pattern residue, a specific amino acid residue position of interest. All conventional amino acid residues which are present in the protein reference structure are valid positions, irrespective of whether they are chemically modified or cross-linked to other residues. Conversely, atoms or molecules not belonging to a protein or peptide, known in the art as ligands, are not considered as valid positions. In the case of patterns consisting of more than one residue, some further rules apply as follows. Any two residues of the same pattern p should not occupy the same position. Also, as will be appreciated by those in the art, it may be desirable to consider only patterns for which the residue positions are proximate in space since very distant residues are likely to be independent. However this is preferred only when (i) a large number of different patterns has to be examined and computational speed is a limiting factor, and (ii) the condition of independence and the related criterion of proximity have been statistically verified. In the preferred SPA mode of implementation of the invention, the residue positions of interest may be determined by the region in the protein reference structure which is of interest to the user. If the interest is e.g. in stabilizing a protein, only core residues may be taken into account and a set of patterns may be systematically defined for all single core residues as well as all possible pair-wise combinations thereof.

A further aspect of the present invention is the chemical nature of the one or more residues of p which may be validly considered at the selected positions in the reference structure. According to the invention, all naturally-occurring and synthetic amino acid types may be included in the set of valid residue types. The choice of these residue types is basically unrelated to the amino acid sequence of the reference structure. If a residue type of p differs from the residue type in the reference structure at the selected position, this actually corresponds to a mutation. In such case, the original residue type needs to be removed from the reference structure and replaced by the pattern residue type. Each replacement step is preferably done by respecting the rules of standard geometry (standard bond lengths and angles and default torsion angles). In the preferred SPA mode of implementation of the invention, the set of single residue patterns may consist of all valid residue types as defined above, placed at each residue position of the region of interest. The set of pair residue patterns may consist of all possible pair-wise combinations thereof.

Fully consistent with the present invention is any method used in step B in order to further restrict the number of valid residue types at each position in the region of interest. Such an embodiment may be used (1) when the available computational resources necessitate a restriction, or (2) in cases which are interrelated with the application of ECO's. Ignoring the first case (thus assuming infinite computational resources), it will be clear to those skilled in the art that some residue types may be discarded from consideration depending on the position in the reference structure. Examples of such restriction methods include, without limitation:

the exclusion of synthetic residue types,
the exclusion of proline (actually an imino acid) residues depending on the local main-chain conformation,
the restriction of core residues to non-polar types,
the exclusion of residue types with low helical propensity in alpha-helices,
the preservation of the chemical nature (e.g. aromatic) of residue types in the reference structure, and so on.

So far, a pattern p is defined as one or more residue types placed into the reference structure at well defined residue positions. In order to unambiguously define p, the conformation of each p-residue must be further specified by the assignment of one specific conformation to each residue of p, preferably by selecting a specific rotamer from a rotamer library as described hereinabove. Alternatively, in the non-rotameric embodiment of the present invention, the said conformational assignment may result from other sources including, but not limited to, experimentally determined protein structures, computer-generated conformations or, as described below, a grouping process applied to different ECO's. The present invention does not impose restrictions to the nature and origin of the conformation of the p-residues. In the preferred SPA mode of implementation of the present invention, all (combinations of) rotamers are applied to the p-residues. For patterns consisting of residue pairs, this leads to a six-dimensional space. In order to keep the "volume" of this hyperspace within reasonable bounds, a variety of simple and more complicated criteria may be established in order to reduce the number of patterns for residue pairs. However, such criteria are ignored in the present invention since the results of any reduction method necessarily leads to a set of patterns of interest, which is the subject of the present invention.

The most important property of an ECO is its energy value which is defined as the difference between the global energy of the reference structure and the global energy of the same reference structure after its modification by the steps of (1) introducing the ECO pattern into the reference structure and (2) computing the globally optimal conformational rearrangement of the reference structure as illustrated in FIG. 2. Steps (1) and (2) will be referred to as the pattern introduction (PI) step and the structural adaptation (SA) step respectively. Computing the ECO energy value is therefore preferably completed by a third step called the energy calculation (EC) step wherein the global energy of the substituted and adapted structure is calculated and further wherein the global energy of the reference structure is subtracted from this value.

The PI step involves the necessary substitutions and the generation of the correct conformation of the p-residues, as dictated by the precise definition of the pattern p. This is preferably accomplished by a conventional protein modeling package such as disclosed by Delhaise et al. (cited supra) comprising practical tools in order to perform amino acid substitutions and conformational manipulations. Once the pattern p is introduced, the amino acid type(s) and conformation(s) of the substituted residues are frozen throughout the process leading to the ECO energy value computation. The PI step can be seen as a specific perturbation of the reference structure, leaving this structure in a sub-optimal state. Indeed, the introduced residues in their fixed conformation may very well be in steric conflict with surrounding amino acids.

In the SA step, the latter are given a chance to rearrange and find a new relaxed conformation in which steric constraints are alleviated and intramolecular interactions are improved. According to the present invention, this rearrangement is energy-based, i.e. the cost function to be optimized during the SA step is the energy of the global structure as defined in the section ENERGY FUNCTION. In a preferred embodiment of the invention, especially the rotameric embodiment described in the section CONFORMATIONAL FREEDOM, all atoms of the pattern residues and the main-chain of the reference structure are held fixed throughout the SA step. In a less preferred embodiment, the pattern atoms remain fixed but the main-chain atoms may slightly (i.e. by about 1 to 2 Å) change in position during the SA step. In another embodiment, and only for the non-rotameric approach, also the pattern atoms may change in position during the adaptation step; this embodiment is least preferred since the introduced pattern then looses its original structure and accounts, at least partially, for the structural relaxation effects.

The SA step itself may be performed by any method suitable for protein structure prediction (see STRUCTURE OPTIMIZATION) on the basis of an objective energetic scoring function (see ENERGY FUNCTION). The goal of the SA step is to find the energetically best possible substituted and adapted structure. In this step, the substituted reference structure is submitted to a structural optimization process exploring the conformational space of the protein system, taking into account (i) the restraints imposed onto the backbone and pattern atoms (which are preferably fixed), (ii) the allowed conformational freedom (e.g. as determined by a rotamer library) and (iii) the applied energy function. The specific procedure used in order to perform the said structural optimization is not critical to the present invention. Methods which may be used for this purpose are described in the section STRUCTURE OPTIMIZATION.

In the EC step, the ECO energy value is calculated as a differential value, i.e. the energy of the substituted and adapted structure obtained from the SA step, minus the energy of the reference structure. Both energies can be readily obtained by a standard energy calculation method using the relevant energy function in order to compute all relevant intra-molecular interactions and providing a quantitative estimate for the free or potential energy of a protein structure. Therefore the ECO energy value obtained by substracting both energies is a quantitative measure for the energetic cost to mutate the pattern p into the reference structure. As far as the computed energies correspond with the true thermodynamic free energies of the original (WT) and mutated proteins, they will reflect the change in thermodynamic stability of the mutated protein. Consequently, the ECO energy value can also be considered as a fair estimate of the structural compatibility of the pattern p within the framework of the protein of interest. The ECO energy value can be either positive (in which case the p-residues are expected to be less compatible with the protein than the WT residues) or negative (in which case the corresponding pattern is expected to stabilize the protein molecule).

Apart from the ECO pattern and the associated energy value, an ECO may also include other relevant information, including data referring to the origin of the ECO such as (i) a reference (e.g. a PDB-code) to the (e.g. experimentally determined) 3D structure of the protein used in the ECO generation, (ii) a reference to the rotamer library used to model the reference structure and the adapted structure, (iii) a reference to the applied energy function, (iv) a reference to the method used in the adaptation step, (v) a description of the reference sequence and structure, and (vi) the transformations (as discussed below) which may be applied to the native ECO. The latter data are important for a correct interpretation of the ECO energy. Moreover, they provide a large amount of added value:

first, since an ECO is self-describing, it should be possible to verify or reconstruct its energy value.

secondly, the information related to energetic transformations provide the user with a full autonomy to restore or re-transform these data (e.g. to express the data in normalized units) if needed in a particular application.

thirdly, this information considerably facilitates all forms of data mining. For example, it makes it easy to compare sets of ECO's constructed with different rotamer libraries, homologous backbone structures, energy models, adaptation methods or reference sequences.

In addition to the aforementioned data, other relevant though non-essential informations may be stored in the ECO object. Examples of such informations include, but are not limited to, (i) a description of the observed secondary structure for each pattern position, (ii) atomic coordinates for some or all atoms of the pattern residues, e.g. atomic coordinates for the Cα atoms, which may be helpful in identifying neighboring/distant residues without loading a full 3D-structure, (iii) a description of the solvent accessibility (e.g. the accessible surface area) of each p-residue. While not essential for the assessment of the ECO energy value, the storage of such additional data may be valuable when using ECO's for specialized applications like high-throughput fold recognition or protein design. A more extensive list of additional ECO elements is provided in the section FORMAL DESCRIPTION OF ECO'S.

For the sake of compactness, data elements in an ECO object which refer to the protein structure, residue types, rotameric states, and so on are preferably encoded as indices pointing to data present in external lists, instead of explicitly including the raw data. Also, ECO's sharing common properties (e.g. ECO's generated for the same protein structure, using the same rotamer library and energy function) may be grouped into a data structure (e.g. a file, an array or a database), the shared properties being assigned to the data structure rather than included in each ECO object. However, this kind of data storage and encoding is purely a mode of implementation, not an essential aspect of the present invention.

Many further transformations of the native ECO energy values obtained from the EC step may be useful within the context of specific applications of the present invention. Examples of such transformations include, without limitation, (i) the expression of ECO energies relatively to the lowest value of all ECO's known for different patterns located at the same residue positions, so that each transformed ECO energy becomes positive, (ii) transforming ECO energies by means of a linear, logarithmic or exponential function, (iii) truncating every transformed or non-transformed ECO energy above a given threshold value to that threshold value, (iv) the expression of ECO's in normalized units, and so on.

Another type of transformation, i.e. the grouping of native ECO's into grouped ECO's (referred as GECO's), does form part of the present invention. This grouping is applicable to the SPA mode wherein a multitude of ECO's are generated for identical positions in a protein. In a preferred embodiment of this invention, ECO's sharing identical positions in the protein of interest may be grouped into GECO's in order to (i) reduce the amount of information and (ii) extract the most significant information. The importance of ECO grouping as well as some preferred methods to generate GECO's is discussed in the section GROUPED ECO'S.

Formal Description of ECO's

In order to formally describe ECO's and to use ECO energies for single and pairs of residues in computing the energy of multiply substituted proteins, the following notations are used (see also LIST OF SYMBOLIC NOTATIONS).

N: the set of residue positions of interest within the protein of interest. Example 1: N={all amino acid residues of the protein}. Example 2: N={all fully buried amino acid residues of the protein}.

i: a specific residue position of interest i, where i∈N. Example: i=1 denotes the first residue position of N.

A(i): the set of residue types of interest at position i. In the SPA mode of the present invention, this set may contain multiple residue types. Example 1: A(1)={all natural amino acid residue types}. Example 2: A(1)={Gly, Ala, Ser}.

$i^a$: a specific residue type of interest a at position i, where $i^a \in A(i)$. Example: $i^a = 1^2$ denotes the second residue type of A(1), at the first residue position.

$R(i^a)$: the set of rotamers of interest for residue type a at position i. Rotamers of interest may be retrieved from either a backbone dependent or independent library. Example 1: $R(i^a)=R(a)$=the set of rotamers known for residue type a in the rotamer library described by De Maeyer et al. (cited supra). Example 2: $R(i^a)=R(a)\backslash\{$rotamers which are backbone-constrained at position i$\}$. Example 3: the set of rotamers $R(i^a)$ where a refers to a Gly residue type may contain either no element or one dummy element since Gly has no rotatable side chain.

$i_r^a$: a specific rotamer of interest r for residue type a at position i, where $i_r^a \in R(i^a)$. A specific instance of $i_r^a$ forms a uniquely defined single residue pattern. Example: $i_r^a = 1_3^2$ denotes the pattern formed by the third rotamer of $R(1^2)$, for the second residue type of A(1), at the first residue position.

[i,j]: the pair of specific residue positions of interest i and j.

$[i^a,j^b]$: the pair of residue positions i and j, where residue types a and b are placed at positions i and j, respectively (in an undefined conformation).

$[i_r^a,j_s^b]$: the pair of residue positions i and j, where residue types a and b are placed at positions i and j, respectively, and residue types a and b adopt rotameric states r and s, respectively. A specific instance of $[i_r^a,j_s^b]$ forms a uniquely defined pair residue pattern.

[i,j,k, . . . ]: the multiplet of residue positions of interest i,j,k, . . .

$[i^a,j^b,k^c, \ldots]$: the multiplet of residue positions i,j,k, . . . where residue types a,b,c, . . . are placed at positions i,j,k, . . . , respectively (in an undefined conformation).

$[j_r^a,j_s^b,k_t^c, \ldots]$: the multiplet of residue positions i,j,k, . . . where residue types a,b,c, . . . are placed at positions i,j,k, . . . , respectively, and residue types a,b,c, . . . adopt rotameric states r,s,t, . . . , respectively. A specific instance of $[i_r^a,j_s^b,k_t^c, \ldots]$ forms a uniquely defined multi-residue pattern.

P: the complete set of patterns of interest when generating ECO's in the SPA mode.

P(i): the set of single residue patterns of interest at position i, where P(i)⊆P. By analogy, P([i,j]) and, in general, P([i,j,k, . . . ]) is defined for pair and multiple residue patterns.

$P(i^a)$: the set of single residue patterns for residue type a at position i, where $P(i^a) \subseteq P(i) \subseteq P$. By analogy, $P([i^a,j^b])$ and, in general, $P([i^a,j^b,k^c,\ldots])$ is defined for pair and multiple residue patterns having defined residue types.

ref: the reference structure of the protein of interest. Preferably the reference structure is the energetically best possible global structure for the protein of interest. In the preferred embodiment of the invention wherein rotamers are used to describe the allowed conformational states of residue types, the reference structure can be written as a special pattern $[i_g^r,j_g^r,k_g^r,\ldots]$. In this pattern, all N residues i,j,k, . . . of the protein (excluding those of the template) assume the reference amino acid type as defined in the reference sequence (referred to as the "reference type" r), and a particular rotameric state as obtained from a structure prediction method such as a DEE method (referred to as the "global minimum energy rotamer" g). Note that r and g are not variables and are therefore not written in italic. Less preferably, the reference structure may be any energetically relaxed, e.g. energy minimized by a steepest descent or conjugated gradient method, structure. Least preferably, the reference structure may be any non-optimized experimental or theoretical structure for the protein of interest or, alternatively, the reference structure may be void and may be assigned a reference energy $E_{ref}=0$.

$E_{ref}$: the global energy of the reference structure. In the preferred embodiment using rotameric descriptions, a fixed template and a pair-wise summable energy function, $E_{ref}$ can be conveniently written as $$E_{ref}=E_{template}+\Sigma_i E_t(i_g^r)+\Sigma_i \Sigma_{j>i} E_p(i_g^r,j_g^r) \quad (eq.4).$$

Here, $E_{template}$ is the template self-energy, i.e. the sum of all atomic interactions within the template. The superscripts r refer to the reference amino acid type and the subscripts g denote the reference rotamer (the global minimum energy rotamer). $E_t(i_g^r)$ is the direct interaction energy of $i_g^r$ with the template, including its self-energy (the subscript t refers to the template). The self-energy may include a solvent correction term such as a TTS term as discussed in the section ENERGY FUNCTION. $E_p(i_g^r,j_g^r)$ denotes the pair-wise residue/residue interaction energy, also called rotamer/rotamer pair-energy between $i_g^r$ and $j_g^r$. Likewise, pair-energies may include a solvent correction term as discussed in the section ENERGY FUNCTION. Optionally, the term $E_{template}$ can be omitted in equation (4) since (i) it is a constant and (ii) $E_{ref}$ is to be used in combination with $E(i_r^a)$, discussed below, wherein the same term can be discarded (in such case, $E_{ref}$ is not a global but a partial energy). A great advantage of equation (4) is that the $E_t$ and $E_p$ terms can be pre-computed for all possible instances of single and pair residue patterns. These values can then repeatedly be used in the search for the optimal reference structure as well as in the computation of ECO energy values. In a less preferred embodiments wherein no rotamers are used and/or the template is not fixed and/or a non-pair-wise summable energy model is applied, the reference energy $E_{ref}$ must be calculated in accordance with the characteristics of the applied energy model, and typically as a sum over all possible inter-atomic interactions within the reference structure. In the least preferred embodiment, where no reference structure is considered, $E_{ref}$ may be set equal to 0 or any arbitrary value, with the consequence that ECO energies can no longer be interpreted as "substitution energies". However, such embodiments may still be useful in specific applications wherein the absolute values of ECO energies are irrelevant, e.g. when different mutations are compared one with another.

$E(i_r^a)$: the global energy for the reference structure which has been modified by (1) a PI step wherein the single residue pattern $i_r^a$ is mutated into the reference structure and (2) a SA step as described in the section DESCRIPTION OF THE ECO CONCEPT. This is not a differential but an absolute energy for a complete molecule. In the preferred embodiment using rotamers, a fixed template and a pair-wise energy function, this energy can be calculated in accordance with following equation (5), wherein the terms applicable to residue i of the single residue pattern $i_r^a$ are replaced by the appropriate energy contributions:

$$E(i_r^a)=E_{template}+E_t(i_r^a)+\Sigma_j E_p(i_r^a,j_g^r)+\Sigma_j E_t(j_g^r)+\Sigma_j\Sigma_{k>j} E_p(j_g^r,k_g^r); j,k\neq I \quad (eq.5).$$

In this equation, the residue positions j,k≠i may have quit their reference rotameric state r as a result of the SA step, but not their reference type g: Adaptation occurs by conformational rearrangements wherein type switches are not allowed. In the optional case that $E_{template}$ has been omitted in the calculation of $E_{ref}$, the same term should be omitted in equation (5) as well and $E(i_r^a)$ is not a global but a partial energy. In a less preferred embodiment wherein no rotamers are used and/or the template is not fixed and/or a non-pair-wise summable energy function is applied, the value for $E(i_r^a)$ must be calculated similarly to the reference energy $E_{ref}$, typically as a sum over all possible inter-atomic interactions within the substituted and adapted structure.

$E_{ECO}(i_r^a)$: the ECO energy value for the single residue pattern $i_r^a$. As previously defined, it is the energy of the reference structure which has been substituted by and conformationally adapted to the pattern $i_r^a$, $E(i_r^a)$, minus the energy of the reference structure:

$$E_{ECO}(i_r^a)=E(i_r^a)-E_{ref} \quad (eq.6).$$

This definition is valid for all embodiments of the present invention. By analogy, it is also possible to define ECO energies for pair patterns. In the preferred embodiment using rotamers, a fixed template and a pair-wise energy function, the global energy of the reference structure substituted by and adapted to a pair residue pattern $[i_r^a, j_s^b]$ can be written as follows:

$$E([i_r^a,j_s^b])=E_{template}+E_t(i_r^a)+E_t(j_s^b)+E_p(i_r^a,j_s^r)+\Sigma_k E_p(j_s^b,k_t^r)+\Sigma_k E_t(k_t^r)+\Sigma_k\Sigma_{l>k}E_p(k_t^r,l_u^r);$$
$$i\neq j; k,l\neq i,j \quad (eq.7)$$

The ECO energy for a pair residue pattern is then $$E_{ECO}([i_r^a,j_s^b])=E([i_r^a,j_s^b])-E_{ref} \quad (eq.8)$$

In the less preferred embodiments wherein no rotamers are used and/or the template is not fixed and/or a non-pair-wise summable energy function is applied, the value for $E([i_r^a,j_s^b])$ must be calculated in accordance with the characteristics of the applied energy model, and typically as a sum over all possible interatomic interactions within the substituted and adapted structure. In the general case of multi-residue patterns, the calculation of ECO energies occurs as for single and pair residue patterns. Here, only the equation for the ECO energy of a multi-residue pattern $[i_r^a,j_s^b,k_t^c,\ldots]$ is given:

$$E_{ECO}([i_r^a,j_s^b,k_t^c,\ldots])=E([i_r^a,j_s^b,k_t^c,\ldots])-E_{ref} \quad (eq.9)$$

In order to complete the above formal description of ECO's, a more concrete description of the term is now provided. An energetic compatibility object is a structured data set comprising elements or pieces of information. Here, a distinction may be made between (i) basic elements and (ii) optional elements, depending on whether they are essential for a correct execution of an ECO-based application or whether they may simply be helpful in such execution. Clearly, this distinction depends on the specific application of interest to a user.

The basic elements of an ECO are those which together form a full description of the origin and characteristics of a substituted and adapted protein structure, i.e. in particular:

I. a structural description of the protein of interest or its PDB-code.
II. a description of the applied method for structural pre-refinement of I, if any.
III. a description of the applied rotamer library, if any. In the preferred embodiment of the present invention, this corresponds to the assignment of a set of rotamers $R(i^a)$ to each position i defined in (V). For positions i being pattern residues, a refers to a pattern residue type, whereas for non-pattern positions of interest, a refers to the residue type as defined in (VI).
IV. a description of the applied energy function.
V. a description of the set N, i.e. the set of residue positions i of interest. This set consists of positions in the protein at which a pattern p is placed (pattern positions), as well as positions which are considered in the SA step (non-pattern positions). The complement of N is defined as the template which, in the preferred embodiment of this invention, is fixed.
VI. a description of the amino acid reference sequence, i.e. the assignment of one specific "reference amino acid type" r to each position i defined in (V).
VII. the method applied to compute the reference structure for (VI), starting from (I) or (II), and using (III) and (IV) (e.g. a DEE method).
VIII. a description of the reference structure for the residue positions and types defined in (V) and (VI) respectively and obtained by the method defined in (VII), e.g. the assignment of a "global optimum" rotamer g to each position defined in (V).
IX. the pattern residue position(s), i.e. [i,j,k, . . . ]
X. the pattern residue type(s), i.e. $[i^a, j^b, k^c, \ldots]$
XI. the pattern residue conformations, i.e. $[i_r^a, j_s^b, k_t^c, \ldots]$ (this may be optional for grouped ECO's or in the embodiments not using rotamers).
XII. the method applied to perform the SA step for the reference structure defined in (VIII), wherein the pattern defined in (IX), (X) and (XI) is introduced, preferably being the same method as used in (VII).
XIII. the ECO energy value $E_{ECO}([i_r^a, j_s^b, k_t^c, \ldots])$ as defined by equation (9) or, alternatively, equations (6) and (8) for single and pair residue patterns, respectively.

Optional elements of an ECO are in particular:

XIV. a specification of the residues which have changed their conformation (e.g. by adopting a rotameric state different from g) during the SA step, as well as a description of the actual changes such as, preferably, the new rotamers.
XV for grouped ECO's, a reference to the grouping method, as well as a comprehensive description of the results of the grouping process.
XVI. one or more functional properties of the protein of interest.
XVII. a local secondary structure description of the pattern residue positions [i,j,k, . . . ] within the protein structure as in (I).
XVIII. a description of the solvent accessibility of the pattern residues within the reference structure (i.e. $[i_g^r, j_g^r, k_g^r, \ldots]$) and/or within the substituted and adapted structure (i.e. $[i_r^a, j_s^b, k_t^c, \ldots]$).
XIX. cartesian coordinates of one or more atoms of the pattern residues within the reference structure and/or within the substituted and adapted structure.
XX. crystallographic temperature factors associated with the (atoms of) the pattern residues within the protein structure from which the reference structure has been deduced.
XXI. known chemical modifications associated with the pattern residues within the protein structure from which the reference structure has been deduced.
XXII. physico-chemical properties associated with the pattern residue types.

Clearly, this list can be enlarged with any additional property of interest to the user.

Systematical Pattern Analysis (SPA) Mode

ECO's may be generated by the present method at the time they are needed, for example, to search locations in a protein where tryptophan substitutions are allowed. Dozens of questions of this type may be answered by one or more real-time, case-specific pattern analysis experiments. However, some structure-related questions can only be resolved by the present method if vast amounts of ECO data are available. Moreover, the same ECO information may be used recurrently within the context of different protein design experiments. Also, specific design and recognition tasks may be performed in the absence of any explicit 3D-representation of a protein. Finally, pre-computed sets (or databases) of ECO's may be data mined to gain structure- and sequence-related insights, again creating added value. Therefore, there is a need to generate ECO's in a systematic way, called the "systematical pattern analysis" (SPA) mode of operation.

The notations, conventions and abbreviations used below conform to those listed in the section FORMAL DESCRIPTION OF ECO'S.

In the SPA mode of the present invention, wherein only the rotameric embodiment is relevant, ECO's are systematically generated for a pre-defined set P of patterns being substituted into the reference structure of a protein of interest. Also, a distinction needs to be made between single and double residue ECO's. Multi-residue ECO's are not considered in the SPA mode only because their systematical computation may be too slow.

For single ECO's, the set P is constructed as follows. First, a set I of residue positions i is defined, where I is a subset of N (the positions of interest, actually all modeled residues). At each position $i \in I$, a set A(i) of residue types of interest is defined. A residue type a placed at position i is noted as $i^a$, where $i^a \in A(i)$ and where $i^a$ can be interpreted as a single residue pattern in an as yet undefined conformation. It is noteworthy that at different positions i, different sets of types A(i) may be considered. Next, for each defined position/type combination $i^a$, a set $R(i^a)$ comprising rotamers of interest for type a at position i is established, preferably retrieved from a rotamer library. A rotamer r, generated for type a, placed at position i is noted as $i_r^a$, where $i_r^a \in R(i^a)$ and where $i_r^a$ can be interpreted as an unambiguous single residue pattern $p \in P$.

For double ECO's, basically the same approach is followed, but all combinations of types and rotamers need to be considered for all possible pairs of positions. More specifically, define by $i,j \in I$ a pair of residue positions, by $i^a \in A(i)$ and $j^b \in A(j)$ a pair of residue types at positions i and j, respectively, and by $i_r^a \in R(i^a)$ and $j_s^b \in R(j^b)$ a pair of rotamers for types a and b at positions i and j, respectively, then the set P consists of all possible unique and unambiguous pair-residue patterns $[i_r^a, j_s^b]$, where i<j.

In the SPA mode, the reference structure for the protein of interest needs to be generated only once (see REFERENCE STRUCTURE) and the associated reference energy $E_{ref}$ can be used in the calculation of the ECO energy value for all patterns of the set P. Then all patterns of P are substituted into the reference structure, the structure is adapted to the pattern and the total energy is calculated using equation (5) or (7) for single or double-residue patterns, respectively. This yields necessary and sufficient data to calculate the ECO energy associated with each single and/or double residue pattern, using eqs. (6) and/or (8), respectively.

Finally, the generated data are stored on a suitable storage device (preferably into an array, a file or a database) where typically one object per pattern is created; each object contains (some of) the data and references described in the section FORMAL DESCRIPTION OF ECO'S. Post-analysis operations including transformations (see DESCRIPTION OF THE ECO CONCEPT) or grouping operations (see GROUPED ECO'S) may then be applied.

Grouped ECO'S (GECO'S)

Besides energetic transformations (see DESCRIPTION OF THE ECO CONCEPT), the most important post-analysis method, applicable to ECO's generated in the SPA-mode of the present invention, is the grouping of ECO's into GECO's. While there is a nearly infinite variety of possible grouping operations, we shall specifically address GECO's which are preferred in view of their practical usefulness and ease of interpretation i.e. (i) single GECO's, (ii) double GECO's and (iii) GECO's resulting from a grouping operation performed on the basis of residue type properties.

A single GECO, denoted $G(i^a)$, is a GECO derived from an ensemble of single residue ECO's, generated in SPA-mode, for a specific amino acid residue type a placed at position i, and a set of rotamers $R(i^a)$, i.e. the patterns of this ensemble only differ in rotameric state. Each ECO of this ensemble can be seen as the result of a trial experiment wherein the compatibility of its associated pattern, i.e. a particular residue type a at position i in rotameric state r, is investigated within the context of an adaptive reference structure. A clear measure for the said compatibility is the energy of each ECO of this ensemble, $E_{ECO}(i_r^a)$. In a preferred embodiment, the set of $E_{ECO}(i_r^a)$ values for a given residue position and type $i^a$ and all rotamers $r \in R(i^a)$ can simply be grouped by searching over all rotameric states for the minimum value for $E_{ECO}(i_r^a)$ according to equation (10):

$$E_{GECO}(i^a) = \min_r E_{ECO}(i_r^a) \tag{eq.10}$$

wherein $E_{GECO}(i^a)$ is the energy value resulting from the minimum searching operation on all $E_{ECO}(i_r^a)$ values. If desired, the min-rotamer $r_{min}$ can replace the pattern rotamer element in a GECO object (element (XI) in the FORMAL DESCRIPTION OF ECO'S) but this is only optional since a GECO is primarily intended to assess the compatibility of an amino acid type at a specific position, rather than that of a conformation. A numerical illustration of such grouping operation is shown in the following table 2.

Another preferred method to group ECO's is by taking the average over a set of low-energy values, wherein the latter set includes all values for $E_{ECO}(i_r^a)$ below a suitably chosen threshold value T, according to equation (11).

$$E_{GECO}(i^a) = \text{aver}_r(E_{ECO}(i_r^a) | E_{ECO}(i_r^a) \leq T) \tag{eq.11}$$

wherein $\text{aver}_r$ is the averaging operator working on $E_{ECO}(i_r^a)$ values below T for all rotamers r at $i^a$. When applying equation (11), some residue types a may not be compatible with position i, i.e. if no $E_{ECO}(i_r^a)$ value exists below T. When applying this grouping method, it is impossible to assign a specific rotamer r to the resulting GECO, but this is irrelevant if the grouping process is only for the purpose of assessing the compatibility of a amino acid types.

Another preferred grouping method is based on using a probabilistic averaging function such as shown in equation (12):

$$E_{GECO}(i^a) = \Sigma_r E_{ECO}(i_r^a) p(i_r^a) \tag{eq.12}$$

wherein $$p(i_r^a) = \exp(-\beta E_{ECO}(i_r^a))/Z(i^a) \tag{eq.13}$$

and wherein $\beta$ is a suitable constant (e.g. $\beta = 1/(k_B T)$ wherein $k_B$ is Boltzmann's constant and T is the temperature in degrees Kelvin) and $Z(i^a)$ is the partition function defined by equation (14) as:

$$Z(i^a) = \Sigma_r \exp(-\beta E_{ECO}(i_r^a)) \tag{eq.14}$$

This grouping method is highly preferred since it is statistically supported and requires no absolute energetic threshold value.

A double GECO, denoted $G([i^a, j^b])$, is a grouped ECO derived from an ensemble of double residue ECO's, generated in SPA-mode, for pair residue patterns implying $[i^a, j^b]$. $G([i^a, j^b])$ which provides information regarding the compatibility of the pair of residue types a and b, at positions i and j, respectively, without necessarily specifying their rotameric states. The possibilities to group double ECO's for pair residue patterns $[i_r^a, j_s^b]$ are analogous to those for grouping single ECO's. In a first embodiment, the minimum energy value for all pair-wise combinations of rotamers r and s can be searched according to equation (15):

$$E_{GECO}([i_r^a, j_s^b]) = \min_{r,s} E_{ECO}([i_r^a, j_s^b]) \tag{eq.15}$$

wherein $\min_{r,s}$ is the minimum searching operator.

A second embodiment involves averaging combinations having a pair energy below a given threshold, following equation (16):

$$E_{GECO}([i_r^a, j_s^b]) = \text{aver}_{r,s}(E_{ECO}([i_r^a, j_s^b]) | E_{ECO}([i_r^a, j_s^b]) \leq T) \tag{eq.16}$$

wherein $\text{aver}_r$ is the averaging operator.

A third embodiment is a statistical averaging according to equation (17):

$$E_{GECO}([i_r^a, j_s^b]) = \Sigma_{r,s} E_{ECO}([i_r^a, j_s^b]) p([i_r^a, j_s^b]) \tag{eq.17}$$

wherein $$p([i_r^a, j_s^b]) = \exp(-\beta E_{ECO}([i_r^a, j_s^b]))/Z([i_r^a, j_s^b]) \tag{eq.18}$$

and the partition function $Z([i_r^a, j_s^b])$ is $$Z([i_r^a, j_s^b]) = \Sigma_{r,s} \exp(-\beta E_{ECO}([i_r^a, j_s^b])) \tag{eq.19}$$

Another type of grouping is at the level of amino acid features or properties rather than rotamers, which is useful in assessing the compatibility of a certain type of amino acid, e.g. an aromatic amino acid, at residue position i. Indeed, GECO's can be constructed by grouping amino acids sharing some feature or property of interest. For example, $G(i^{Pol})$ where Pol={S,T,N,D,E,Q,R,K} denotes a GECO for a polar amino acid at position i. The energy value associated with such a GECO can be suitably defined by equation (20) as:

$$E_{GECO}(i^{Kind}) = \text{aver}_{a \in Kind} E_{GECO}(i^a) \tag{eq.20}$$

Such a grouping is preferably performed on GECO's already grouped by type (over rotameric states). Other potentially useful grouping operations include, but are not limited to, sets of:

aromatic amino acid types where Kind={H,F,Y,W},
small residue types where Kind={G,A} or {G,A,S},
β-branched types where Kind={I,V,T},
and the like.

Generally speaking, this latter type of grouping is intended for and suitable to condense primary information into structured information of a higher level which may be useful, for example, in fold recognition by fast screening of amino acid sequences against structure-based profiles.

Assessing Global Energies from Single and Double (G)ECO'S

The present invention also relates to a method to assess the global fitness of a protein structure in which an arbitrary number of substitutions have taken place compared to a reference amino acid sequence. More specifically, it is possible to assess the global energy, and thereby the fitness, of a multiply substituted protein structure by making use of single and preferably also double ECO or GECO energy values. The computation of this global energy may occur by simply summing energetic terms for single residues and pairs of residues as demonstrated hereinafter. As a consequence, the compatibility of a given amino acid sequence with a given protein 3D structure, after proper alignment, can be assessed fastly, compared to current methods using conventional modelling techniques.

First, the assessment method of the invention establishes a mathematical relationship between single and double ECO energies. Then this relationship is further analyzed, thereby demonstrating how double ECO energies can be derived from single ECO energies. Next, this method is extended so as to compute the energy of multi-residue patterns from single ECO energies. Finally, it is discussed how single and double GECO's can be used to assess the global energy of a multiply substituted protein structure.

In the preferred embodiment of the present invention, i.e. when using rotamers, a fixed template and a pair-wise energy function, the global energy of a reference amino acid sequence in its reference structure is given by equation (4). When isolating, in this equation, the energetic contributions for two residue positions of interest i and j, we obtain equation (21):

$$E_{ref} = E_{template} + \Sigma_k E_t(k_g^r) + \Sigma_k \Sigma_{l>k} E_p(k_g^r, l_g^r) + E_t(i_g^r) + E_t(j_g^r) + E_p(i_g^r, j_g^r) + \Sigma_k E_p(i_g^r, k_g^r) + \Sigma_k E_p(j_g^r, k_g^r);$$
$$i \neq j; k, l \neq i, j \qquad (eq.21)$$

wherein all terms and symbols have the same meaning as in equation (4).

A similar equation for $E(i_r^a)$ can be derived from equation (5), wherein the contributions for the residue positions i and j are isolated, recalling that $E(i_r^a)$ is the energy for the reference structure in which the reference rotamer $i_g^r$ has been replaced by the pattern rotamer $i_r^a$ and where the other residues have had the opportunity to assume a new lowest energy rotamer g' which may or may not be different from the reference rotamer g. Thus, we can write $E(i_r^a)$ as $$E(i_r^a) = E_{template} + \Sigma_k E_t(k_{g'}^r) + \Sigma_k \Sigma_{l>k} E_p(k_{g'}^r, l_{g'}^r) + E_t(i_r^a) + E_t(j_{g'}^r) + E_p(i_r^a, j_{g'}^r) + \Sigma_k E_p(i_r^a, k_{g'}^r) + \Sigma_k E_p(j_{g'}^r, k_{g'}^r);$$
$$i \neq j; k, l \neq i, j \qquad (eq.22)$$

Likewise, we obtain for $E(j_s^b)$, i.e. the global energy of the reference structure substituted by and adapted to the pattern $j_s^b$, wherein possible rotameric adaptations are denoted by the subscript g":

$$E(j_s^b) = E_{template} + \Sigma_k E_t(k_{g''}^r) + \Sigma_k \Sigma_{l>k} E_p(k_{g''}^r, l_{g''}^r) + E_t(i_{g''}^r) + E_t(j_s^b) + E_p(i_{g''}^r, j_s^b) + \Sigma_k E_p(i_{g''}^r, k_{g''}^r) + \Sigma_k E_p(j_s^b, k_{g''}^r); i \neq j; k, l \neq i, j \qquad (eq.23)$$

The energy of the pair pattern $[i_r^a, j_s^b]$, causing rotameric adaptations denoted by the subscript g'" is given by equation (24):

$$E([i_r^a, j_s^b]) = E_{template} + \Sigma_k E_t(k_{g'''}^r) + \Sigma_k \Sigma_{l>k} E_p(k_{g'''}^r, l_{g'''}^r) + E_t(i_r^a) + E_t(j_s^b) + E_p(i_r^a, j_s^b) + \Sigma_k E_p(i_r^a, k_{g'''}^r) + \Sigma_k E_p(j_s^b, k_{g'''}^r); i \neq j; k, l \neq i, j \qquad (eq.24)$$

If the expression (21) for $E_{ref}$ is subtracted from equations (22) to (24), we obtain the equations for the single ECO energies $E_{ECO}(i_r^a)$ and $E_{ECO}(j_s^b)$ and for the double ECO energy $E_{ECO}([i_r^a, j_s^b])$ as follows:

$$E_{ECO}(i_r^a) = \Sigma_k(E_t(k_{g'}^r) - E_t(k_g^r)) + \Sigma_k \Sigma_{l>k}(E_p(k_{g'}^r, l_{g'}^r) - E_p(k_g^r, l_g^r)) + (E_t(i_r^a) - E_t(i_g^r)) + (E_t(j_{g'}^r) - E_t(j_g^r)) + (E_p(i_r^a, j_{g'}^r) - E_p(i_g^r, j_g^r)) + \Sigma_k(E_p(i_r^a, k_{g'}^r) - E_p(i_g^r, k_g^r)) + \Sigma_k(E_p(j_{g'}^r, k_{g'}^r) - E_p(j_g^r, k_g^r));$$
$$i \neq j; k, l \neq i, j \qquad (eq.25)$$

$$E_{ECO}(j_s^b) = \Sigma_k(E_t(k_{g''}^r) - E_t(k_g^r)) + \Sigma_k \Sigma_{l>k}(E_p(k_{g''}^r, l_{g''}^r) - E_p(k_g^r, l_g^r)) + (E_t(i_{g''}^r) - E_t(i_g^r)) + (E_t(j_s^b) - E_t(j_g^r)) + (E_p(i_{g''}^r, j_s^b) - E_p(i_g^r, j_g^r)) + \Sigma_k(E_p(i_{g''}^r, k_{g''}^r) - E_p(i_g^r, k_g^r)) + \Sigma_k(E_p(j_s^b, k_{g''}^r) - E_p(j_g^r, k_g^r));$$
$$i \neq j; k, l \neq i, j \qquad (eq.26)$$

$$E_{ECO}([i_r^a, j_s^b]) = \Sigma_k(E_t(k_{g'''}^r) - E_t(k_g^r)) + \Sigma_k \Sigma_{l>k}(E_p(k_{g'''}^r, l_{g'''}^r) - E_p(k_g^r, l_g^r)) + (E_t(i_r^a) - E_t(i_g^r)) + (E_t(j_s^b) - E_t(j_g^r)) + (E_p(i_r^a, j_s^b) - E_p(i_g^r, j_g^r)) + \Sigma_k(E_p(i_r^a, k_{g'''}^r) - E_p(i_g^r, k_g^r)) + \Sigma_k(E_p(j_s^b, k_{g'''}^r) - E_p(j_g^r, k_g^r)); i \neq j; k, l \neq i, j \qquad (eq.27)$$

Each of equations (25) to (27) consists of a large number of terms which have been ordered specifically to make them more interpretable, as follows: the first line in each equation contains terms related to non-pattern residue positions $k, l \neq i, j$ only; the second line, in contrast, contains only terms related to pattern residues i,j; and finally, the third line contains interactions between pattern positions i,j and non-pattern positions $k \neq i, j$. Moreover, all terms are grouped in pairs wherein the reference contributions "g" are subtracted from the pattern related terms "g', g", g'''", i.e. each pair of terms therefore reflects the difference brought about by a pattern substitution. Bearing this in mind, we can substitute $$\Delta E_{self}^k(p) = \begin{cases} \sum_k (E_t(k_{g'}^r) - E_t(k_g^r)) + \sum_k \sum_{l>k}(E_p(k_{g'}^r, l_{g'}^r) - E_p(k_g^r, l_g^r)); & p = i_r^a \\ \sum_k (E_t(k_{g''}^r) - E_t(k_g^r)) + \sum_k \sum_{l>k}(E_p(k_{g''}^r, l_{g''}^r) - E_p(k_g^r, l_g^r)); & p = j_s^b \\ \sum_k (E_t(k_{g'''}^r) - E_t(k_g^r)) + \sum_k \sum_{l>k}(E_p(k_{g'''}^r, l_{g'''}^r) - E_p(k_g^r, l_g^r)); & p = [i_r^a, j_s^b] \end{cases} \qquad (eq. 28)$$

where $\Delta E_{self}^k(p)$ is preferably interpreted as the difference in the global internal (or "self") energy of the non-pattern residues $k, l \neq i, j$ (compared to the reference structure) due to conformational rearrangements induced by pattern p, where p is either $i_r^a$, $j_s^b$ or $[i_r^a, j_s^b]$. Similarly, we can substitute $$\Delta E_{int}^{ij-k}(p) = \begin{cases} \sum_k \left(E_p(i_r^a, k_{g'}^r) - E_p(i_g^r, k_g^r)\right) + \sum_k \left(E_p(j_{g'}^r, k_{g'}^r) - E_p(j_g^r, k_g^r)\right); \ p = i_r^a \\ \sum_k \left(E_p(i_{g''}^r, k_{g''}^r) - E_p(i_g^r, k_g^r)\right) + \sum_k \left(E_p(j_s^b, k_{g''}^r) - E_p(j_g^r, k_g^r)\right); \ p = j_s^b \\ \sum_k \left(E_p(i_r^a, k_{g'''}^r) - E_p(i_g^r, k_g^r)\right) + \sum_k \left(E_p(j_s^b, k_{g'''}^r) - E_p(j_g^r, k_g^r)\right); \ p = [i_r^a, j_s^b] \end{cases} \quad \text{(eq. 29)}$$

where $\Delta E_{int}^{ij-k}(p)$ is preferably interpreted as the difference in total interaction energy between the pattern residues i,j and the non-pattern residues k≠i,j (compared to the reference structure) due to conformational rearrangements induced by pattern p, where p is either $i_r^a$, $j_s^b$ or $[i_r^a, j_s^b]$. When entering the former two quantities into equations (25) to (27), we obtain $$E_{ECO}(i_r^a) = \Delta E_{self}^k(i_r^a) + (E_t(i_r^a) - E_t(i_g^r)) + (E_t(j_{g'}^r) - E_t(j_g^r)) + (E_p(i_r^a, j_{g'}^r) - E_p(i_g^r, j_g^r)) + \Delta E_{int}^{ij-k}(i_r^a) \quad \text{(eq.30)}$$

$$E_{ECO}(j_s^b) = \Delta E_{self}^k(j_s^b) + (E_t(i_{g''}^r) - E_t(i_g^r)) + (E_t(j_s^b) - E_t(j_g^r)) + (E_p(i_{g''}^r, j_s^b) - E_p(i_g^r, j_g^r)) + \Delta E_{int}^{ij-k}(j_s^b) \quad \text{(eq.31)}$$

$$E_{ECO}([i_r^a, j_s^b]) = \Delta E_{self}^k([i_r^a, j_s^b]) + (E_t(i_r^a) - E_t(i_g^r)) + (E_t(j_s^b) - E_t(j_g^r)) + (E_p(i_r^a, j_s^b) - E_p(i_g^r, j_g^r)) + \Delta E_{int}^{ij-k}([i_r^a, j_s^b]) \quad \text{(eq.32)}$$

This set of equations now allows to write a double ECO energy as a function of single ECO energies. For this purpose, equations (30) and (31) are subtracted from equation (32).

$$E_{ECO}([i_r^a, j_s^b]) - E_{ECO}(i_r^a) - E_{ECO}(j_s^b) = \Delta E_{self}^k([i_r^a, j_s^b]) - (\Delta E_{self}^k(i_r^a) + \Delta E_{self}^k(j_s^b)) + \Delta E_{int}^{ij-k}([i_r^a, j_s^b]) - (\Delta E_{int}^{ij-k}(i_r^a) + \Delta E_{int}^{ij-k}(j_s^b)) - (E_t(i_{g''}^r) - E_t(i_g^r)) - (E_t(j_{g'}^r) - E_t(j_g^r)) + (E_p(i_r^a, j_s^b) - E_p(i_g^r, j_g^r)) - (E_p(i_r^a, j_{g'}^r) - E_p(i_g^r, j_g^r)) - (E_p(i_{g''}^r, j_s^b) - E_p(i_g^r, j_g^r)) \quad \text{(eq.33)}$$

The terms appearing in the second and third line of equation (33) may be analysed as follows. First, they measure the energetic consequences for the non-pattern residues k≠i,j due to the introduction of the patterns $i_r^a$, $j_s^b$ and $[i_r^a, j_s^b]$. Secondly, it can be safely assumed that introducing any single or pair residue pattern is unlikely to change the conformation of an entire protein structure, whereas the introduction of e.g. a single residue pattern $i_r^a$ is likely to cause adaptation events for only a limited number of residues k in its immediate environment. In other words, it is expected that a protein structure shows some "plasticity" behaviour with respect to perturbations of its structure (i.e. the reference structure), i.e. small patterns are likely to induce small, local changes. Taking this expectation for true, it can also be expected that two different single residue patterns $i_r^a$ and $j_s^b$ may have non-overlapping associated sets of adapted residues. Formally defining by K(p) the set of non-pattern residues k≠i,j which adopt a different rotameric state (compared to the reference structure) after the introduction of, and adaptation to, the pattern p, for the three possible sets of patterns defined on i and/or j we have:

$$K(i_r^a) \equiv \{k | k_{g'}^r \neq k_g^r\} \quad \text{(eq.34)}$$

$$K(j_s^b) \equiv \{k | k_{g''}^r \neq k_g^r\} \quad \text{(eq.35)}$$

$$K([i_r^a, j_s^b]) \equiv \{k | k_{g'''}^r \neq k_g^r\} \quad \text{(eq.36)}$$

The condition for non-overlapping sets of adapted residues associated with patterns $i_r^a$ and $j_s^b$ is then represented by equation (37):

$$K(i_r^a) \cap K(j_s^b) = \emptyset \quad \text{(eq.37)}$$

A question addressed by the method of the present invention is then to define the relationship between the sets $K(i_r^a)$, $K(j_s^b)$ and $K([i_r^a, j_s^b])$ and, more specifically, the conformation of the elements in each set. Ignoring all other theoretical possibilities, we introduce herein an hypothesis called "additivity of adaptation" (AA) which is illustrated in FIG. 3 and assumes that conformational adaptation effects caused by a pair pattern $[i_r^a, j_s^b]$ are identical to the sum of all adaptation effects caused by each of its constituting single residue patterns $i_r^a$ and $j_s^b$. A first criterion for this hypothesis to be fulfilled is that the introduction of a pair pattern $[i_r^a, j_s^b]$ affects exactly the same residue positions k≠i,j as being affected by either the single residue pattern $i_r^a$ or $j_s^b$, which may be formally represented by equation (38):

$$K(i_r^a) \cup K(j_s^b) = K([i_r^a, j_s^b]) \quad \text{(eq.38)}$$

A further requirement for AA is that all rotamers $k_{g'''}^r \neq k_g^r$ induced by the pattern $[i_r^a, j_s^b]$ are found among the rotamers induced by either the single residue pattern $i_r^a$ or $j_s^b$. This criterion can be expressed formally by the following equation:

$$\begin{cases} k_{g'''}^r = k_{g'}^r; \ \forall k | k \in K(i_r^a) \\ k_{g'''}^r = k_{g''}^r; \ \forall k | k \in K(j_s^b) \end{cases} \quad \text{(eq. 39)}$$

This criterion is unambiguous if the conditions set forth in equations (37) and (38) are fulfilled. Then, under the AA hypothesis, the equations (30) to (32) can be drastically simplified, e.g. by combining equations (28) and (39):

$$\Delta E_{self}^k([i_r^a, j_s^b]) - \Delta E_{self}^k(i_r^a) - \Delta E_{self}^k(j_s^b) = 0 \quad \text{(eq.40)}$$

and, similarly, by combining equations (29) and (39):

$$\Delta E_{int}^{ij-k}([i_r^a, j_s^b]) - \Delta E_{int}^{ij-k}(i_r^a) - \Delta E_{int}^{ij-k}(j_s^b) = 0 \quad \text{(eq.41)}$$

so that equation (33) simplifies to:

$$E_{ECO}([i_r^a, j_s^b]) = E_{ECO}(i_r^a) + E_{ECO}(j_s^b) - (E_t(j_{g'}^r) - E_t(j_g^r)) - (E_t(i_{g''}^r) - E_t(i_g^r)) + (E_p(i_r^a, j_s^b) - E_p(i_g^r, j_g^r)) - (E_p(i_r^a, j_{g'}^r) - E_p(i_g^r, j_g^r)) - (E_p(i_{g''}^r, j_s^b) - E_p(i_g^r, j_g^r)) \quad \text{(eq.42)}$$

When the AA criteria are met, equation (42) provides a means to compute the energy of a double ECO from the energies of single ECO's. This equation only requires terms directly involving pattern positions i and j, not terms related to non-pattern positions. The said terms involving pattern positions i and j can be readily computed as soon as the rotamers $j_{g'}^r$ (induced by $i_r^a$) and $i_{g''}^r$ (induced by $j_s^b$) as well as the associated template ($E_t$) and pair ($E_p$) energies are known and can be considered as corrections needed to derive double ECO energies from single ECO's. These terms can be grouped into a new function $E_{fuse}(i_r^a, j_s^b)$, comprising the said energetic corrections needed to fuse two single ECO energies into one double ECO energy, defined in equation (43):

$$E_{fuse}(i_r^a, j_s^b) = -E_t(j_{g'}^r) - E_t(i_{g''}^r) + E_t(i_g^r) + E_t(j_g^r) + E_p(i_r^a, j_s^b) - E_p(i_r^a, j_{g'}^r) - E_p(i_{g''}^r, j_s^b) + E_p(i_g^r, j_g^r) \quad \text{(eq.43)}$$

Then, still under the AA hypothesis, equation (42) becomes:

$$E_{ECO}([i_r^a, j_s^b]) = E_{ECO}(i_r^a) + E_{ECO}(j_s^b) + E_{fuse}(i_r^a, j_s^b) \quad \text{(eq.44)}$$

When the AA criteria are not met as illustrated in FIG. 3b, errors in equation (44) due to ignoring non-additivity effects can be included in a non-additivity term $E_{non-AA}(i_r^a, j_s^b)$ leading to a universally applicable expression:

$$E_{ECO}([i_r^a, j_s^b]) = E_{ECO}(i_r^a) + E_{ECO}(j_s^b) + E_{fuse}(i_r^a, j_s^b) + E_{non-AA}(i_r^a, j_s^b) \quad \text{(eq.45)}$$

The first three terms at the right hand side of equation (45), as well as the double ECO energy, can be exactly calculated. Therefore, equation (45) provides a practical means to statistically analyse possible errors due to neglecting non-additivity effects and to correlate these errors with properties related to single residue patterns.

The present invention is also able to investigate in detail the relationship between single and double GECO's. This is of special importance because GECO's, being grouped over the rotameric dimension (r), are dependent only of a position (i) and type (a) and, consequently, allow for a huge reduction of data while keeping only the most relevant information. Since GECO's reflect how well residue types (not necessarily rotamers) can fit at specific positions in a protein structure, analysis of the relationship between single and double GECO's would possibly make it possible to answer questions like:

If a double substitution $[i^a, j^b]$ is energetically compatible, is each single substitution $[i^a]$ and $[j^b]$ energetically compatible as well, and vice-versa?, and can double GECO's be easily derived from single GECO's?

The ultimate aim of such analysis is to predict the energetic compatibility of multiple substitutions from information related to single and double GECO's, thereby facilitating protein design and fold recognition applications by allowing detailed, structure-based predictions without actually considering any 3D structure.

By analogy to equation (45), the following relationship between single and double GECO energies is first assumed:

$$E_{GECO}([i^a, j^b]) = E_{GECO}(i^a) + E_{GECO}(j^b) + E_{fuse}(i^a, j^b) + E_{non-AA}(i^a, j^b) \quad \text{(eq.46)}$$

wherein $E_{GECO}([i^a, j^b])$ is the energy of a GECO of a special pattern p defined on residue positions i and/or j carrying types a and/or b, respectively, but where the rotameric states is are not necessarily defined. The non-additivity term $E_{non-AA}(i^a, j^b)$ has the same meaning as previously, i.e. it reflects the energetic consequences of a possible inconsistence between adaptations caused by patterns $i^a$ and $j^b$ versus $[i^a, j^b]$. Although some ambiguity may lie in this term since the rotameric state of each of these patterns may be undefined, except for GECO's derived by equations (10) and (15), however this term can simply be ignored since the method of the present invention is preferably used under the AA hypothesis. In equation (46), $E_{fuse}(i^a, j^b)$ may be considered as a correction term needed to take into account that $i^a$ has been considered in the reference structure where j had type r (and mutatis mutandis for $j^b$). Since both types a and b are likely to be different from the corresponding types in the reference structure, this fuse-term can adopt a wide variety of values, both negative and positive. In contrast to the foregoing description, it would be in conflict with the basic GECO concept to attempt to calculate $E_{fuse}(i^a, j^b)$ by similarity with equation (43) for the following reason. If the rotameric states of the involved residues are unknown or irrelevant, then it becomes impossible or irrelevant to consider the associated rotamer/template and rotamer/rotamer interaction energies as in equation (43). A much more practical way to assign $E_{fuse}(i^a, j^b)$ values is to derive them directly from the single and double GECO energies according to equation (47):

$$E_{fuse}(i^a, j^b) = E_{GECO}([i^a, j^b]) - (E_{GECO}(i^a) + E_{GECO}(j^b)) \quad \text{(eq.47)}$$

which is true when there is additivity in the adaptation effects caused by the pair of single GECO's and the double GECO. However, when the AA hypothesis is not fulfilled, the energetic consequences (actually, $E_{non-AA}(i^a, j^b)$) will be incorporated into the fuse term $E_{fuse}(i^a, j^b)$. Anyhow, equation (47) can be used to compute double GECO energies from a database containing single GECO energies and pair-wise fuse terms without effectively generating the double GECO.

Another aspect of the present invention is a method to compute the energy of multiply substituted proteins from single and double GECO energies. Considering that:

equation (45) means that the substitution energy of a multiplet pattern (such as a pair) can be derived from the substitution energy of basic patterns (i.e. single residues), the present invention relates to energy functions which are essentially pair-wise additive in the sense that the global energy of a protein structure can be written in a form equivalent to equation (4), the fuse term in equation (45) mainly contains energetic contributions which are directly and exclusively related to pattern residue positions, and the non-additivity effects are expected to be small in size compared to the fuse term in eq (45).

Taking into account the previous elements and remarks, we postulate that the total substitution energy of a protein structure comprising a multiplet pattern of the type $[i^a, j^b, k^c, \ldots]$ can be approximated by the equation $$E_{GECO}([i^a, j^b, k^c, \ldots]) \approx E_{GECO}(i^a) + E_{GECO}(j^b) + E_{GECO}(k^c) + \ldots + E_{fuse}(i^a, j^b) + E_{fuse}(i^a, k^c) + \ldots + E_{fuse}(j^b, k^c) + \ldots + \ldots \quad \text{(eq. 48)}$$

If the pattern residue positions are not explicitly given a specific name, then equation (48) can be written in a simpler form:

$$E_{GECO}(p) \approx \Sigma_i E_{GECO}(i^{a(i)}) + \Sigma_i \Sigma_{j>i} E_{fuse}(i^{a(i)}, j^{b(j)}) \quad \text{(eq. 49)}$$

where p is a multiplet pattern defined on any number of residue positions of interest i and a residue type of interest a(i) is placed at position i in an undefined rotameric state, and where $E_{GECO}(i^{a(i)})$ is the single residue GECO energy for $i^{a(i)}$, and where $E_{fuse}(i^{a(i)}, j^{b(j)})$ is the fuse term for two single residue patterns $i^{a(i)}$ and $j^{b(j)}$, preferably calculated from the corresponding double GECO energy and both single GECO energies using equation (47).

Clearly, equation (49) forms an essential aspect of the present invention since it indicates that the energetic compatibility of any amino acid sequence of interest within the context of an adaptive reference structure can be assessed from only single and pair-wise energy terms (which are preferably stored in a database).

Potential errors in the calculation of $E_{GECO}(p)$ by means of equation (49) compared to when p would be effectively substituted and modeled into the reference structure, may result from different sources. However, the quantitative global error in equation (49) can be included in an extra error term for the multiplet pattern p, $E_{error}(p)$, so that we obtain $$E_{GECO}(p) = \Sigma_i E_{GECO}(i^{a(i)}) + \Sigma_i \Sigma_{j>i} E_{fuse}(i^{a(i)}, j^{b(j)}) + E_{error}(p) \quad \text{(eq. 50)}$$

The latter equation provides a practical means to quantitatively estimate the total error for a variety of different patterns p. Indeed, if $E_{GECO}(p)$ computed with equation (49) is renamed as $E_{GECO}^{approx}(p)$ and $E_{GECO}(p)$ resulting from the true modeling of p in the reference structure is referred to as $E_{GECO}^{mod}(p)$, then $$E_{error}(p) = E_{GECO}^{approx}(p) - E_{GECO}^{mod}(p) \quad \text{(eq. 51)}$$

In the section FOLD RECOGNITION APPLICATION, a correlation is made between the approximate and modeled GECO energies for a selected protein structure and a wide variety of different patterns substituted into the topologically most difficult part of the protein, i.e. the core.

Proof of Principle

Hereinafter, the practical usefulness of the ECO concept with respect to two important fields of application is illustrated. In a first experiment, a fold recognition simulation is performed by searching a near-optimal correlation between a target amino acid sequence of interest and a transformed-GECO profile derived for a protein structure which is homologous to the target sequence. In a second experiment, a protein design experiment is carried out on three selected positions in the B1 domain of protein G (PDB code 1PGA). More specifically, at three selected residue positions 100 randomly chosen triple mutations were modeled and the global energy of each modeled structure was compared to the energy calculated on the basis of single and double GECO energies, in accordance with equation (49). From a correlation plot between the two sets of energy data, it follows that the global energy of a multiply substituted protein structure may be estimated from only single and double GECO energies with sufficient accuracy. Since the latter computations occur extremely fast compared to the effective modeling of multiple substitutions, the method based on single and double GECO's may be useful to rapidly generate a set of amino acid sequences which are likely to be compatible with a protein structure.

Fold Recognition Application

In order to exemplify the potential of the ECO concept with respect to fold recognition applications, single residue ECO's were generated for hen lysozyme (PDB code 3LZT) by applying the SPA embodiment of the present invention (see TABLE 1 for experimental settings and data). Next, the single residue ECO's were grouped into single residue GECO's for each residue position/type combination by searching the minimal ECO energy value over all rotamers, in accordance with equation (10) (see Table 2). The resulting set of GECO's is hereinafter referred to as the initial GECO profile for the protein studied. The initial profile for 3LZT was stored to disk so that different versions of a recognition method (described below) could be tested using the same initial profile.

It has been observed that five different consecutive transformations of GECO energies were helpful to obtain a near-optimal alignment between a target amino acid sequence and a GECO profile. A first transformation, performed on the initial GECO profile for 3LZT, involved the translation of the distribution of GECO energies for a given residue position by the lowest value observed for that position over all residue types. The transformation equation used was $$E_{GECO,1}(i^a) = E_{GECO}(i^a) - \min_a E_{GECO}(i^a) \quad \text{(eq. 52)}$$

where $E_{GECO,1}(i^a)$ is the transformed GECO energy for residue type a at position i, $E_{GECO}(i^a)$ is the initial GECO energy for $i^a$ and $\min_a$ is the min-operator to search for the lowest possible $E_{GECO}(i^a)$ value at position i. As a result of this operation, all transformed GECO energies became equal to or greater than zero. A second transformation included the truncation of all $E_{GECO,1}(i^a)$ values to a maximal value of 100, as formally expressed by equation (53):

$$E_{GECO,2}(i^a) = \min(E_{GECO,1}(i^a), 100) \quad \text{(eq. 53)}$$

where min is the min-operator acting on its two arguments, i.e. $E_{GECO,1}(i^a)$ and a value of 100. As a result, strongly restrained substitutions (see Table 2) received a default value of 100. A third transformation was a logarithmic rescaling of $E_{GECO,2}(i^a)$ values by applying the following equation:

$$E_{GECO,3}(i^a) = \log(1 + E_{GECO,2}(i^a) \times 0.99)$$

whereby a $E_{GECO,2}(i^a)$ interval [0,100] was mapped onto a $E_{GECO,3}(i^a)$ interval [0,2] by a decimal logarithm function. Next, these values were converted to normalized units as follows: first, a fourth transformation was performed on the distributions of $E_{GECO,3}(i^a)$ values for each position i. These distributions were assumed to be Gaussian (which is, admittedly, an approximation) and the average value, $\mathrm{aver}_a(E_{GECO,3}(i^a))$, and standard deviation, $\mathrm{std}_a(E_{GECO,3}(i^a))$, were calculated for each position i over all residue types a. Then, equation (55)

$$E_{GECO,4}(i^a) = (E_{GECO,3}(i^a) - \mathrm{aver}_a(E_{GECO,3}(i^a)))/\mathrm{std}_a(E_{GECO,2}(i^a)) \quad \text{(eq. 55)}$$

was performed on all $E_{GECO,3}(i^a)$ values, which essentially rescales the transformed GECO energies to a number of standard deviations above or below the average value observed for a position i. Negative $E_{GECO,4}(i^a)$ values may be associated with "favorable" or "better than average" substitutions whereas positive values may be seen as "unfavorable" substitutions. Next, a fifth transformation was performed on the $E_{GECO,4}(i^a)$ values for the 20 residue type distributions by the equation $$E_{GECO,5}(i^a) = (E_{GECO,4}(i^a) - \mathrm{aver}_i(E_{GECO,4}(i^a)))/\mathrm{std}_i(E_{GECO,4}(i^a)) \quad \text{(eq. 56)}$$

which rescales the $E_{GECO,4}(i^a)$ values to a number of standard deviations above or below the average value observed for a residue type a. The reason for the fourth transformation was to include a correction for the intrinsic level of difficulty to place different residue types at a given position, while the fifth transformation intended to correct for the intrinsic level of complexity to place a given residue type at different positions. A set of $E_{GECO,5}(i^a)$ values for all residue positions i of a given protein structure and the 20 naturally occurring residue types a at each position is hereinafter called a transformed GECO profile for the protein involved.

Target amino acid sequences were compared with transformed GECO profiles using a modified Smith-Waterman (SW) alignment procedure in accordance with R. Durbin et al. in *Biological Sequence Analysis. Probabilistic models of proteins and nucleic acids* (1998) at Cambridge University Press. The modification consisted in that no gap formation was allowed, which is equivalent to assigning an infinite gap penalty value. Since the SW approach requires that (i) a favorable alignment of a residue against a given position in a profile receives a positive score value (whereas favorable $E_{GECO,5}(i^a)$ values are negative) and (ii) the global expected value of score contributions should be negative (whereas the global expected value for $E_{GECO,5}(i^a)$ values is zero as a result of the normalization operations), two additional transformations of the $E_{GECO,5}(i^a)$ values were needed. First, the sign of the $E_{GECO,5}(i^a)$ values was inverted to meet the first requirement:

$$E_{GECO,6}(i^a) = -E_{GECO,5}(i^a) \quad \text{(eq. 57)}$$

In addition, during construction of a SW alignment matrix, a value of 0.5 was subtracted from the $E_{GECO,6}(i^a)$ values to meet the second requirement. This means that a residue only contributes in a favorable way to an alignment if its $E_{GECO,6}(i^a)$ value is greater than 0.5 (i.e. if the log-transformed $E_{GECO,3}(i^a)$ value is at least 0.5 standard deviations below the average value at position i). However, since this transformation was only intended to identify high-scoring sequence fragments on the basis of maxima in the alignment matrix, in accordance with the SW method, the non-transformed $E_{GECO,6}(i^a)$ values were used in all further calculations. From the SW alignment matrix, the 50 highest-scoring fragments were selected, being characterized by (i) an offset in the target sequence, (ii) an offset in the transformed GECO profile, (iii) a length l and (iv) a cumulative alignment score z being the sum of $E_{GECO,6}(i^a)$ contributions for positions i in the profile and residue types a observed in the target sequence.

The obtained fragments were further statistically analyzed by calculating the probability that they were found by pure chance. The probability P(l,z) that a randomly aligned fragment of a given length l and consisting of uncorrelated, randomly selected residue types has an alignment score equal to or better than a given score z can be derived as follows. If two variables $x_1$ and $x_2$ are independent normal variables with an average value of 0 and a standard deviation of 1, here written as N(0,1), then their sum is distributed as N(0,√2), i.e. a distribution centered around 0, with a standard deviation equal to √2, , according to Neuts in *Probability* (1973) at Allyn and Bacon, Inc. (Boston). By extension, the sum of n such variables is distributed as N(0,√n). Then, the probability P(n,z) that the sum of n such variables is equal to or greater than a value z, is given by the integration of the probability density function N(0,√n):

$$P(n, z) = \int_z^{1-\infty} \frac{1}{\sqrt{2\pi n}} e^{\frac{-x^2}{2n}} dx \quad \text{(eq. 58)}$$

When applied to aligned fragments of length l having a cumulative score z, and for which the constituent residues have a normal distribution N(0,1), the probability that the said value z or any greater value is obtained by pure chance is given by equation (59):

$$P(l, z) = \int_z^{1-\infty} \frac{1}{\sqrt{2\pi l}} e^{\frac{-x^2}{2l}} dx \quad \text{(eq. 59)}$$

The latter equation allowed to assign a P-value to all high-scoring fragments, which P-value corresponds to the probability that one random positioning of a fragment of length l results in a score of at least z, which is different from the probability to obtain at least one fragment of length l with a score of at least z (in the latter case, the size of the target sequence and the profile need to be considered). The assignment of a P-value to each of the 50 highest-scoring fragments allowed to rank all fragments according to their significance. Finally, all fragments having a P-value below $10^{-4}$ were retained as potentially significant.

The final global alignment was obtained by first clearing, in the aforementioned SW alignment matrix, all values for matrix elements not forming part of any retained fragment and, secondly, performing a Needleman-Wunsch (NW) protocol to find the best possible concatenation of the retained fragments (R. Durbin et al., cited supra). The NW protocol was performed using a gap opening penalty of 2.0 and a gap extension penalty of 0.2, resulting in a unique global alignment. The assessment of the significance of a global alignment was performed by summing the cumulative score for all fragments forming part of the global alignment, diminished by 2×(the number of fragments−1), further diminished by 0.2×the total number of non-matched residue positions between matched fragments, inputting this value into equation (59) in order to obtain a global P-value and qualifying the result as a "positively recognized fold" if the global P-value is below $10^{-15}$. Alternatively, a fold was also considered as "positively recognized" if the best fragment had a P-value below $10^{-10}$. This alignment procedure may not be optimal but that it forms a feasible and practically useful method to illustrate the potential of the ECO concept with respect to fold recognition.

The aforementioned procedure for ECO-based analysis of the structural compatibility of a target amino acid sequence with a protein 3D structure was applied to a homologous pair of proteins from the C-type lysozme family. Concretely, the sequence of human alpha-lactalbumin [SEQ ID NO: 12] was aligned with the transformed GECO profile of hen lysozyme [SEQ ID NO: 1] (PDB code 3LZT). The sequence identity between both proteins is 40% for the best matching fragment of 113 residues (out of 123 for lactalbumin and 129 for lysozyme), according to a BLAST alignment performed at the interne address http://www.ncbi.nlm.nih.gov/. As a result of the alignment procedure, 10 aligned fragments [SEQ ID NO: 2 to SEQ ID NO: 11] were retained having a P-value below $10^{-4}$ (FIG. 4). The best fragment had a P-value of $8.9 \times 10^{-15}$, which already qualified the lactalbumin target sequence as being structurally compatible with the 3LZT fold. Three other fragments (P-values in ascending order were $1.5 \times 10^{-11}$, $6.3 \times 10^{-7}$ and $1.9 \times 10^{-5}$) also formed part of the final global alignment. Since the 3D-structure of human alpha-lactalbumin is known (PDB code 1B9O), a structural comparison with 3LZT was possible. It was found that the NW concatenation procedure succeeded in selecting only those fragments which are indeed similar in structure. Non-matched regions (between the fragments) were observed typically in loop regions where one or more deletions occurred with respect to lysozyme. On the basis of this comparison, the alignment can be clearly qualified as truly positive. The six fragments not forming part of the final alignment were dissimilar in structure and were correctly excluded by the NW concatenation.

In order to investigate the discriminative power of the method with respect to non-homologous sequences, the lactalbumin sequence has been randomly permuted 1000 times and each sequence was aligned against the 3LZT profile. From each alignment, the best scoring fragment with the lowest P-value was retained. Out of these 1000 experiments, the best random fragment had a P-value of $1.4 \times 10^{-6}$ which agrees well with the false positive fragments generally appearing in each alignment experiment (FIG. 4). It also shows that the false positive fragment in the lactalbumin/lysozyme alignment having an exceptional P-value of $7.3 \times 10^{-9}$ must due to intra-fragment correlation effects, i.e. the high-scoring lactalbumin fragment cannot be equivalent to a random fragment. Since no structural similarity between the target and profile fragments could be observed, the nature of the presumed intra-fragment correlation is as yet not understood. Moreover, portions of this exceptional fragment also appeared in three other false positive fragments (i.e. fragments 5, 6 and 9 in FIG. 4), although their P-value was typical for random fragments, i.e. around $10^{-5}$.

In conclusion, these experiments show that the ECO concept is useful to identify a structural relationship between two protein molecules by aligning a target amino acid sequence against a GECO profile. Moreover, a global structure-based alignment may be obtained. These results are obtained by only using single ECO's, more specifically the substitution energies of single residues in the context of a reference structure which may be up to 60% different in amino acid sequence compared to a target sequence. When suitably including information derived from double ECO's, the quality of the alignments should expectedly increase, since double ECO's contain information related to pair-wise residue/residue interactions.

Protein Design Application

The B1 domain of protein G (PDB code 1PGA) was chosen to simulate 100 different randomly selected triple-residue substitutions and to compare the global energy obtained by the effective modeling of each triple-substitution with the global energy estimated on the basis of single and double GECO energies. This was not intended to predict the most stable variant but rather to show that protein design applications based on single and double (G)ECO's form a valuable alternative compared to previously known methods directly operating on a 3D structure, thereby being confronted with the combinatorial substitution problem.

First the GMEC of the 1PGA structure was computed using the FASTER method (such as previously described) and the same rotamer library and energy function as in all other calculations (see Table 1). All residues having a rotatable side chain were included in the GMEC computation. The global energy of this structure, which was taken as the reference structure in all experiments related to 1PGA, was $-149.3$ kcal mol$^{-1}$.

Three proximate residue positions being located in the core of 1PGA were selected to perform further design experiments. More specifically, residues 5 (LEU), 30 (PHE) and 52 (PHE), were chosen to be mutated into 100 different random combinations of residue types. Each combination is hereinafter called a mutated sequence and represented as {X,Y,Z} where X, Y and Z refer to the residue types placed at positions 5, 30 and 52, respectively. The WT "mutation" {LEU, PHE, PHE} was added to this set as an extra test. Each mutated sequence was modeled into 1PGA exactly in the same way as the WT sequence, after having performed the necessary side-chain replacements. These modeling experiments were executed by a pure structure prediction method (i.e. the FASTER method) and not by an embodiment of the present invention: the conformation of the mutated residues was not kept fixed (in contrast to patterns) but was co-modeled with that of all other rotatable side chains. Analysis of the results showed that the global energies of the mutated sequences ranged from $-149.3$ to $22274$ kcal mol$^{-1}$. However, all positive values were associated with sequences containing at least one PRO residue which is prohibited in a β-sheet (positions 5 and 52) and in an α-helix (position 30). The highest energy for sequences not containing PRO was $-85.5$ kcal mol$^{-1}$ and was associated with the sequence {TRP,GLN,VAL}. The sequences with a negative energy clustered around $-121.6 \pm 9.7$ kcal mol$^{-1}$ (standard deviation). No sequence had an energy better than the WT sequence, not surprisingly since only 100 out of the $20^3$ possible sequences were examined and since the WT structure is well-packed.

In order to exemplify the use of the ECO concept with respect to protein design, it was investigated how the energies from the modeled sequences could be approximated by using only single and double GECO energies. For this purpose, all possible single and double ECO's for the three selected positions were generated in agreement with the rotameric SPA embodiment of the present invention. The same experimental settings were applied as in the previous fold recognition experiments. ECO's were grouped into GECO's in accordance with equations (5) and (10) but no transformation was performed on the resulting GECO energies.

From the sets of calculated single residue GECO energies, $E_{GECO}(i^a)$, and double residue GECO energies, $E_{GECO}([i^a, j^b])$, an equivalent set of fuse terms, $E_{fuse}(i^a, j^b)$, was deduced by applying equation (47). The values for all fuse terms related to positions 5 and 30 are listed in Table 4. Most of the fuse terms are negative, which means that effectively modeled double mutations are generally better than the mere sum of each single substitution energy. Roughly speaking, negative values are expected to arise from better interactions in a double substitution compared to each single substitution being modeled into the reference structure, although a double substitution may also be energetically more constrained than each of the single mutations involved. In addition, some effects of non-additivity of adaptation may play a role as well. Yet, the fuse terms automatically correct for all these effects so that, together with the single GECO energies, they can be used "backwards" to reconstruct a double mutation without actually needing to model it.

Figure 5:
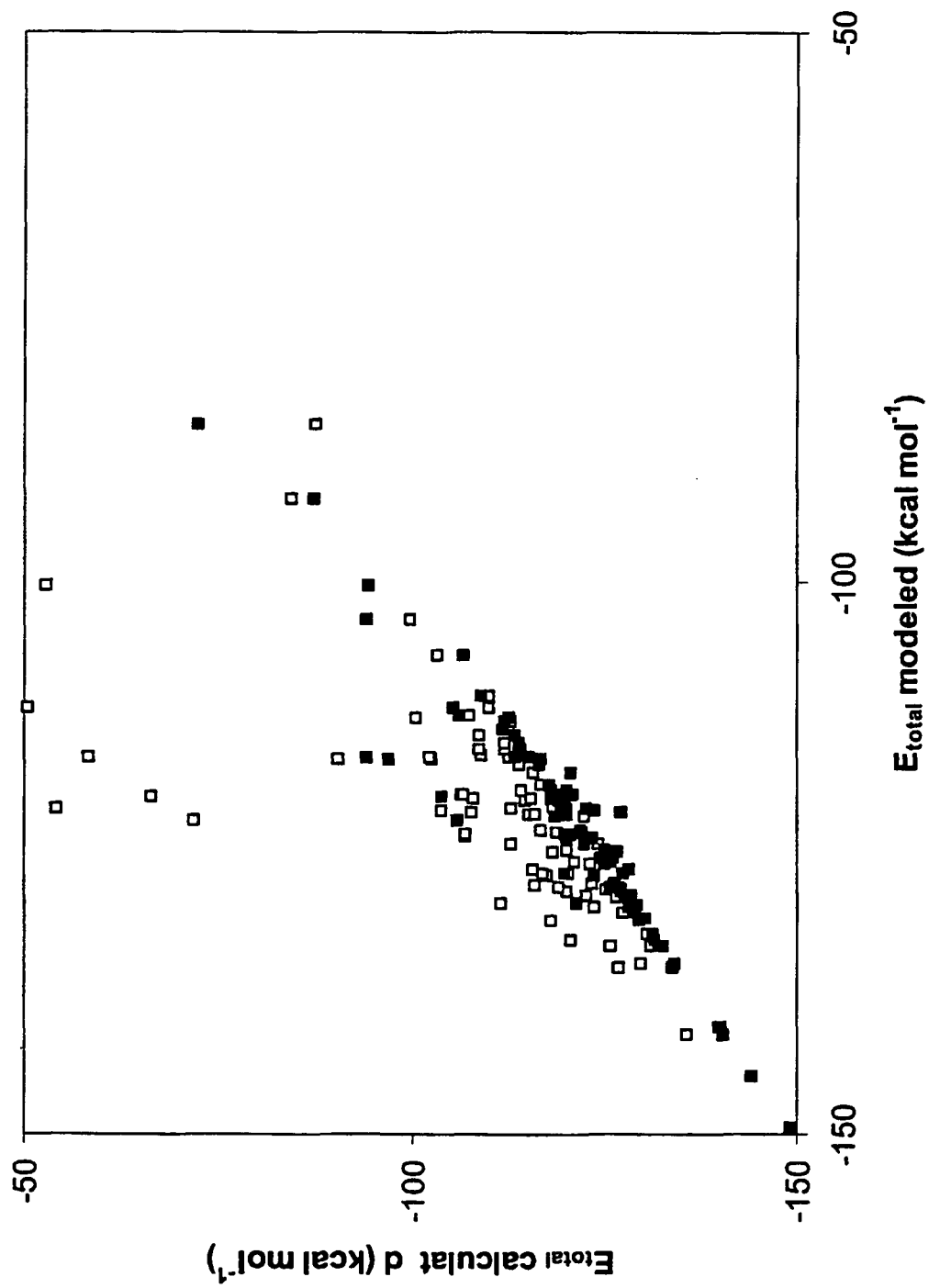
FIG. 5 shows a correlation diagram between the energy obtained from the effective modeling of 100 different triple mutations at residues 5, 30 and 52 of the B1 domain of protein G and the energy calculated for the same substitutions derived on the basis of GECO energies, according to the present invention.

The question of how equation (49) performs in the computation of the global energy of multiply substituted proteins was then investigated as follows. Each of the 101 triplet mutations (100 random sequences plus the WT sequence) was calculated using equation (49) and these energies were compared to the energies resulting from the effective modeling in a correlation diagram (FIG. 5). It was observed that both data sets correlate surprisingly well, given the numerous possible sources of approximation. Out of the 101 sequences, 55 had a difference between modeled and calculated energy less than 1 kcal mol$^{-1}$ in absolute value and 25 more had a difference less than 5 kcal mol$^{-1}$. The present invention includes difference of less than 10 kcal mol$^{-1}$. Moreover, in the most interesting range, i.e. for low-energy sequences, the correlation was even better. In the range up to 20 kcal mol$^{-1}$ above the energy of the WT sequence all 15 sequences differed in energy by less than 1 kcal mol$^{-1}$ in absolute value. Some larger differences were observed as well, but they were found exclusively in regions of higher energy. Even for the most constrained sequences containing at least one PRO (15 sequences; results not shown in FIG. 5), 14 had a difference in energy below 10 kcal mol$^{-1}$, while the energy of these modeled sequences was always higher than 400 kcal mol$^{-1}$. While most energy values calculated from single GECO energies and fuse terms were roughly evenly distributed above and below the values from the modeled sequences, the largest differences were always positive, which may be due to non-additivity in the adaptations upon calculation of the double residue ECO's (leading to an overestimation of the fuse terms). For comparison, the energy of each sequence calculated as the sum of each involved single GECO energy (ignoring the fuse terms) was plotted in FIG. 5 as well. Even here some correlation with the effectively modeled energies can be observed but the percentual difference is significantly higher, which illustrates that the fuse terms contribute to the global energy in a most beneficial way.

In conclusion, the estimation of the global energy of multiply substituted proteins may be performed to sufficient accuracy by using information derived from only single and double residue ECO's at least in the case studied, i.e. the core of the B1 domain of protein G. It is well-known in the art that core substitutions are among the most difficult ones since delicate packing effects are involved. Therefore, the present invention allows the design of new sequences, irrespective of the region where mutations are proposed. In addition, it is worth noting that the present embodiment to derive global energies from single and double residue GECO's is extremely fast when the latter values have been pre-calculated and can be retrieved from a file or database. Therefore, the present method may be useful to rapidly search a reduced set of structure-compatible sequences out of a combinatorial number of possibilities. Sequences obtained this way may then be submitted to more detailed analysis.

The present invention may be implemented on a computing device e.g. a personal computer or a work station which has an input device for loading the details of the reference structure and the reference amino acid sequence defined in step A of claim 1, and also any further amino acid sequences. The computing device is adapted to run software which carries out any of the methods in accordance with the present invention. The computer may be a server which is connected to a data communications transmission means such as the Internet. A script file including the details of the reference structure and the amino acid sequence may be sent from one near location, e.g. terminal, to a remote, i.e. second location, at which the server resides. The server receives this data and outputs back along the communications line useful data to the near terminal, e.g. the alignment of a sequence relative to the reference structure, or a set of favourable amino acid sequences for one or more residues in the reference structure, a protein where its sequence or a part thereof is determined by one or more of the claimed methods, a database or part of a database including sets of ECO's for one or more proteins; an ECO in the form of data structure.

Figure 6:
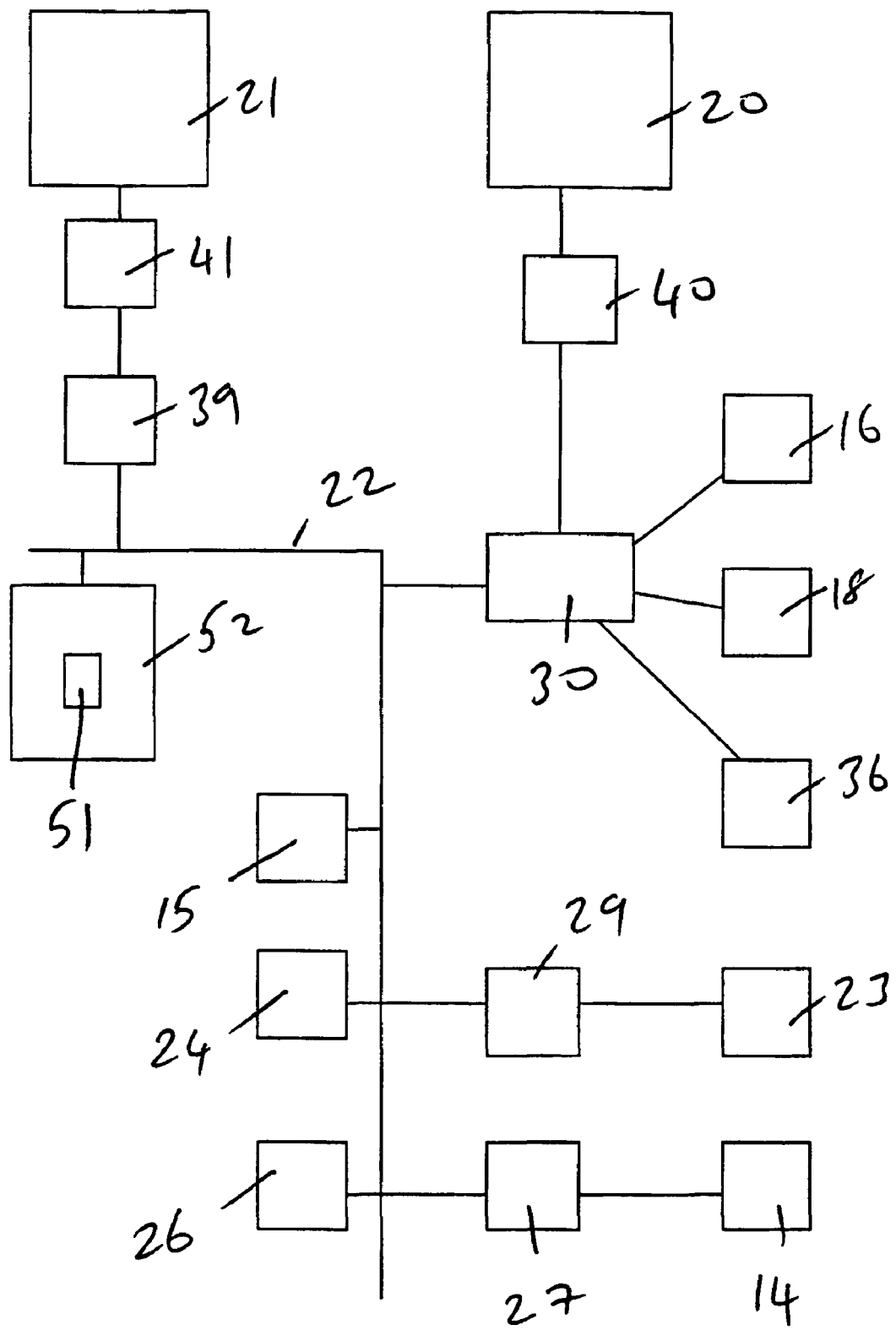
FIG. 6 shows a computer system suitable for use wth the present invention.

FIG. 6 is a schematic representation of a computing system which can be utilized in accordance with the method and system of the present invention. The system and method provided by the present invention can be implemented with the computing system depicted in FIG. 6. A computer 10 is depicted which may include a video display terminal 14, a data input means such as a keyboard 16, and a graphic user interface indicating means such as a mouse 18. Computer 10 may be implemented as a general purpose computer.

Computer 10 includes a Central Processing Unit ("CPU") 15, such as a conventional microprocessor of which a Pentium III processor supplied by Intel Corp. USA is only an example, and a number of other units interconnected via system bus 22. The computer 10 includes at least one memory. Memory may include any of a variety of data storage devices known to the skilled person such as random-access memory ("RAM"), read-only memory ("ROM"), non-volatile read/write memory such as a hard disc as known to the skilled person. For example, computer 10 may further include random-access memory ("RAM") 24, read-only memory ("ROM") 26, as well as an optional display adapter 27 for connecting system bus 22 to an optional video display terminal 14, and an optional input/output (I/O) adapter 29 for connecting peripheral devices (e.g., disk and tape drives 23) to system bus 22. Video display terminal 14 can be the visual output of computer 10, which can be any suitable display device such as a CRT-based video display well-known in the art of computer hardware. However, with a portable or notebook-based computer, video display terminal 14 can be replaced with a LCD-based or a gas plasma-based flat-panel display. Computer 10 further includes user interface adapter 30 for connecting a keyboard 16, mouse 18, optional speaker 36, as well as allowing optional physical value inputs from physical value capture devices 40 of an external system 20. The devices 40 may be any suitable equipment for capturing physical parameters required in the execution of the present invention. Additional or alternative devices 41 for capturing physical parameters of an additional or alternative external system 21 may also connected to bus 22 via a communication adapter 39 connecting computer 10 to a data network such as the Internet, an Intranet a Local or Wide Area network (LAN or WAN) or a CAN. The term "physical value capture device" includes devices which provide values of parameters of a system, e.g. they may be an information network or databases such as a rotamer library.

Computer 10 also includes a graphical user interface that resides within a machine-readable media to direct the operation of computer 10. Any suitable machine-readable media may retain the graphical user interface, such as a random access memory (RAM) 24, a read-only memory (ROM) 26, a magnetic diskette, magnetic tape, or optical disk (the last three being located in disk and tape drives 23). Any suitable operating system and associated graphical user interface (e.g., Microsoft Windows) may direct CPU 15. In addition, computer 10 includes a control program 51 which resides within computer memory storage 52. Control program 51 contains instructions that when executed on CPU 15 carries out the operations described with respect to the methods of the present invention as described above.

Those skilled in the art will appreciate that the hardware represented in FIG. 6 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already described.

In the example depicted in FIG. 6, the computer program product (i.e. control program 51 for executing methods in accordance with the present invention comprising instruction means in accordance with the present invention) can reside in computer storage 52. However, it is important that while the present invention has been, and will continue to be, that those skilled in the art will appreciate that the methods of the present invention are capable of being distributed as a program product in a variety of forms, and that the present invention applies equally regardless of the particular type of signal bearing media used to actually carry out the distribution. Examples of computer readable signal bearing media include: recordable type media such as floppy disks and CD ROMs and transmission type media such as digital and analogue communication links.

TABLE 1

| I | II | III | IV | V | VI | VII | VIII | IX | X | XI | XII | XIII |
|---|---|---|---|---|---|---|---|---|---|---|---|---|
| 3LZT | SD200 | 1 | allH | Flex | WT:ALA | Faster | 3LZT_G | 32 | GLY | 1 | Faster | 1.944 |
| 3LZT | SD200 | 1 | allH | Flex | WT:ALA | Faster | 3LZT_G | 32 | ALA | 1 | Faster | 0 |
| 3LZT | SD200 | 1 | allH | Flex | WT:ALA | Faster | 3LZT_G | 32 | PRO | 1 | Faster | 670.4 |
| 3LZT | SD200 | 1 | allH | Flex | WT:ALA | Faster | 3LZT_G | 32 | PRO | 2 | Faster | 2386 |
| 3LZT | SD200 | 1 | allH | Flex | WT:ALA | Faster | 3LZT_G | 32 | VAL | 1 | Faster | 32.75 |
| 3LZT | SD200 | 1 | allH | Flex | WT:ALA | Faster | 3LZT_G | 32 | VAL | 2 | Faster | 55.04 |
| 3LZT | SD200 | 1 | allH | Flex | WT:ALA | Faster | 3LZT_G | 32 | VAL | 3 | Faster | 128.3 |
| 3LZT | SD200 | 1 | allH | Flex | WT:ALA | Faster | 3LZT_G | 32 | VAL | 4 | Faster | 85.35 |
| ... | | | | | | | | | | | | |
| 3LZT | SD200 | 1 | allH | Flex | WT:ALA | Faster | 3LZT_G | 32 | SER | 1 | Faster | 5.792 |
| 3LZT | SD200 | 1 | allH | Flex | WT:ALA | Faster | 3LZT_G | 32 | SER | 2 | Faster | 6.844 |
| 3LZT | SD200 | 1 | allH | Flex | WT:ALA | Faster | 3LZT_G | 32 | SER | 3 | Faster | 5.293 |
| ... | | | | | | | | | | | | |

TABLE 1-continued

| I | II | III | IV | V | VI | VII | VIII | IX | X | XI | XII | XIII |
|---|---|---|---|---|---|---|---|---|---|---|---|---|
| 3LZT | SD200 | 1 | allH | Flex | WT:ALA | Faster | 3LZT_G | 32 | ILE | 1 | Faster | 165.5 |
| 3LZT | SD200 | 1 | allH | Flex | WT:ALA | Faster | 3LZT_G | 32 | ILE | 2 | Faster | 253.2 |
| 3LZT | SD200 | 1 | allH | Flex | WT:ALA | Faster | 3LZT_G | 32 | ILE | 3 | Faster | 232.3 |
| ... | | | | | | | | | | | | |
| 3LZT | SD200 | 1 | allH | Flex | WT:ALA | Faster | 3LZT_G | 32 | LEU | 1 | Faster | 358 |
| 3LZT | SD200 | 1 | allH | Flex | WT:ALA | Faster | 3LZT_G | 32 | LEU | 2 | Faster | 732.4 |
| 3LZT | SD200 | 1 | allH | Flex | WT:ALA | Faster | 3LZT_G | 32 | LEU | 3 | Faster | 521.4 |
| ... | | | | | | | | | | | | |
| 3LZT | SD200 | 1 | allH | Flex | WT:ALA | Faster | 3LZT_G | 32 | PHE | 1 | Faster | 908 |
| 3LZT | SD200 | 1 | allH | Flex | WT:ALA | Faster | 3LZT_G | 32 | PHE | 2 | Faster | 1656 |
| 3LZT | SD200 | 1 | allH | Flex | WT:ALA | Faster | 3LZT_G | 32 | PHE | 3 | Faster | 2137 |
| ... | | | | | | | | | | | | |
| 3LZT | SD200 | 1 | allH | Flex | WT:ILE | Faster | 3LZT_G | 55 | GLY | 1 | Faster | 4.34 |
| 3LZT | SD200 | 1 | allH | Flex | WT:ILE | Faster | 3LZT_G | 55 | ALA | 1 | Faster | 2.783 |
| 3LZT | SD200 | 1 | allH | Flex | WT:ILE | Faster | 3LZT_G | 55 | PRO | 1 | Faster | 7.783 |
| 3LZT | SD200 | 1 | allH | Flex | WT:ILE | Faster | 3LZT_G | 55 | PRO | 2 | Faster | 23.26 |
| 3LZT | SD200 | 1 | allH | Flex | WT:ILE | Faster | 3LZT_G | 55 | VAL | 1 | Faster | 1530 |
| 3LZT | SD200 | 1 | allH | Flex | WT:ILE | Faster | 3LZT_G | 55 | VAL | 2 | Faster | 518.5 |
| 3LZT | SD200 | 1 | allH | Flex | WT:ILE | Faster | 3LZT_G | 55 | VAL | 3 | Faster | 80.25 |
| ... | | | | | | | | | | | | |
| 3LZT | SD200 | 1 | allH | Flex | WT:ILE | Faster | 3LZT_G | 55 | SER | 1 | Faster | 5.179 |
| 3LZT | SD200 | 1 | allH | Flex | WT:ILE | Faster | 3LZT_G | 55 | SER | 2 | Faster | 4.224 |
| 3LZT | SD200 | 1 | allH | Flex | WT:ILE | Faster | 3LZT_G | 55 | SER | 3 | Faster | 5.869 |
| ... | | | | | | | | | | | | |
| 3LZT | SD200 | 1 | allH | Flex | WT:ILE | Faster | 3LZT_G | 55 | ILE | 9 | Faster | 84.37 |
| 3LZT | SD200 | 1 | allH | Flex | WT:ILE | Faster | 3LZT_G | 55 | ILE | 10 | Faster | 0 |
| 3LZT | SD200 | 1 | allH | Flex | WT:ILE | Faster | 3LZT_G | 55 | ILE | 11 | Faster | 0.4476 |
| ... | | | | | | | | | | | | |
| 3LZT | SD200 | 1 | allH | Flex | WT:ILE | Faster | 3LZT_G | 55 | LEU | 12 | Faster | 189.5 |
| 3LZT | SD200 | 1 | allH | Flex | WT:ILE | Faster | 3LZT_G | 55 | LEU | 13 | Faster | 5.599 |
| 3LZT | SD200 | 1 | allH | Flex | WT:ILE | Faster | 3LZT_G | 55 | LEU | 14 | Faster | 145.4 |
| ... | | | | | | | | | | | | |
| 3LZT | SD200 | 1 | allH | Flex | WT:ILE | Faster | 3LZT_G | 55 | PHE | 1 | Faster | 9.99E+05 |
| 3LZT | SD200 | 1 | allH | Flex | WT:ILE | Faster | 3LZT_G | 55 | PHE | 2 | Faster | 5.88E+05 |
| 3LZT | SD200 | 1 | allH | Flex | WT:ILE | Faster | 3LZT_G | 55 | PHE | 3 | Faster | 3.39E+08 |
| ... | | | | | | | | | | | | |

TABLE 1 shows a compilation of single residue ECO's generated by the present method. Each line represents an ECO. The columns are labeled according to the list described in the section FORMAL DESCRIPTION OF ECO'S. Only basic ECO properties are shown. 3LZT is the PDB code for hen lysozyme; SD200: 200 steps steepest descent energy minimization; all H: CHARMM force field of Brooks et al. (cited supra), including explicit hydrogen atoms and TTS contributions as listed in Table 3; Flex: all "flexible" residues having a rotatable side chain; WT:res: WT residue "res" as observed in 3LZT; 3LZT_G: global minimum energy conformation for 3LZT. The value "1" in column III refers to the rotamer library of De Maeyer et al. (cited supra).

TABLE 2

| pos | WT | GLY | ALA | PRO | VAL | SER | CYS | THR | ILE | LEU | ASP |
|---|---|---|---|---|---|---|---|---|---|---|---|
| 1 | LYS | 5.393 | 4.808 | 72.34 | 5.448 | 3.745 | 100 | 3.85 | 7.888 | 3.487 | 4.417 |
| 2 | VAL | 3.281 | 1.826 | −1.219 | 0.000 | 2.181 | 100 | 1.597 | 0.4949 | 2.905 | −1.593 |
| 3 | PHE | 10.12 | 8.73 | 100 | 70.45 | 9.215 | 100 | 18.02 | 75.28 | 6.772 | 12.07 |
| 4 | GLY | 0.000 | −0.6605 | 188.4 | −1.841 | −3.037 | 100 | −2.98 | −1.451 | −1.385 | −2.933 |
| 5 | ARG | −2.052 | −2.955 | 8.138 | −3.549 | −4.842 | 100 | −4.443 | −2.272 | −0.7667 | −5.503 |
| 6 | CYS | 100 | 100 | 100 | 100 | 100 | 0.000 | 100 | 100 | 100 | 100 |
| 7 | GLU | 5.048 | 4.898 | 402.3 | 2.335 | 2.027 | 100 | 2.672 | 2.61 | 1.111 | 2.117 |
| 8 | LEU | 5.793 | 4.472 | 1220 | 12.26 | 3.764 | 100 | 26.02 | 41.45 | 0.000 | 12.49 |
| 9 | ALA | 0.8005 | 0.000 | 2072 | 62.55 | 1.565 | 100 | 16.86 | 136.7 | 97.43 | 39.37 |
| 10 | ALA | 3.083 | 0.000 | 364.5 | 6.618 | 1.906 | 100 | 1.503 | 9.388 | 0.1485 | −3.284 |
| 11 | ALA | 1.782 | 0.000 | 541.4 | 9.069 | 0.057 | 100 | 2.62 | 9.38 | 5.411 | 5.746 |
| 12 | MET | 2.882 | 6.678 | 878.6 | 38.15 | 4.784 | 100 | 8.915 | 36.87 | 11.29 | 8.075 |
| 13 | LYS | 6.852 | 2.989 | 792.1 | 7.331 | 5.694 | 100 | 5.703 | 40.98 | 6.538 | 5.413 |
| 14 | ARG | −2.063 | −4.292 | 1773 | −1.594 | −3.028 | 100 | −4.176 | −2.385 | −3.231 | 1.051 |
| 15 | HIS | −6.665 | −6.38 | 1686 | 6.251 | −5.89 | 100 | −6.074 | 29.58 | 1.38 | −3.371 |
| 16 | GLY | 0.000 | 5.167 | 3.25E+12 | 67.43 | 9.153 | 100 | 27.81 | 29.08 | 7.546 | 8.569 |
| 17 | LEU | 8.529 | 6.551 | 1884 | 17.76 | 6.421 | 100 | 4.534 | 53.78 | 0.000 | 7.65 |
| 18 | ASP | 1.38 | 0.9228 | 16.84 | 5.34 | −1.209 | 100 | −1.72 | 13.29 | 6.838 | 0.000 |
| 19 | ASN | −2.948 | −1.913 | 9.40E+08 | 7.3445 | −1.198 | 100 | 1.66 | 4.593 | −0.8527 | 0.1945 |
| 20 | TYR | 8.395 | 6.114 | 9070 | 17.52 | 6.637 | 100 | 20.06 | 17.99 | 7.139 | 6.815 |
| 21 | ARG | −1.621 | −3.643 | 1.80E+10 | 18.34 | −3.093 | 100 | 3.791 | 4.843 | 4.673 | −2.58 |
| 22 | GLY | 0.000 | 8.119 | 7.88E+11 | 26.17 | 7.271 | 100 | 13.98 | 18.86 | 13.91 | 8.322 |
| 23 | TYR | 10.12 | 6.976 | 2214 | 5.021 | 7.194 | 100 | 9.943 | 6.506 | 11.16 | 8.951 |
| 24 | SER | 1.098 | −0.7391 | 15.88 | 0.9515 | 0.000 | 100 | 0.7865 | 0.1856 | −0.5185 | −9.9154 |
| 25 | LEU | 1.436 | 5.448 | 72.67 | 18.89 | 7.257 | 100 | 9.459 | 16.31 | 0.000 | 10.48 |

TABLE 2-continued

| | | | | | | | | | | |
|---|---|---|---|---|---|---|---|---|---|---|
| 26 | GLY | 0.000 | 413.2 | 72.8 | 2906 | 488.8 | 100 | 6.72E+04 | 7422 | 3759 | 576.5 |
| 27 | ASN | 3.262 | 1.816 | 5519 | 5.026 | −0.2109 | 100 | −0.161 | 7.191 | 8.994 | −0.5562 |
| 28 | TRP | 17.26 | 16.29 | 1.11E+04 | 38.91 | 16.8 | 100 | 20.82 | 42.03 | 15.44 | 18.27 |
| 29 | VAL | 6.676 | 5.784 | 2143 | 0.000 | 4.114 | 100 | 2.796 | 6.174 | 21.26 | 5.064 |
| 30 | CYS | 100 | 100 | 100 | 100 | 100 | 0.000 | 100 | 100 | 100 | 100 |
| 31 | ALA | 1.829 | 0.000 | 1476 | 58.55 | 0.5887 | 100 | −1.06 | 145.7 | 122.5 | 9.451 |
| 32 | ALA | 1.944 | 0.000 | 670.4 | 32.75 | 3.042 | 100 | 25.14 | 156.9 | 290.2 | 58.79 |
| 33 | LYS | 0.3971 | −0.4244 | 2413 | 30.82 | 0.060 | 100 | 4.057 | 39.72 | 2.541 | −2.799 |
| 34 | PHE | 5.282 | 4.738 | 1496 | 10.49 | 5.211 | 100 | 3.614 | 12.01 | 8.443 | 3.627 |
| 35 | GLU | −4.431 | −6.218 | 800.3 | 21.72 | −8.055 | 100 | −4.839 | 129.9 | −0.279 | 17.6 |
| 36 | SER | 3.591 | 0.926 | 2.25E+04 | 57.35 | 0.000 | 100 | 25.42 | 400.6 | 6537 | 141.8 |
| 37 | ASN | 1.402 | −0.4658 | 4.35E+08 | 11.49 | 0.4319 | 100 | 6.368 | 4.874 | −0.1753 | 0.7699 |
| 38 | PHE | 8.244 | 6.079 | 5.12E+09 | 339.2 | 9.921 | 100 | 20.63 | 177.4 | 5.658 | 4.183 |
| 39 | ASN | 4.559 | 2.964 | 1766 | 7.849 | 2.35 | 100 | 3.313 | 3.054 | 5.994 | −1.255 |
| 40 | THR | 0.9648 | −1.342 | 1215 | 14.77 | 0.8346 | 100 | 0.000 | 28.2 | 7.831 | 5.793 |
| 41 | GLN | 0.5118 | −0.599 | 13.37 | 2.208 | −2.107 | 100 | −3.109 | 2.815 | −0.2787 | −0.1364 |
| 42 | ALA | 1.887 | 0.000 | 190.5 | 21.59 | 0.5344 | 100 | 4.219 | 23.34 | 35.57 | 5.14 |
| 43 | THR | 2.643 | −0.4468 | 13.4 | −1.936 | 0.6394 | 100 | 0.000 | −2.14 | 12.75 | 4.164 |
| 44 | ASN | 4.585 | 2.837 | 3.40E+04 | 3.555 | 5.712 | 100 | 6.253 | 2.771 | 2.181 | 5.291 |
| 45 | ARG | −1.964 | −3.796 | −6.478 | 4096 | −2.206 | 100 | −2.708 | −4.016 | −1.927 | −4.39 |
| 46 | ASN | 5.849 | 5.375 | 1.72E+04 | 7.695 | 7.83 | 100 | 9.095 | 8.181 | 4.493 | 3.67 |
| 47 | THR | −0.1194 | −1.357 | 8.153 | −1.179 | −0.2641 | 100 | 0.000 | −0.4753 | −0.4937 | −0.3787 |
| 48 | ASP | 3.072 | 1.801 | 50.67 | 0.8852 | −0.1421 | 100 | 0.016 | 3.45 | 1.837 | 0.000 |
| 49 | GLY | 0.000 | 11.01 | 5.41E+09 | 226.4 | 21.75 | 100 | 83.87 | 81.68 | 20.62 | 26.97 |
| 50 | SER | −2.755 | −2.275 | 78.36 | 21.58 | 0.000 | 100 | 3.124 | 40.33 | 107.7 | 1.318 |

| pos | ASN | PHE | TYR | TRP | MET | GLU | GLN | LYS | ARG | HIS |
|---|---|---|---|---|---|---|---|---|---|---|
| 1 | 5.698 | 3.197 | 4.647 | 5.295 | 1.59 | 2.688 | 1.885 | 0.000 | 3.654 | 2.87 |
| 2 | 0.4249 | 4.991 | 5.04 | 7.449 | 1.689 | 2.9 | 2.913 | 0.4943 | 2.241 | 5.063 |
| 3 | 10.46 | 0.000 | −1.361 | 3.071 | 6.441 | 12.9 | 10.49 | 12.68 | 7.076 | 4.701 |
| 4 | 0.4594 | −0.8102 | −0.1396 | 2.266 | −0.1753 | −4.024 | 0.8653 | −0.2155 | 3.071 | −0.050 |
| 5 | −5.619 | 7.291 | 5.133 | 9.747 | −3.488 | −5.483 | −2.816 | −2.112 | 0.000 | −2.046 |
| 6 | 100 | 100 | 100 | 100 | 100 | 100 | 100 | 100 | 100 | 100 |
| 7 | 7.227 | 6.817 | 7.035 | 11.62 | 4.23 | 0.000 | 1.512 | 7.179 | 9.046 | 6.931 |
| 8 | 10.08 | 42.79 | 48.99 | 182.1 | 20.34 | 9.464 | 6.824 | 70.65 | 104.2 | 43.09 |
| 9 | 33.74 | 173.3 | 188.3 | 208.9 | 32.29 | 99.8 | 51.03 | 104.8 | 119.7 | 67.77 |
| 10 | 0.062 | 2.425 | 2.267 | 3.813 | 0.6235 | −0.5627 | −0.5718 | 1.679 | −5.199 | 4.627 |
| 11 | 4.65 | 0.8659 | 0.5695 | 5.324 | 0.6988 | 3.71 | 6.77 | 3.079 | 0.6966 | 3.72 |
| 12 | 6.182 | 2.992 | 3.006 | 104.3 | 0.000 | 3.997 | 1.491 | 25.42 | 7.127 | 6.104 |
| 13 | 5.318 | 6.165 | 7.002 | 8.353 | 5.877 | 8.446 | 7.051 | 0.000 | 8.214 | 6.398 |
| 14 | −1.702 | −0.8066 | −2.032 | 3.512 | −1.955 | −2.235 | −2.782 | −2.859 | 0.000 | 0.2366 |
| 15 | −5.431 | −0.3028 | 0.4972 | 4.455 | −6.559 | −7.577 | −7.105 | −6.646 | −4.206 | 0.000 |
| 16 | 10.58 | 5.203 | 5.124 | 10.2 | 10.53 | 12.23 | 6.564 | 5.826 | 13.76 | 7.48 |
| 17 | 4.853 | 24.15 | 163.4 | 133.5 | 10.07 | 7.276 | 8.038 | 14.88 | 77.52 | 6.509 |
| 18 | 1.235 | 3.968 | 3.539 | 6.153 | 1.621 | −4.022 | 0.406 | 3.11 | 8.335 | 2.084 |
| 19 | 0.000 | −3.388 | −2.707 | 0.2491 | 0.046 | 3.029 | 1.476 | −2.997 | 5.017 | −0.042 |
| 20 | 5.69 | −0.249 | 0.000 | 5.22 | 6.818 | 5.681 | 6.36 | 11.83 | 9.342 | 7.475 |
| 21 | −0.8562 | −2.193 | −1.52 | 1.711 | −3.325 | 0.5204 | −0.466 | −5.685 | 0.000 | −1.446 |
| 22 | 12.36 | 6.307 | 7.39 | 10.98 | 16.81 | 17.57 | 11.47 | 11.83 | 20.12 | 9.072 |
| 23 | 8.435 | 1.542 | 0.000 | 5.193 | 17.71 | 8.649 | 7.118 | 24.57 | 12.92 | 9.825 |
| 24 | 0.1757 | 1.455 | 1.732 | 2.719 | −0.095 | −8.693 | −6.357 | 0.085 | −0.2637 | 0.3541 |
| 25 | 7.968 | 130.8 | 123.6 | 99.29 | 4.815 | 3.108 | 2.329 | 34.93 | 53.48 | 27.52 |
| 26 | 532 | 677.8 | 749.5 | 277.9 | 474.8 | 644.7 | 1549 | 1207 | 1010 | 173.6 |
| 27 | 0.000 | 1.823 | 2.121 | 12.23 | 2.069 | 0.6558 | 4.712 | 0.8609 | 6.779 | 0.090 |
| 28 | 17.27 | 8.01 | 5.768 | 0.000 | 12.65 | 21.79 | 15.79 | 18.92 | 10.3 | 6.546 |
| 29 | 5.974 | 850.3 | 756.6 | 498.5 | 80.01 | 39.03 | 28.86 | 116.8 | 247.4 | 81.64 |
| 30 | 100 | 100 | 100 | 100 | 100 | 100 | 100 | 100 | 100 | 100 |
| 31 | 5.958 | 519.2 | 385.8 | 1788 | 53.14 | 46.33 | 22.31 | 99.98 | 76.54 | 59.34 |
| 32 | 41.19 | 157.2 | 201.5 | 329.6 | 134.4 | 237 | 114.1 | 165.5 | 212.8 | 83.42 |
| 33 | −1.312 | −3.276 | −2.54 | 4.067 | −1.984 | −3.427 | −0.4108 | 0.000 | −0.6887 | 0.876 |
| 34 | 4.259 | 0.000 | −1.287 | 5.524 | 5.494 | 6.074 | 6.232 | 9.168 | 9.371 | 5.287 |
| 35 | 5.857 | 107.9 | 1018 | 185.4 | 41.73 | 0.000 | 14.69 | 55.5 | 133.7 | 37.62 |
| 36 | 99.41 | 2236 | 4807 | 1910 | 514.1 | 313 | 157.4 | 417.6 | 5701 | 910.8 |
| 37 | 0.000 | 1.666 | 1.261 | 4.068 | 0.3995 | 1.602 | 2.154 | 0.6332 | −0.6882 | 4.073 |
| 38 | 1.996 | 0.000 | 2.87 | 3.547 | 20.44 | 22.42 | 10.46 | 11.78 | 17.07 | 7.017 |
| 39 | 0.000 | 6.132 | 6.023 | 15.13 | 3.445 | 1.299 | 4.21 | 4.822 | 5.066 | 2.931 |
| 40 | 0.4273 | 48.97 | 48.05 | 145.2 | 16.38 | 10.83 | 1.687 | 24.94 | 53.96 | 21 |
| 41 | −1.165 | −1.053 | −1.419 | 2.519 | 1.174 | −1.2 | 0.000 | 0.1047 | 2.685 | −0.263 |
| 42 | 10 | 6.085 | 5.325 | 7.67 | 0.5431 | 3.6 | 5.07 | 7.77 | 5.485 | 3.054 |
| 43 | 4.081 | 8.137 | 8.103 | 10.83 | 0.2002 | −0.5656 | 0.3179 | 1.624 | 1.624 | 8.908 |
| 44 | 0.000 | 5.252 | 4.929 | 8.913 | 4.438 | 4.503 | 0.8133 | −1.346 | 1.907 | 5.219 |
| 45 | −5.778 | −3.135 | −3.884 | −1.394 | −1.412 | −2.193 | −3.218 | −3.242 | 0.000 | −1.311 |
| 46 | 0.000 | 11.71 | 10.2 | 9.011 | 5.677 | 5.838 | 4.908 | 2.689 | 7.508 | 5.452 |
| 47 | 0.5125 | 1.691 | 1.789 | 5.213 | 1.474 | −0.1983 | 0.3976 | 0.7072 | 1.16 | 2.168 |
| 48 | 4.053 | 4.818 | 4.787 | 8.861 | 3.455 | −1.836 | 0.033 | 4.793 | 7.367 | 4.381 |
| 49 | 22.52 | 20.65 | 20.18 | 22.09 | 18.71 | 19.81 | 15.52 | 12.29 | 22.3 | 16.47 |
| 50 | 6.679 | 56.61 | 50.87 | 58.91 | −0.1183 | 4.727 | 0.7738 | 3.184 | 26.9 | 22.02 |

TABLE 2 shows a compilation of single residue GECO energies generated by the present method. GECO energies are shown for the first 50 residues of the protein structure referred to by the PDB code 3LZT. The GECO energies shown have been generated from the data in a database of ECO's according to TABLE 1, using the min-operator over all rotamers for the same residue (eq. (10)). The energies are expressed in kcal mol$^{-1}$. The first column shows the residue position in 3LZT at which all naturally occurring amino acid residues (indicated in the first row) have been modeled. The second column shows the WT residue at each position. It can be seen that all GECO energies for WT substitutions are equal to zero since the reference structure has been calculated on the basis of the WT amino acid sequence. All values for CYS substitutions are arbitrary set to 100 kcal mol$^{-1}$ except when the WT sequence has a CYS residue at that position, in which case the value is set to 0 kcal mol$^{-1}$.

TABLE 3

|  | GLY | ALA | PRO | VAL | SER | THR | ILE |
|---|---|---|---|---|---|---|---|
| (semi-)buried | −0.368 | −1.786 | −22.240 | −4.562 | 1.315 | 2.224 | −5.639 |
| (semi-)exposed | −1.508 | −1.384 | −19.094 | −1.964 | −0.039 | 1.748 | −2.682 |
|  | LEU | ASP | ASN | PHE | TYR | TRP | MET |
| (semi-)buried | −4.755 | 10.852 | 10.106 | 4.161 | 7.087 | 7.349 | −1.015 |
| (semi-)exposed | −1.608 | 3.115 | 7.069 | 5.588 | 7.442 | 9.129 | −0.211 |
|  |  |  | GLU | GLN | LYS | ARG | HIS |
|  |  | (semi-)buried | 7.638 | 7.158 | 1.777 | 7.542 | 8.864 |
|  |  | (semi-)exposed | 1.020 | 4.730 | −1.204 | 7.592 | 6.468 |

TABLE 3 shows a set of TTS terms, obtained by the method described in the section ENERGY FUNCTION, for 19 naturally occurring amino acid residue types and two classes of solvent exposure. Cys reside types have not been included in the TTS parameter optimization procedure. The solvent exposure classes are defined as follows: (semi-) buried: ASA %<25%; (semi-)exposed: 25%≦ASA %. All values are expressed in kcal mol$^{-1}$. The computations were performed on 22 protein structures (PDB codes: 3LZT, 1A3C, 1A62, 1AAC, 1AH7, 1AHO, 1AIE, 1AMM, 1AVM, 1AWD, 1BRT, 1BTK, 1CEX, 1CVL, 1EDG, 1EDM, 1FMK, 1G3P, 1GVP, 1IRO, 1IXH, 1KQH). The rotamer library of De Maeyer et al. (cited supra) and the CHARMM force field of Brooks et al. (cited supra) with explicit hydrogen atoms were used.

TABLE 4

| 5\30 | GLY | ALA | PRO | VAL | SER | CYS | THR | ILE | LEU | ASP |
|---|---|---|---|---|---|---|---|---|---|---|
| GLY | 0.18 | −0.18 | 0.28 | −5.96 | 0.02 | 0.54 | 0.64 | −15.91 | −6.79 | 1.71 |
| ALA | −0.93 | −1.02 | −0.66 | −7.17 | −1.35 | −0.49 | −0.79 | −17.06 | −5.77 | −0.45 |
| PRO | −3.83 | −3.88 | −3.62 | −10.28 | −4.10 | −3.52 | −3.59 | −20.22 | −9.17 | −3.49 |
| VAL | −7.71 | −8.23 | −7.80 | −6.05 | −8.16 | 0.11 | −1.42 | −16.01 | −5.36 | 0.58 |
| SER | −0.47 | −0.95 | −0.47 | −6.78 | −0.55 | −0.38 | 0.00 | −16.78 | −5.71 | 0.68 |
| CYS | −0.06 | −0.27 | 0.09 | −6.23 | −0.56 | 0.01 | −0.10 | −16.05 | −5.56 | −0.10 |
| THR | −6.99 | −7.76 | −7.23 | −12.58 | −7.19 | −5.47 | −5.97 | −20.73 | −5.39 | −1.76 |
| ILE | −4.98 | −4.29 | −3.16 | 0.19 | −4.53 | 0.30 | 0.42 | 0.06 | −5.25 | 0.56 |
| LEU | 0.00 | 0.00 | 0.00 | 0.00 | 0.00 | 0.00 | 0.00 | 0.00 | 0.00 | 0.00 |
| ASP | 1.02 | 0.12 | 0.58 | −2.05 | 1.06 | 0.23 | 1.49 | −11.76 | −5.20 | 1.69 |
| ASN | 0.43 | 0.37 | 0.61 | −5.42 | −0.35 | 0.53 | −0.04 | −15.04 | −5.17 | 0.07 |
| PHE | −5.75 | −3.24 | −3.00 | −3.29 | −3.87 | 0.93 | 1.98 | −7.58 | −4.86 | 1.47 |
| TYR | −5.30 | −3.57 | −3.23 | −3.73 | −4.46 | 0.58 | 6.71 | 99.82 | 93.70 | 7.92 |
| TRP | 3.21 | 2.99 | 4.07 | −0.92 | −0.53 | 2.89 | 3.32 | −8.50 | −3.51 | 2.81 |
| MET | 1.01 | 0.43 | 0.78 | 0.64 | 0.57 | 0.49 | 0.82 | 0.31 | −3.84 | 1.07 |
| GLU | −3.53 | −4.17 | −3.83 | −1.17 | −3.90 | −1.84 | −0.61 | −5.25 | 2.48 | −0.84 |
| GLN | 1.22 | 0.27 | 0.93 | 1.14 | 1.27 | 0.54 | 2.02 | −7.65 | −4.90 | 1.61 |
| LYS | −3.74 | −1.13 | −1.44 | 1.19 | −2.79 | 0.87 | −0.87 | −3.52 | −2.23 | −1.04 |
| ARG | −1.17 | 0.15 | −0.47 | −0.10 | −0.74 | −0.09 | −1.09 | −4.83 | 0.01 | −1.10 |
| HIS | −4.32 | −3.45 | −3.07 | −2.90 | −3.38 | 1.00 | 2.70 | −10.47 | −3.84 | 2.91 |

| 5\30 | ASN | PHE | TYR | TRP | MET | GLU | GLN | LYS | ARG | HIS |
|---|---|---|---|---|---|---|---|---|---|---|
| GLY | 1.10 | 0.00 | −3.70 | −1.48 | −3.80 | −8.37 | −0.87 | −6.27 | −13.87 | 1.42 |
| ALA | −0.54 | 0.00 | −2.91 | −2.80 | −1.66 | −9.34 | −1.69 | −2.23 | −7.59 | −0.01 |
| PRO | −3.57 | 0.00 | 0.71 | 20.15 | −2.75 | −11.76 | −4.97 | −4.69 | −10.38 | −3.07 |
| VAL | 0.29 | 0.00 | −1.42 | −0.50 | −1.11 | −6.94 | −1.30 | −1.91 | −9.65 | −4.21 |
| SER | −0.07 | 0.00 | −2.79 | −2.88 | −1.03 | −9.20 | −1.50 | −3.33 | −5.63 | 0.26 |

TABLE 4-continued

| | | | | | | | | | |
|---|---|---|---|---|---|---|---|---|---|
| CYS | −0.14 | 0.00 | −3.24 | −3.34 | −1.64 | −7.38 | −1.34 | −1.90 | −1.57 | 0.27 |
| THR | −2.92 | 0.00 | −1.41 | 0.24 | −1.57 | −8.43 | −2.58 | −2.47 | −9.15 | −5.12 |
| ILE | 0.45 | 0.00 | −0.78 | 2.73 | −1.10 | −4.99 | −1.34 | −1.37 | −5.01 | 0.68 |
| LEU | 0.00 | 0.00 | 0.00 | 0.00 | 0.00 | 0.00 | 0.00 | 0.00 | 0.00 | 0.00 |
| ASP | 0.26 | 0.00 | −2.95 | −3.25 | −0.34 | −4.83 | −1.07 | −3.69 | −2.37 | 0.82 |
| ASN | 0.37 | 0.00 | −3.15 | −2.80 | −0.80 | −7.04 | −2.50 | −1.50 | −1.05 | 1.05 |
| PHE | −1.17 | 0.00 | 0.35 | −2.20 | −1.81 | −6.25 | −1.91 | −1.94 | −3.80 | 0.61 |
| TYR | −0.92 | 0.00 | 2.99 | 25.24 | −2.02 | −4.22 | 0.62 | 129.25 | −4.77 | −0.20 |
| TRP | 2.56 | 0.00 | −2.88 | −2.22 | −2.03 | −4.03 | −0.29 | −2.67 | −1.54 | 0.99 |
| MET | 0.83 | 0.00 | −1.85 | 0.08 | −0.24 | −4.91 | −0.63 | −2.14 | −0.33 | 0.64 |
| GLU | −0.33 | 0.00 | −3.26 | −2.17 | −0.23 | −7.02 | −3.81 | −5.30 | −5.41 | −0.45 |
| GLN | −0.26 | 0.00 | −3.41 | −2.75 | −1.38 | −3.57 | 0.89 | −2.49 | −1.83 | 0.61 |
| LYS | 0.52 | 0.00 | −0.48 | −0.45 | −0.92 | −7.34 | −2.04 | −1.93 | −1.39 | −0.83 |
| ARG | −0.02 | 0.00 | 0.63 | −0.40 | −1.47 | −8.28 | −3.35 | −2.11 | −5.12 | −0.18 |
| HIS | −1.96 | 0.00 | 0.37 | −1.35 | −1.67 | −8.63 | −1.71 | −0.78 | −6.70 | 1.24 |

TABLE 4 shows the fuse terms for all possible double mutations at residue positions 5 and 30 of the B1 domain of protein G (PDB code 1PGA), derived in accordance with eq. (47). Values are expressed in kcal mol$^{-1}$.

---

The invention claimed is:

1. A method for analyzing a protein structure, the method being executed in a computer under the control of a program stored in the computer, and comprising the following steps:
   A) receiving, by the computer, a reference structure for a protein, whereby
      the said reference structure forms a representation of a three-dimensional structure of the said protein, and has a global energy $E_{ref}$,
      the protein consists of a plurality of residue positions, each carrying a particular reference amino acid type in a specific reference conformation, and
      the protein residues are classified into a set of modelled residue positions and a set of conformationally fixed residues;
   B) substituting, by the computer, into the reference structure of step (A) a pattern, whereby
      the said pattern consists of one or more of the modelled residue positions defined in step (A), each carrying a particular amino acid residue type being placed at a specific residue position in the reference structure and adopting a specific conformation, and
      the one or more amino acid residue types of the said pattern are replacing the corresponding amino acid residue types present in the reference structure;
   C) optimizing, by the computer, the conformation of the reference structure of step (A) being substituted by the pattern of step (B), whereby
      a suitable protein structure optimization method based on a function allowing to assess the quality of a global protein structure, or any part thereof, is used in combination with a suitable conformational search method, and
      the said structure optimization method is applied to all modelled residue positions defined in step (A) not being located at any of the pattern residue positions defined in step (B), with the proviso that said structure optimization method is not applied to any of said pattern residue positions;
   D) assessing, by the computer, the energetic compatibility of the pattern defined in step (B) within the context of the reference structure defined in step (A) being structurally optimized in step (C) with respect to the said pattern, by way of comparing the global energy $E(p)$ of the substituted and optimized protein structure with the global energy $E_{ref}$ of the non-substituted reference structure to obtain an energetic compatibility object energy $E_{ECO}(p)$; and
   E) generating and outputting, by the computer, to a display, a user, a readily accessible memory, another computer on a network, or another computer-readable medium, in the form of an energetic compatibility object (ECO), a value reflecting the said energetic compatibility of the pattern together with information forming a full description of the three-dimensional structure comprising the substituted pattern.

2. The method according to claim 1, wherein the reference structure of step (A) further represents the three-dimensional structure of ligands including co-factors, ions or water molecules.

3. The method according to claim 1, wherein the pattern of step (B) consists of a series of consecutive, interconnected residue positions, the said pattern being referred to as a loop pattern.

4. The method according to claim 1, wherein each of the pattern residue positions carrying a particular amino acid residue type as defined in step (B) are assigned a specific conformation which is received from a rotamer library, the said pattern being referred to as a rotameric pattern.

5. The method according to claim 1, wherein each of the pattern residue positions carrying a particular amino acid residue type as defined in step (B) are assigned a specific conformation which is received from a backbone-independent rotamer library, the said library being referred to as a side-chain rotamer library, and the said pattern being referred to as a rotameric pattern.

6. The method according to claim 1, wherein each of the pattern residue positions carrying a particular amino acid residue type as defined in step (B) are assigned a specific conformation which is received from a backbone-dependent rotamer library, the said pattern being referred to as a rotameric pattern, the said library being referred to as a combined main-chain/side-chain rotamer library, and wherein each of the said pattern residue positions are assigned a fixed conformation in accordance with a full main-chain/side-chain rotamer known in the said rotamer library for the corresponding amino acid residue type located at each pattern residue position.

7. The method according to claim 1, wherein the said function allowing to assess the quality of a global protein structure is an energy function allowing to assess the potential or free energy of a global protein structure or any part thereof.

8. The method according to claim 1, wherein the said conformational search method of step (C) includes a method comprising the steps of:
   (a) receiving a three dimensional representation of the molecular structure of a protein, the said representation comprising a first set of residue portions and a template;
   (b) modifying the representation of step (a) by at least one optimization cycle; characterized in that each optimization cycle comprises the steps of:
      (b1) perturbing a first representation of the molecular structure by modifying the structure of one or more of the first set of residue portions;
      (b2) relaxing the perturbed representation by optimizing the structure of one or more of the non-perturbed residue portions of the first set with respect to the one or more perturbed residue portions;
      (b3) evaluating the perturbed and relaxed representation of the molecular structure by using a function which is an energetic cost function and replacing the first representation by the perturbed and relaxed representation if the latter's global energy is more optimal than that of the first representation; and
   (c) terminating the optimization process according to step (b) when a predetermined termination criterion is reached; and
   (d) outputting to a storage medium or to a consecutive method a data structure comprising information extracted from step (b).

9. The method according to claim 1, wherein the function allowing to assess the quality of a global protein structure in step (C) is an energy function which includes an energetic contribution accounting for solvation effects.

10. The method according to claim 1, wherein the function allowing to assess the quality of a global protein structure in step (C) is an energy function which includes an energetic contribution accounting for solvation effects and the said energetic contribution for solvation effects is a type-dependent, topology-specific solvation method including establishing a set of energetic parameters for each of different classes of solvent exposure.

11. The method according to claim 1, wherein the function allowing to assess the quality of a global protein structure in step (C) is an energy function which includes an energetic contribution accounting for solvation effects and the said energetic contribution for solvation effects is a type-dependent, topology-specific solvation (TTS) method including establishing a set of energetic parameters for each of different classes of solvent exposure and wherein:

first, each residue type at a given residue position in a specific rotameric state is substituted into the protein structure and its accessible surface area (ASA) is calculated, next, a class assignment occurs on the basis of the percentage ASA of the residue side chain in the protein structure compared to the maximal ASA of the same side chain being shielded from the solvent only by its own main-chain atoms, and finally an appropriate type- and topology-specific energy, ETTS(T,C), for the considered pattern element is retrieved from a table of TTS values, using the pattern type (T) and class (C) indices.

12. An executable program product, comprising a computer-readable storage medium embodied therein, said storage medium to be executed to implement a method for analyzing a protein structure on a computing system with a processor and memory, said method comprising:

A) receiving a reference structure for a protein, whereby
   the said reference structure forms a representation of a three-dimensional structure of the said protein, and has a global energy $E_{ref}$,
   the protein consists of a plurality of residue positions, each carrying a particular reference amino acid type in a specific reference conformation, and
   the protein residues are classified into a set of modeled residue positions and a set of conformationally fixed residues;

B) substituting into the reference structure of step (A) a pattern, wherein
   the said pattern consists of one or more of the modeled residue positions defined in step (A), each carrying a particular amino acid residue type being placed at a specific residue position in the reference structure and adopting a specific conformation, and
   the one or more amino acid residue types of the said pattern are replacing the corresponding amino acid residue types present in the reference structure;

C) optimizing the conformation of the reference structure of step (A) being substituted by the pattern of step (B), whereby
   a suitable protein structure optimization method based on a function allowing to assess the quality of a global protein structure, or any part thereof, is used in combination with a suitable conformational search method, and
   the said structure optimization method is applied to all modeled residue positions defined in step (A) not being located at any of the pattern residue positions defined in step (B), with the proviso that said structure optimization method is not applied to any of said pattern residue positions;

D) assessing the energetic compatibility of the pattern defined in step (B) within the context of the reference structure defined in step (A) being structurally optimized in step (C) with respect to the said pattern, by way of comparing the global energy E(p) of the substituted and optimized protein structure with the global energy of the non-substituted reference structure to obtain the energetic compatibility object energy $E_{ECO}(p)$; and E) generating and outputting to a display, a user, a readily accessible memory, another computer on a network, or another computer-readable medium an energetic compatibility object (ECO) reflecting the said energetic compatibility of the pattern together with information forming a full description of the three-dimensional structure comprising the substituted pattern.

13. A computing system comprising a processor and memory, wherein said computing system is programmed with an executable program comprising:

A) receiving a reference structure for a protein, whereby
   the said reference structure forms a representation of a three-dimensional structure of the said protein, and has a global energy $E_{ref}$,
   the protein consists of a plurality of residue positions, each carrying a particular reference amino acid type in a specific reference conformation, and
   the protein residues are classified into a set of modeled residue positions and a set of conformationally fixed residues;

B) substituting into the reference structure of step (A) a pattern, wherein
   the said pattern consists of one or more of the modeled residue positions defined in step (A), each carrying a particular amino acid residue type being placed at a specific residue position in the reference structure and adopting a specific conformation, and
   the one or more amino acid residue types of the said pattern are replacing the corresponding amino acid residue types present in the reference structure;

C) optimizing the conformation of the reference structure of step (A) being substituted by the pattern of step (B), whereby
   a suitable protein structure optimization method based on a function allowing to assess the quality of a global protein structure, or any part thereof, is used in combination with a suitable conformational search method, and
   the said structure optimization method is applied to all modeled residue positions defined in step (A) not being located at any of the pattern residue positions defined in step (B), with the proviso that said structure optimization method is not applied to any of said pattern residue positions;

D) assessing the energetic compatibility of the pattern defined in step (B) within the context of the reference structure defined in step (A) being structurally optimized in step (C) with respect to the said pattern, by way of comparing the global energy E(p) of the substituted and optimized protein structure with the global energy of the non-substituted reference structure to obtain the energetic compatibility object energy $E_{ECO}(p)$; and E) generating and outputting to a display, a user, a readily accessible memory, another computer on a network, or another computer-readable medium an energetic compatibility object (ECO) reflecting the said energetic compatibility of the pattern together with information forming a full description of the three-dimensional structure comprising the substituted pattern.

* * * * *

SEQUENCE LISTING

<160> NUMBER OF SEQ ID NOS: 12

<210> SEQ ID NO 1
<211> LENGTH: 129
<212> TYPE: PRT
<213> ORGANISM: Gallus gallus
<220> FEATURE:
<221> NAME/KEY: MISC_FEATURE
<222> LOCATION: (1)..(129)
<223> OTHER INFORMATION: Egg white lysosyme

<400> SEQUENCE: 1

Lys Val Phe Gly Arg Cys Glu Leu Ala Ala Met Lys Arg His Gly
 1               5                  10                  15

Leu Asp Asn Tyr Arg Gly Tyr Ser Leu Gly Asn Trp Val Cys Ala Ala
                20                  25                  30

Lys Phe Glu Ser Asn Phe Asn Thr Gln Ala Thr Asn Arg Asn Thr Asp
            35                  40                  45

Gly Ser Thr Asp Tyr Gly Ile Leu Gln Ile Asn Ser Arg Trp Trp Cys
    50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu

<210> SEQ ID NO 2
<211> LENGTH: 13
<212> TYPE: PRT
<213> ORGANISM: artificial sequence
<220> FEATURE:
<223> OTHER INFORMATION: Fragment Chain A Human lactalbumin  : AA 1-13

<400> SEQUENCE: 2

Lys Gln Phe Thr Lys Cys Glu Leu Ser Gln Leu Leu Lys
 1               5                  10

-continued

```
<210> SEQ ID NO 3
<211> LENGTH: 30
<212> TYPE: PRT
<213> ORGANISM: artificial sequence
<220> FEATURE:
<223> OTHER INFORMATION: Fragment Chain A Human lactalbumin : AA 17-46

<400> SEQUENCE: 3

Gly Tyr Gly Gly Ile Ala Leu Pro Glu Leu Ile Cys Thr Met Phe His
1               5                   10                  15

Thr Ser Gly Tyr Asp Thr Gln Ala Ile Val Glu Asn Asp Glu
            20                  25                  30

<210> SEQ ID NO 4
<211> LENGTH: 46
<212> TYPE: PRT
<213> ORGANISM: artificial sequence
<220> FEATURE:
<223> OTHER INFORMATION: Fragment Chain A Human lactalbumin : AA 50-95

<400> SEQUENCE: 4

Tyr Gly Leu Phe Gln Ile Ser Asn Lys Leu Trp Cys Lys Ser Ser Gln
1               5                   10                  15

Val Pro Gln Ser Arg Asn Ile Cys Asp Ile Ser Cys Asp Lys Phe Leu
            20                  25                  30

Asp Asp Asp Ile Thr Asp Asp Ile Met Cys Ala Lys Lys Ile
        35                  40                  45

<210> SEQ ID NO 5
<211> LENGTH: 4
<212> TYPE: PRT
<213> ORGANISM: artificial sequence
<220> FEATURE:
<223> OTHER INFORMATION: Fragment Chain A Human lactalbumin : AA 69-72

<400> SEQUENCE: 5

Ser Arg Asn Ile
1

<210> SEQ ID NO 6
<211> LENGTH: 12
<212> TYPE: PRT
<213> ORGANISM: artificial sequence
<220> FEATURE:
<223> OTHER INFORMATION: Fragment Chain A Human lactalbumin : AA 92-103

<400> SEQUENCE: 6

Ala Lys Lys Ile Leu Asp Ile Lys Gly Ile Asp Tyr
1               5                   10

<210> SEQ ID NO 7
<211> LENGTH: 11
<212> TYPE: PRT
<213> ORGANISM: artificial sequence
<220> FEATURE:
<223> OTHER INFORMATION: Fragment Chain A Human lactalbumin : AA 92-102

<400> SEQUENCE: 7

Ala Lys Lys Ile Leu Asp Ile Lys Gly Ile Asp
1               5                   10

<210> SEQ ID NO 8
<211> LENGTH: 16
<212> TYPE: PRT
<213> ORGANISM: artificial sequence
<220> FEATURE:
<223> OTHER INFORMATION: Fragment Chain A Human lactalbumin : AA 95-110
```

```
<400> SEQUENCE: 8

Ile Leu Asp Ile Lys Gly Ile Asp Tyr Trp Leu Ala His Lys Ala Leu
1               5                   10                  15

<210> SEQ ID NO 9
<211> LENGTH: 14
<212> TYPE: PRT
<213> ORGANISM: artificial sequence
<220> FEATURE:
<223> OTHER INFORMATION: Fragment Chain A Human lactalbumin : AA 102-115

<400> SEQUENCE: 9

Asp Tyr Trp Leu Ala His Lys Ala Leu Cys Thr Glu Lys Leu
1               5                   10

<210> SEQ ID NO 10
<211> LENGTH: 5
<212> TYPE: PRT
<213> ORGANISM: artificial sequence
<220> FEATURE:
<223> OTHER INFORMATION: Fragment Chain A Human lactalbumin : AA 105-109

<400> SEQUENCE: 10

Leu Ala His Lys Ala
1               5

<210> SEQ ID NO 11
<211> LENGTH: 5
<212> TYPE: PRT
<213> ORGANISM: artificial sequence
<220> FEATURE:
<223> OTHER INFORMATION: Fragment Chain A Human lactalbumin : AA 114-118

<400> SEQUENCE: 11

Lys Leu Glu Gln Trp
1               5

<210> SEQ ID NO 12
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: Chain A lactalbumin

<400> SEQUENCE: 12

Lys Gln Phe Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Phe His
            20                  25                  30

Thr Ser Gly Tyr Asp Thr Gln Ala Ile Val Glu Asn Asp Glu Ser Thr
        35                  40                  45

Glu Tyr Gly Leu Phe Gln Ile Ser Asn Lys Leu Trp Cys Lys Ser Ser
    50                  55                  60

Gln Val Pro Gln Ser Arg Asn Ile Cys Asp Ile Ser Cys Asp Lys Phe
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
            100                 105                 110

Glu Lys Leu Glu Gln Trp Leu Cys Glu Lys Leu
        115                 120
```